(12) United States Patent
Bastos et al.

(10) Patent No.: US 8,703,811 B2
(45) Date of Patent: Apr. 22, 2014

(54) **SMALL MOLECULE INHIBITORS OF *PLASMODIUM FALCIPARUM* DIHYDROOROTATE DEHYDROGENASE**

(75) Inventors: Cecilia Bastos, South Grafton, MA (US); Michael L. Booker, Bridgewater, MA (US); Cassandra A. Celatka, Hull, MA (US); Jon C. Clardy, Jamaica Plain, MA (US); Joseph Cortese, Quincy, MA (US); Vishal P. Patel, Washington, DC (US); Renato Skerlj, Newton, MA (US); Roger C. Wiegand, Wayland, MA (US); Dyann F. Wirth, Boston, MA (US)

(73) Assignees: Genzyme Corporation, Cambridge, MA (US); Massachusetts Institute of Technology, Cambridge, MA (US); President and Fellows of Harvard College, Cambridge, MA (US)

( * ) Notice: Subject to any disclaimer, the term of this patent is extended or adjusted under 35 U.S.C. 154(b) by 184 days.

(21) Appl. No.: 12/991,305

(22) PCT Filed: May 7, 2009

(86) PCT No.: PCT/US2009/002845
§ 371 (c)(1),
(2), (4) Date: Feb. 9, 2011

(87) PCT Pub. No.: WO2009/137081
PCT Pub. Date: Nov. 12, 2009

(65) Prior Publication Data
US 2011/0130381 A1 Jun. 2, 2011

Related U.S. Application Data

(60) Provisional application No. 61/126,917, filed on May 7, 2008, provisional application No. 61/210,583, filed on Mar. 20, 2009.

(51) Int. Cl.
*A61K 31/381* (2006.01)
*A61K 31/4184* (2006.01)
*C07D 333/30* (2006.01)
*C07D 235/06* (2006.01)

(52) U.S. Cl.
USPC .......... 514/448; 514/393; 548/304.4; 549/63

(58) Field of Classification Search
None
See application file for complete search history.

(56) References Cited

U.S. PATENT DOCUMENTS

| 5,354,753 | A | * | 10/1994 | Ohi et al. | 514/81 |
| 2004/0236110 | A1 | * | 11/2004 | Ladouceur et al. | 546/277.4 |
| 2006/0122234 | A1 | * | 6/2006 | Archer et al. | 514/342 |

FOREIGN PATENT DOCUMENTS

| WO | WO 03/092686 A1 | 11/2003 |
| WO | WO 2008/015340 A2 | 2/2008 |
| WO | WO2009/098282 | * 8/2009 |

OTHER PUBLICATIONS

Montgomery, J. A., Piper, J. R., Elliott, R. D., Temple Jr, C., Roberts, E. C., Shealy, Y. F. Analogs of methotrexate. J. Med. Chem. Jul. 1979, 22, 862-868.*
Chemical Abstract Registry No. 895115-20-5, indexed in the Registry File on STN CAS Online Jul. 23, 2006.*
Baldwin, J., et al., "High-throughout Screening for Potent and Selective Inhibitors of *Plasmodium falciparum* Dihydroorotate Dehydrogenase," *J. Biolog. Chem.*, 280(23): pp. 21847-21853 (2005).
Booker, M., et al., "Novel Inhibitors of *Plasmodium falciparum* Dihydroorotate Dehydrogenase with Anti-malarial Activity in the Mouse Model", *J. Biolog. Chem.*, 285(43), pp. 33054-33064 (2010).
Heikkilä, T., et al., "The first de novo designed inhibitors of *Plasmodium falciparum* dihydroorotate dehydrogenase," *Bio. & Med. Chemistry Letters*, 16(1), pp. 88-92 (2006).
Legan, Jr., et al., "Biphenyl-4-ylcarbamoyl thiophene carboxylic acids as potent DHODH inhibitors," *Bio. & Med. Chemistry Letters*, 16(2) pp. 267-270 (2006).
Patel, V., et al., "Identification and Characterization of Small Molecule Inhibitors of *Plasmodium falciparum* Dihydroorotate Dehydrogenase", *J. Biolog. Chem.*, 283(50), pp. 35078-35085, 2008.
International Search Report for International Application No. PCT/US2009/002845 dated Sep. 16, 2010.
Baldwin, J., et al., "Malarial Dihydroorotate Dehydrogenase, Substrate and Inhibitor Specificity", *J Biol Chem*, 277(44):41827-34 (2002).
Liu, S., et al., "Structures of Human Dihydroorotate Dehydrogenase in Complex With Antiproliferative Agents," *Structure Fold Des.*, 8(1):25-33 (2000).
Skerlj, R.T., et al., "Optimization of Potent Inhibitors of *P. falciparum* Dihydroorotate Dehydrogenase for the Treatment of Malaria", *ACS Med. chem. Lett.* 2:708-713 (2011.

* cited by examiner

*Primary Examiner* — Michael Barker
*Assistant Examiner* — Po-Chih Chen
(74) *Attorney, Agent, or Firm* — Hamilton, Brook, Smith & Reynolds, P.C.

(57) ABSTRACT

Inhibitors of dihydroorotate dehydrogenase (DHODH) for the *Plasmodium* enzyme have been identified and characterized. The inhibitors have high specificity, submicromolar efficacy against cultured parasite strains, exhibit drug-like properties, and are not overtly cytotoxic.

11 Claims, 11 Drawing Sheets

```
                          1         10        20        30        40        50        60
P.falciparum      ..MISKLKPQFMELPKKHILSYCRKDVLNLFEQKFYYTSKRKESNNMKNESLLRLINYNRYYNKIDSNNY
P.berghei         .................................................................
P.vivax           MLRHSCLREKGNLIGGSLLRGTSAQLRAAGGGTFRSFHSYRSFCSFCIERRANKADANWYGCEPGHVAGG
H.sapiens         .................................................................
S.cerevisiae      .................................................................

70        80        90       100       110       120       130
P.falciparum      YNGGKILSNDRQYIYSPLCEYKKKINDISSYVSVPFKINIRNLGTSNFVNKKDVLDNDYIYENIKKEKIS
P.berghei         .........................................................MKRFDERMNKEKIS
P.vivax           ATCGPLRGDCAERHKLMAHVRRFSGESTRAKGGDKREGDIEGNRTNGSDKTKQLEEMKKLNEQIAREKG
H.sapiens         .........................................................MAWRHLKK
S.cerevisiae      .................................................................

140       150       160       170       180       190       200
P.falciparum      KHKKTIFLFVSLFGLYGFEESYNPEFFLYDIFLKFCLKYIDGEICHDLFLLLGKYNILPYDTSNDSIYA
P.berghei         KHKKVLFFTSSIVGLYMYEESYNPEFFMYDVFLDFCINYVDSEVCHDLFLLGKYGLLPYDTSNDSVYA
P.vivax           NHKKALLEIFTCVVALMYFESYDPEFFLYDVFLKMLLKYVDGETCHELFLLMGKYKLLPYDTGKDNIYS
H.sapiens         RAQDAVILGGGLIFASYLMATGDERFYAEHLMPTLQGLLIDPESAHRLAVRFTSLGLLPRARFQDSDML
S.cerevisiae      ..............................................................MTASL
```

```
                420       430       440       450       460       470       480
p.falciparum  NTTKKKPLVFVKLAPDLNQEKKEIADVLLETNIDGMIISNTTTQIND..IKSEENKKGGVSGAKLKDIS
p.berghei     NTTKKKPLVFVKLAPDLENSEKKKIAQVLIDTGIDGMIISNTTINKMD..IKSFEDKKGGVSGKKLKDLS
p.vivax       NTTKRRPLIFVKLAPDLEGERKSIANVLLNAEVDGMIICNTTQKFN..IKSFEDKKGGVSGEKLKGVS
H.sapiens     ......VHRPAVLVKIAPDLTSQKEDIASVVKELGIDGLIVTNTTVSRPAGLQGALRSETGGLSGKPLRDLS
s.cerevisiae  ......VKLPYFDFAHFDIMAKILNEFPLAYVNSINSIGNGLFIDVEKES.VVKPKNGFGCIGGEYVKPTA 490       500       510       520       530       540       550
p.falciparum  TKEICEMNYTNKQIPIHASGCIESGIDATEKIEACASVCQLYSQLVFNCMKSAVQIKPENHLLYQRGY
p.berghei     TNIISDMIYTNKQIPIHASGCIEGLTGADDAIEKIEACASVCQLYSQLVFNCVKSAIQIKPFNNALYQKGY
p.vivax       THMISQMNYTNGKIPIHASGCIEGHTGEFDAIEKIEACASVCQLYSQLVFNCMKAAVRIKPEDHLLYQRGY
H.sapiens     TQTIREMALTQGRVPIEGVSGQDAIEKIRAGASLVQLYTAHTFWCPVVGKVKPELEALLKEQEY
s.cerevisiae  LANVPAFTTRLREIKVFIGTGEIKSGKDAFEHLLGCASMQIGTELQKEGVKIFERIEKIKDIMEAKGY 560
p.falciparum  YNLKEAICRKHSKS......  SEQ ID NO : 1
p.berghei     YNLREAICKKHSNAKSLKV.  SEQ ID NO : 2
p.vivax       YKIGDAVCRAHRRAA.....  SEQ ID NO : 3
H.sapiens     GGVFDAIGADHRR.......  SEQ ID NO : 4
s.cerevisiae  TSIDQFRCKLNSI.......  SEQ ID NO : 5
```

SMALL MOLECULE INHIBITORS OF *PLASMODIUM FALCIPARUM* DIHYDROOROTATE DEHYDROGENASE

RELATED APPLICATION

This application is the U.S. National Stage of International Application No. PCT/US2009/002845, filed May 7, 2009, which designates the U.S., published in English, and claims the benefit of U.S. Provisional Application No. 61/210,583, filed Mar. 20, 2009 and U.S. Provisional Application No. 61/126,917, filed on May 7, 2008. The entire teachings of the above applications are incorporated herein by reference.

INCORPORATION BY REFERENCE OF MATERIAL IN ASCII TEXT FILE

This application incorporates by reference the Sequence Listing contained in the following ASCII text file:
a) File name 00502119003 SequenceListing.txt; created Aug. 9, 2012, 20 KB in size.

BACKGROUND OF THE INVENTION

Malaria is a vector-borne infectious disease caused by protozoan parasites and is widespread in tropical and subtropical regions, including parts of the Americas, Asia and Africa. Of the four *Plasmodium* parasite species that can infect humans (*P. falciparum, P. vivax, P. ovale* and *P. malariae*), the most serious forms of the disease are caused by *P. falciparum* and *P. vivax*. Of the approximately 515 million people infected yearly, between one and three million people, the majority of whom are young children in Sub-Saharan Africa, die from the disease. The current armament of approved anti-malarial drugs is limited to only a few targets within the human malaria parasite, and growing widespread resistance to current drugs is prompting the development of new antimalarial agents that have new biological targets.

Pyrimidines are required for the biosynthesis of DNA, RNA, glycoproteins, and phospholipids. Most organisms possess both a salvage and de novo pyrimidine biosynthetic pathway; however, the human malaria parasite *P. falciparum* cannot salvage preformed pyrimidine bases or nucleosides from its host and thus is entirely dependent on de novo biosynthesis [1, 2]. Dihydroorotate dehydrogenase (DHODH) is a flavoenzyme that catalyzes the oxidation of L-dihydroorotate (L-DHO) to orotate as part of the fourth sequential step of the de novo pyrimidine biosynthetic pathway [3-6].

Although the function of DHODH is conserved among all organisms, the enzyme family can be separated into two broad classes based upon sequence homology that correlates with cellular localization and preference for electron acceptors [6-9]. Both classes of enzyme perform a two-step reaction that most likely proceeds through a ping-pong mechanism [10-13]. Type 1 DHODH, as found in Gram-positive bacteria and the anaerobic yeast *Saccharomyces cerevisiae*, is located in the cytosol and utilizes fumarate or NAD as an electron acceptor to re-oxidize the flavin (FMN) prosthetic group in the second half reaction of the redox process [4, 14-17]. Type 2 DHODHs, generally found in eukaryotes and some Gram-negative bacteria [18-21], are membrane-bound and utilize quinones located in biological membranes as a final electron acceptor [22]. Both humans and all characterized members of the genus *Plasmodia* utilize a Type 2 DHODH for de novo pyrimidine biosynthesis [23-27]. Specifically, eukaryotic Type 2 DHODHs are localized to the inner mitochondrial space and utilize the respiratory chain quinone coenzyme $Q_n$ ($CoQ_n$), where the length of the isoprenoid unit (n) is variable, as a final electron acceptor.

The continued development of novel anti-malarial chemotherapies, particularly those aimed at new pathways, is necessary for the successful treatment of malaria as resistance to presently utilized drugs becomes more widespread. PfDHODH is likely to be an essential enzyme because the malaria parasite must rely on de novo biosynthesis for its metabolic needs. Identification of compounds able to inhibit pfDHODH could facilitate the development of effective antimalarials.

SUMMARY OF INVENTION

It has now been found that compounds of Formula I or pharmaceutically acceptable salts thereof are effective inhibitors of pfDHODH, have high specificity for the *Plasmodium* enzyme, have sub-micromolar efficacy against cultured parasite strains, exhibit drug-like properties and are not overtly cytotoxic.

One embodiment of the invention is an antimalarial compound of Formula I:

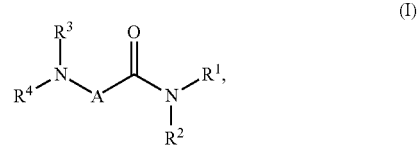

wherein
A is aryl or heteroaryl, each optionally substituted with one to three groups represented by $R^5$;
$R^1$, $R^2$, $R^3$ and $R^4$ are independently (a) hydrogen; or (b) ($C_1$-$C_{10}$)alkyl, aryl($C_0$-$C_3$)alkyl, heteroaryl($C_0$-$C_3$)alkyl, cycloalkyl($C_0$-$C_3$)alkyl, heterocyclyl($C_0$-$C_3$)alkyl, each optionally substituted with one or more groups represented by $R^5$; or
$R^1$ and $R^2$, along with the nitrogen to which they are attached, form a heterocyclyl or heteroaryl, wherein each can be monocyclic, bicyclic or tricyclic, wherein the heterocyclyl or heteroaryl formed is optionally substituted by one or more groups represented by $R^5$; or
$R^3$ and $R^4$, along with the nitrogen to which they are attached, form a heterocyclyl or heteroaryl, wherein each can be monocyclic, bicyclic or tricyclic, wherein the heterocyclyl or heteroaryl formed is optionally substituted by one or more groups represented by $R^5$;
Each $R^5$ is independently selected from halogen, nitro, cyano, ($C_1$-$C_3$)alkyl, halo($C_1$-$C_3$)alkyl, hydroxy($C_1$-$C_3$)alkyl, ($C_1$-$C_3$)alkoxy, halo($C_1$-$C_3$)alkoxy, N($R^6$)$_2$, C(=NOH)NH$_2$, NR$^6$CON($R^6$)$_2$, CON($R^6$)$_2$, CO$_2$R$^6$, COR$^7$, OC(O)R$^6$, SO$_2$N($R^6$)$_2$, SO$_2$R$^7$, NR$^6$COR$^7$, NR$^6$CO$_2$R$^6$, NR$^6$SO$_2$R$^7$ and OC(=O)N($R^6$)$_2$;
Each $R^6$ is independently selected from (a) hydrogen; or (b) ($C_1$-$C_{10}$)alkyl or aryl($C_0$-$C_3$)alkyl, each optionally substituted with halogen, ($C_1$-$C_3$)alkoxy, ($C_1$-$C_3$)alkyl, halo($C_1$-$C_3$)alkyl, halo($C_1$-$C_3$)alkoxy, cyano, or nitro; and
Each $R^7$ is independently selected (a) hydrogen or halogen; or (b) ($C_1$-$C_{10}$)alkyl, ($C_1$-$C_{10}$)alkoxy, aryl($C_0$-$C_3$)alkyl or aryl($C_0$-$C_3$)alkoxy, each optionally substituted with halogen, ($C_1$-$C_3$)alkoxy, ($C_1$-$C_3$)alkyl, halo($C_1$-$C_3$)alkyl, halo($C_1$-$C_3$)alkoxy, cyano, or nitro;
or a pharmaceutically acceptable salt thereof.

Another embodiment of the present invention is a pharmaceutical composition comprising: i) a pharmaceutically acceptable carrier or diluent; and ii) an antimalarial compound disclosed herein, or a pharmaceutically acceptable salt thereof.

Another embodiment of the invention is a method of treating malaria comprising the step of administering to a mammal in need of such treatment an effective amount of an antimalarial compound disclosed herein, or a pharmaceutically acceptable salt thereof.

Another embodiment of the invention is the use of an antimalarial compound disclosed herein or a pharmaceutically acceptable salt thereof for the manufacture of a medicament for treating malaria in a mammal in need of such treatment.

Another embodiment of the invention is an antimalarial compound disclosed herein or a pharmaceutically acceptable salt thereof for use in treating malaria in a mammal in need of such treatment.

BRIEF DESCRIPTION OF THE DRAWINGS

FIGS. 2A-2C. Sequence alignment of DHODH from *P. falciparum, P. berghei, P. vivax, H. sapiens*, and *S. cerevisiae*. The *P. falciparum* enzyme shares 72% identity with pbDHODH, 65% identity with pvDHODH, 34% identity with hsDHODH, and 31% identity with scDHODH.

FIG. 5 FIGS. 5A-5D. Dose-effect plots presenting *P. falciparum* D10 or D10-scDHODH proliferation in the presence of chloroquine, atovaquone, or quaternary hits identified from the HTS.

DETAILED DESCRIPTION

Figure 1A:
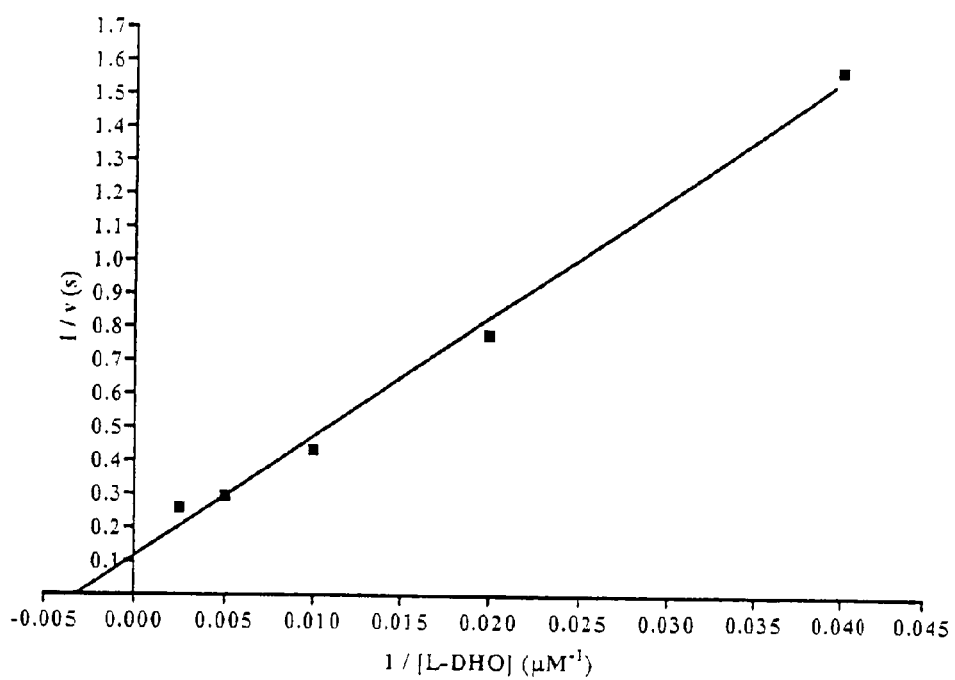
FIG. 1 Double-reciprocal plot of pfDHODH rate as a function of L-DHO (A) or $CoQ_D$ (B) concentration. The formation of orotate was directly measured to assess enzymatic rates. (A) The kinetic constants $k_{cat}$=5.6±0.5 s$^{-1}$ and $K_{m,\ L\text{-}DHO}^{app}$=154±29 μM were calculated by non-linear regression fitting of data to the Michaelis-Menten equation where the concentration of substrate $CoQ_D$, a soluble synthetic analog of ubiquinone, was kept constant at 100 μM and L-DHO varied from 25 to 400 μM. (B) The kinetic constants $k_{cat}$=3.6±0.2 s$^{-1}$ and $K_{m,\ CoQd}^{app}$=25±4 μM are based upon the velocity of orotate formation where the concentration of L-DHO is kept constant at 200 μM while $CoQ_D$ is varied from 1 to 200 μM.

Values and specific values for the variables in the above-described Structural Formula I have the following values:

A is aryl or heteroaryl, each optionally substituted with one to three groups represented by $R^5$.

$R^1$, $R^2$, $R^3$ and $R^4$ are independently (a) hydrogen; or (b) aryl($C_0$-$C_3$)alkyl, heteroaryl($C_0$-$C_3$)alkyl, cycloalkyl($C_0$-$C_3$)alkyl, heterocyclyl($C_0$-$C_3$)alkyl, each optionally substituted with one or more groups represented by $R^5$.

$R^1$ and $R^2$, along with the nitrogen to which they are attached, form a heterocyclyl or heteroaryl, wherein each can be monocyclic, bicyclic or tricyclic, wherein the heterocyclyl or heteroaryl formed is optionally substituted by one or more groups represented by $R^5$. In an alternative embodiment, $R^1$ and $R^2$ are independently (a) hydrogen; or (b) ($C_1$-$C_{10}$)alkyl, aryl($C_0$-$C_3$)alkyl, heteroaryl($C_0$-$C_3$)alkyl, cycloalkyl($C_0$-$C_3$)alkyl, heterocyclyl($C_0$-$C_3$)alkyl, each optionally substituted with one to three groups represented by $R^5$. In another embodiment, $R^1$ and $R^2$ are (a) hydrogen; or (b) ($C_1$-$C_{10}$)alkyl, phenyl, benzyl, cycloalkyl($C_0$-$C_3$)alkyl, each optionally substituted with halogen, nitro, cyano, ($C_1$-$C_3$)alkyl, halo($C_1$-$C_3$)alkyl, ($C_1$-$C_3$)alkoxy, halo($C_1$-$C_3$)alkoxy, $N(R^6)_2$, $NR^6CON(R^6)_2$, $CON(R^6)_2$, $CO_2R^6$ and $COR^7$. In another embodiment, $R^1$ and $R^2$ are independently selected from hydrogen, ($C_1$-$C_6$)alkyl and ($C_3$-$C_6$)cycloalkyl. In another embodiment, $R^1$ is ($C_1$-$C_6$)alkyl or ($C_3$-$C_6$)cycloalkyl and $R^2$ is hydrogen. In another embodiment, $R^1$ and $R^2$ are hydrogen.

In another embodiment, $R^3$ and $R^4$ are independently (a) hydrogen; or (b) ($C_1$-$C_{10}$)alkyl, aryl($C_0$-$C_3$)alkyl, heteroaryl ($C_0$-$C_3$)alkyl, cycloalkyl($C_0$-$C_3$)alkyl, heterocyclyl($C_0$-$C_3$) alkyl, each optionally substituted with one or more groups represented by $R^5$. Alternatively, $R^3$ and $R^4$, along with the nitrogen to which they are attached, form a heterocyclyl or heteroaryl, wherein each can be monocyclic, bicyclic or tricyclic, wherein the heterocyclyl or heteroaryl formed is optionally substituted by one to three groups represented by $R^5$. In another embodiment, the heterocyclyl or heteroaryl, formed from $R^3$ and $R^4$ together with the nitrogen to which they are attached, is a ($C_5$-$C_{20}$)heterocyclyl or ($C_5$-$C_{20}$)heteroaryl, each optionally substituted with one to three $R^5$. In another embodiment, the heterocyclyl or heteroaryl, formed from $R^3$ and $R^4$ together with the nitrogen to which they are attached, is selected from the group consisting of indolyl, indolinyl, imidazolyl, benzoimidazolyl, benzothiazinyl, benzooxazinyl, purinyl, dihydropyridothiazinyl, pyrazolyl, pyrrolidinyl, pyrrolyl, morpholinyl, piperidinyl, piperazinyl or benzopyridooxazepinyl, wherein the heterocyclyl or heteroaryl is optionally substituted by one to three groups represented by $R^5$.

Each $R^5$ is independently selected from halogen, nitro, cyano, ($C_1$-$C_3$)alkyl, halo($C_1$-$C_3$)alkyl, hydroxy($C_1$-$C_3$) alkyl, ($C_1$-$C_3$)alkoxy, halo($C_1$-$C_3$)alkoxy, $N(R^6)_2$, $C(=NOH)NH_2$, $NR^6CON(R^6)_2$, $CON(R^6)_2$, $CO_2R^6$, $COR^7$, $OC(O)R^6$, $SO_2N(R^6)_2$, $SO_2R^7$, $NR^6COR^7$, $NR^6CO_2R^6$, $NR^6SO_2R^7$ and $OC(=O)N(R^6)_2$. In another embodiment, each $R^5$ is independently selected from halogen, nitro, cyano, ($C_1$-$C_3$)alkyl, halo($C_1$-$C_3$)alkyl, ($C_1$-$C_3$)alkoxy, halo($C_1$-$C_3$) alkoxy, $N(R^6)_2$, $NR^6CON(R^6)_2$, $CON(R^6)_2$, $CO_2R^6$ and $COR^7$.

Alternatively, each $R^5$ is independently selected from halogen, nitro, cyano, hydroxy, ($C_1$-$C_3$)alkyl, halo($C_1$-$C_3$)alkyl, hydroxy($C_1$-$C_3$)alkyl, ($C_1$-$C_3$)alkoxy, halo($C_1$-$C_3$)alkoxy, aryl, haloaryl, $N(R^6)_2$, $C(=NOH)NH_2$, $NR^6CON(R^6)_2$, $CON(R^6)_2$, $CO_2R^6$, $COR^7$, $OC(O)R^6$, $SO_2N(R^6)_2$, $SO_2R^7$, $NR^6COR^7$, $NR^6CO_2R^6$, $NR^6SO_2R^7$ and $OC(=O)N(R^6)_2$;

Each $R^6$ is independently selected from (a) hydrogen; or (b) ($C_1$-$C_{10}$)alkyl or aryl($C_0$-$C_3$)alkyl, each optionally substituted with halogen, ($C_1$-$C_3$)alkoxy, ($C_1$-$C_3$)alkyl, halo($C_1$-$C_3$)alkyl, halo($C_1$-$C_3$)alkoxy, cyano or nitro. In another embodiment, each $R^6$ is independently selected from (a) hydrogen; or (b) ($C_1$-$C_4$)alkyl, aryl($C_0$-$C_2$)alkyl, each optionally substituted with halogen, $(C_1-C_3)$alkoxy, $(C_1-C_3)$alkyl, halo$(C_1-C_3)$alkyl or halo$(C_1-C_3)$alkoxy.

Each $R^7$ is independently selected (a) hydrogen or halogen; or (b) $(C_1-C_{10})$alkyl, $(C_1-C_{10})$alkoxy, aryl$(C_0-C_3)$alkyl or aryl$(C_0-C_3)$alkoxy, each optionally substituted with halogen, $(C_1-C_3)$alkoxy, $(C_1-C_3)$alkyl, halo$(C_1-C_3)$alkyl, halo$(C_1-C_3)$alkoxy, cyano or nitro.

In another embodiment, each $R^7$ is independently selected (a) hydrogen; or (b) $(C_1-C_4)$alkyl, $(C_1-C_4)$alkoxy, aryl$(C_0-C_2)$alkyl or aryl$(C_0-C_2)$alkoxy, each optionally substituted with halogen, $(C_1-C_3)$alkoxy, $(C_1-C_3)$alkyl, halo$(C_1-C_3)$alkyl or halo$(C_1-C_3)$alkoxy.

Another embodiment is an antimalarial compound of Formula II:

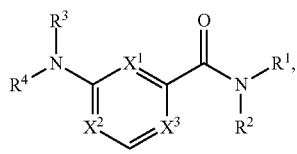

(II)

wherein $X_1$, $X_2$, and $X_3$ are independently CH, $CR^5$ or N, provided at least one of $X_1$, $X_2$, or $X_3$ is CH or $CR^5$; or a pharmaceutically acceptable salt thereof, wherein values and specific values of the remaining variables are as defined for Formula I above.

Another embodiment is an antimalarial compound of Formula III:

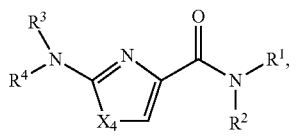

(III)

wherein $X_4$ is S, O or $NR^6$; or a pharmaceutically acceptable salt thereof, wherein values and specific values of the remaining variables are as defined for Formula I above.

Another embodiment is an antimalarial compound of Formula IV:

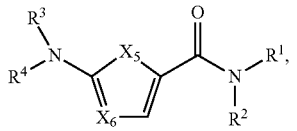

(IV)

wherein $X_5$ is S, O or $NR^6$; and
$X_6$ is N, CH, or $CR^5$;

or a pharmaceutically acceptable salt thereof, wherein values and specific values of the remaining variables are as defined for Formula I above.

Another embodiment is an antimalarial compound of Formula V:

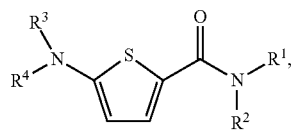

(V)

or a pharmaceutically acceptable salt thereof, wherein values and specific values of the variables are as defined for Formula I above.

In a first specific embodiment for the antimalarial compounds of Formulas I-V, $R^1$ and $R^2$ are independently (a) hydrogen; or (b) aryl$(C_0-C_3)$alkyl, heteroaryl$(C_0-C_3)$alkyl, cycloalkyl$(C_0-C_3)$alkyl, heterocyclyl$(C_0-C_3)$alkyl, each optionally substituted with one to three groups represented by $R^5$; and $R^3$ and $R^4$, along with the nitrogen to which they are attached, form a heterocyclyl or heteroaryl, wherein each can be monocyclic, bicyclic or tricyclic, wherein the heterocyclyl or heteroaryl formed is optionally substituted by one to three groups represented by $R^5$, wherein values and specific values of the remaining variables are as defined for Formulas I-V above.

In a second specific embodiment for the antimalarial compounds of Formulas I-V, the heterocyclyl or heteroaryl, formed from $R^3$ and $R^4$ together with the nitrogen to which they are attached, is a $(C_5-C_{20})$heterocyclyl or $(C_5-C_{20})$heteroaryl, each optionally substituted with one to three groups represented by $R^5$, wherein values and specific values of the remaining variables are as defined for the first specific embodiment for Formulas I-V above.

In another specific embodiment for the antimalarial compounds of Formulas I-V, the heterocyclyl or heteroaryl, formed from $R^3$ and $R^4$ together with the nitrogen to which they are attached, is selected from the group consisting of indolyl, indolinyl, imidazolyl, benzoimidazolyl, benzothiazinyl, benzooxazinyl, purinyl, dihydropyridothiazinyl, pyrazolyl, pyrrolidinyl, pyrrolyl, morpholinyl, piperidinyl, piperazinyl or benzopyridooxazepinyl, wherein the heterocyclyl or heteroaryl is optionally substituted by one to three groups represented by $R^5$, wherein values and specific values of the remaining variables are as defined for the first specific embodiment for Formulas I-V above.

Another embodiment is an antimalarial compound of Formula IIa:

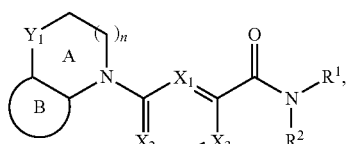

(IIa)

wherein n is 0 or 1;
$Y_1$ is $CH_2$, $CR^5_2$, S, O or $NR^6$; and
Ring B is either (a) absent; or (b) phenyl, pyridyl, or pyrimidyl, each optionally substituted with one to three groups represented $R^5$;
or a pharmaceutically acceptable salt thereof, wherein values and specific values of the remaining variables are as defined for Formula I or II above.

Another embodiment is an antimalarial compound of Formula IIb:

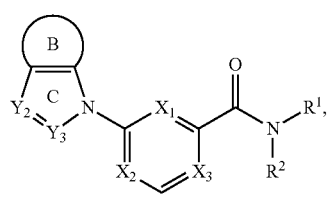

(IIb)

wherein
$Y_2$ and $Y_3$ are independently CH, $CR^5$ or N; provided that if $Y_3$ is N then $Y_2$ is CH or $CR^5$; and
Ring B is either (a) absent; or (b) phenyl, pyridyl, or pyrimidyl, each optionally substituted with one to three groups represented $R^5$;
or a pharmaceutically acceptable salt thereof, wherein values and specific values of the remaining variables are as defined for Formula I or II above.

Another embodiment is an antimalarial compound of Formula IIc:

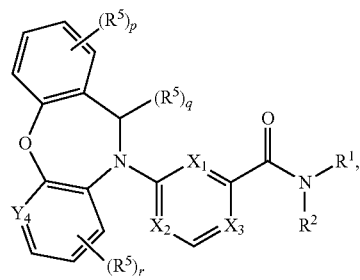

(IIc)

wherein
$Y_4$ is CH, $CR^5$ or N; and
p is 0 to 4,
q is 0 or 1; and
r is 0 to 3;
wherein $R^5$ is independently selected;
or a pharmaceutically acceptable salt thereof, wherein values and specific values of the remaining variables are as defined for Formula I or II above.

Another embodiment is an antimalarial compound is of Formula IIIa:

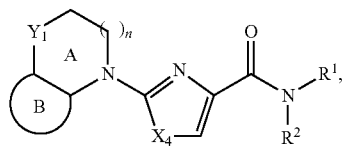

(IIIa)

wherein
n is 0 or 1;
$Y_1$ is $CH_2$, $CR^5_2$, S, O or $NR^6$; and
Ring B is either (a) absent; or (b) phenyl, pyridyl, or pyrimidyl, each optionally substituted with one to three groups represented $R^5$;
or a pharmaceutically acceptable salt thereof, wherein values and specific values of the remaining variables are as defined for Formula I or III above.

Another embodiment is an antimalarial compound is of Formula IIIb:

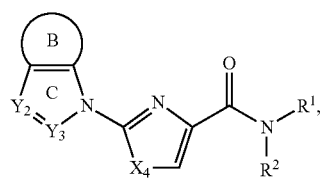

(IIIb)

wherein
$Y_2$ and $Y_3$ are independently CH, $CR^5$ or N; provided that if $Y_3$ is N then $Y_2$ is CH or $CR^5$; and
Ring B is either (a) absent; or (b) phenyl, pyridyl, or pyrimidyl, each optionally substituted with one to three groups represented $R^5$;
or a pharmaceutically acceptable salt thereof, wherein values and specific values of the remaining variables are as defined for Formula I or III above.

Another embodiment is an antimalarial compound is of Formula IIIc:

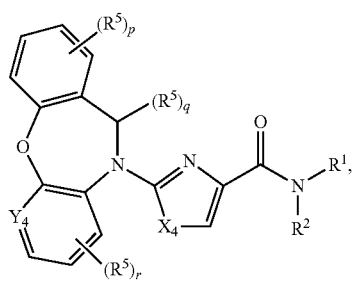

(IIIc)

wherein
$Y_4$ is CH, $CR^5$ or N; and
p is 0 to 4,
q is 0 or 1; and
r is 0 to 3;
wherein $R^5$ is independently selected;
or a pharmaceutically acceptable salt thereof, wherein values and specific values of the remaining variables are as defined for Formula I or III above.

Another embodiment is an antimalarial compound is of Formula IVa:

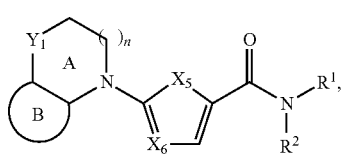

(IVa)

wherein
n is 0 or 1;
$Y_1$ is $CH_2$, $CR^5_2$, S, O or $NR^6$; and
Ring B is either (a) absent; or (b) phenyl, pyridyl, or pyrimidyl, each optionally substituted with one to three groups represented $R^5$;
or a pharmaceutically acceptable salt thereof, wherein values and specific values of the remaining variables are as defined for Formula I or IV above.

Another embodiment is an antimalarial compound is of Formula IVb:

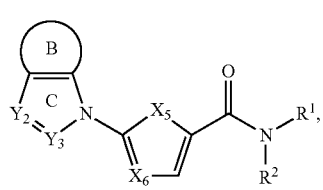

(IVb)

wherein
$Y_2$ and $Y_3$ are independently CH, $CR^5$ or N; provided that if $Y_3$ is N then $Y_2$ is CH or $CR^5$; and
Ring B is either (a) absent; or (b) phenyl, pyridyl, or pyrimidyl, each optionally substituted with one to three groups represented $R^5$;
or a pharmaceutically acceptable salt thereof, wherein values and specific values of the remaining variables are as defined for Formula I or IV above.

Another embodiment is an antimalarial compound is of Formula IVc:

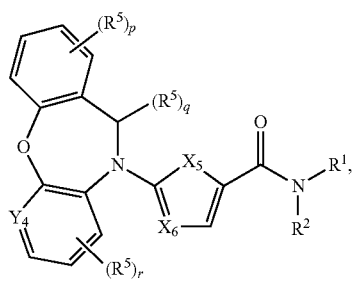

(IVc)

wherein
$Y_4$ is CH, $CR^5$ or N; and
p is 0 to 4,
q is 0 or 1; and
r is 0 to 3;
wherein $R^5$ is independently selected;
or a pharmaceutically acceptable salt thereof, wherein values and specific values of the remaining variables are as defined for Formula I or IV above.

Another embodiment is an antimalarial compound is of Formula Va:

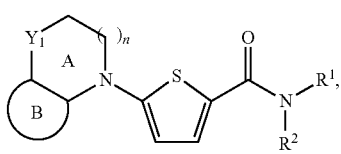

(Va)

wherein
n is 0 or 1;
$Y_1$ is $CH_2$, $CR^5_2$, S, O or $NR^6$; and
Ring B is either (a) absent; or (b) phenyl, pyridyl, or pyrimidyl, each optionally substituted with one to three groups represented $R^5$;
or a pharmaceutically acceptable salt thereof, wherein values and specific values of the remaining variables are as defined for Formula I or V above.

Another embodiment is an antimalarial compound is of Formula Vb:

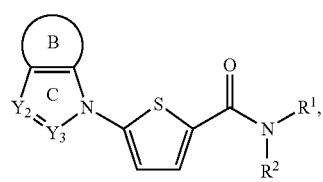

(Vb)

wherein
$Y_2$ and $Y_3$ are independently CH, $CR^5$ or N; provided that if $Y_3$ is N then $Y_2$ is CH, $CR^5$; and
Ring B is either (a) absent; or (b) phenyl, pyridyl, or pyrimidyl, each optionally substituted with one to three groups represented $R^5$;
or a pharmaceutically acceptable salt thereof, wherein values and specific values of the remaining variables are as defined for Formula I or V above.

Another embodiment is an antimalarial compound is of Formula Vc:

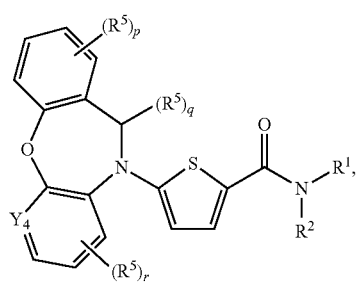

(Vc)

wherein
$Y_4$ is CH, $CR^5$ or N; and
p is 0 to 4,
q is 0 or 1; and
r is 0 to 3;
wherein $R^5$ is independently selected;
or a pharmaceutically acceptable salt thereof, wherein values and specific values of the remaining variables are as defined for Formula I or V above.

In a first specific embodiment for the antimalarial compounds of Formulas IIa-Va, Ring B is absent and Ring A is selected from piperidinyl, piperazinyl, morpholinyl and pyrrolidinyl, each optionally substituted with one to three groups represented $R^5$, wherein values and specific values of the remaining variables are as defined for Formulas I-V above.

In a second specific embodiment for the antimalarial compounds of Formulas IIa-Va, Ring B and Ring A taken together are selected from the group consisting of

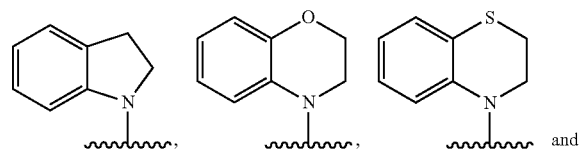

and

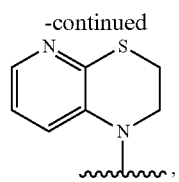

each optionally substituted with one to three groups represented $R^5$, wherein values and specific values of the remaining variables are as defined for Formulas I-V above.

In a specific embodiment for the antimalarial compounds of Formulas IIb-Vb, Ring B is absent and Ring C is selected from pyrrolyl, imidazolyl and pyrazolyl, each optionally substituted with one to three groups represented $R^5$, wherein values and specific values of the remaining variables are as defined for Formulas I-V above.

In an alternative specific embodiment for the antimalarial compounds of Formulas IIb-Vb, Ring B and Ring C taken together are selected from the group consisting of benzoimidazolyl, purinyl and indolyl, each optionally substituted with one to three groups represented $R^5$, wherein values and specific values of the remaining variables are as defined for Formulas I-V above.

In a specific embodiment for the antimalarial compounds of Formulas I-Vc, $R^1$ and $R^2$ are (a) hydrogen; or (b) $(C_1-C_{10})$ alkyl, phenyl, benzyl, cycloalkyl$(C_0-C_3)$alkyl, each optionally substituted with halogen, nitro, cyano, $(C_1-C_3)$alkyl, halo$(C_1-C_3)$alkyl, $(C_1-C_3)$alkoxy, halo$(C_1-C_3)$alkoxy, $N(R^6)_2$, $NR^6CON(R^6)_2$, $CON(R^6)_2$, $CO_2R^6$ and $COR^E$; or $R^1$ and $R^2$ are independently selected from hydrogen, $(C_1-C_6)$alkyl and $(C_3-C_6)$cycloalkyl; or $R^1$ is $(C_1-C_6)$alkyl or $(C_3-C_6)$cycloalkyl and $R^2$ is hydrogen; or $R^1$ and $R^2$ are hydrogen, and Each $R^5$ is independently selected from halogen, nitro, cyano, $(C_1-C_3)$alkyl, halo$(C_1-C_3)$alkyl, $(C_1-C_3)$alkoxy, halo$(C_1-C_3)$alkoxy, $N(R^6)_2$, $NR^6CON(R^6)_2$, $CON(R^6)_2$, $CO_2R^6$ and $COR^7$, and values and specific values of the remaining variables are as defined for the antimalarial compounds disclosed above.

In a specific embodiment for the antimalarial compounds of Formulas I-Vc, $R^1$, $R^2$ and $R^5$ are described in the previous paragraph, each $R^6$ is independently selected from (a) hydrogen; or (b) $(C_1-C_4)$alkyl, aryl$(C_0-C_2)$alkyl, each optionally substituted with halogen, $(C_1-C_3)$alkoxy, $(C_1-C_3)$alkyl, halo$(C_1-C_3)$alkyl or halo$(C_1-C_3)$alkoxy, and values and specific values of the remaining variables are as defined for the antimalarial compounds disclosed above.

In a specific embodiment for the antimalarial compounds of Formulas I-Vc, $R^1$, $R^2$, $R^5$ and $R^6$ are described in the previous paragraph, each $R^7$ is independently selected (a) hydrogen; or (b) $(C_1-C_4)$alkyl, $(C_1-C_4)$alkoxy, aryl$(C_0-C_2)$ alkyl or aryl$(C_0-C_2)$alkoxy, each optionally substituted with halogen, $(C_1-C_3)$alkoxy, $(C_1-C_3)$alkyl, halo$(C_1-C_3)$alkyl or halo$(C_1-C_3)$alkoxy, and values and specific values of the remaining variables are as defined for the antimalarial compounds disclosed above.

Another embodiment is a compound of any one of the following Formulas:

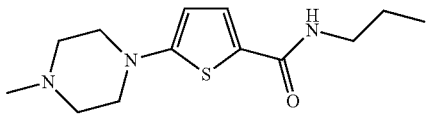

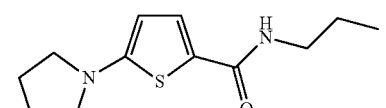

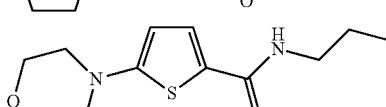

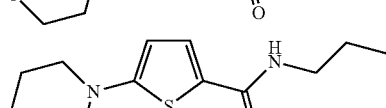

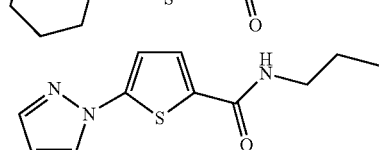

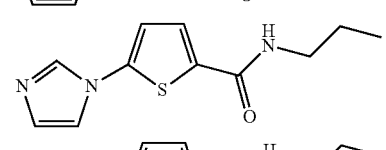

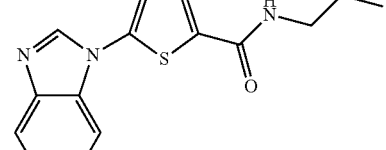

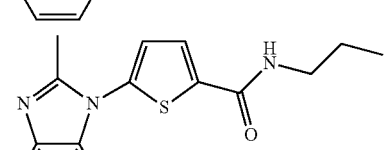

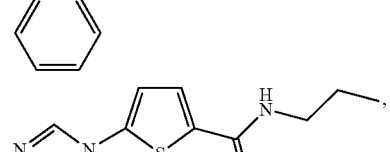

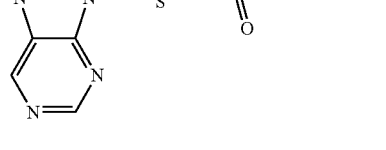

or a pharmaceutically acceptable salt thereof.

Another embodiment is a pharmaceutical composition comprising: i) a pharmaceutically acceptable carrier or diluent; and ii) the antimalarial compounds disclosed herein or a pharmaceutically acceptable salt thereof.

In one embodiment, the following compounds and pharmaceutically acceptable salts thereof are excluded from the invention:

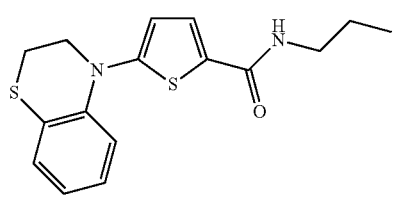
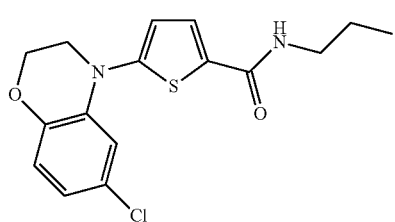
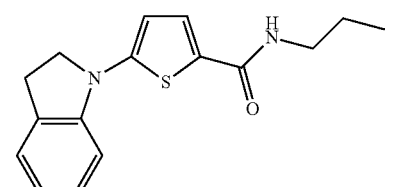
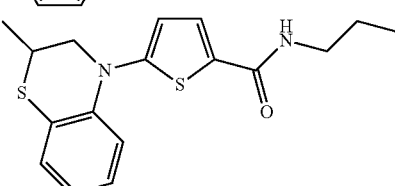
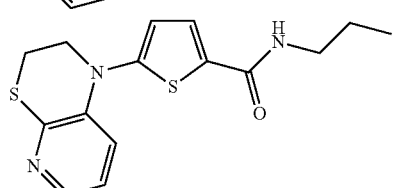
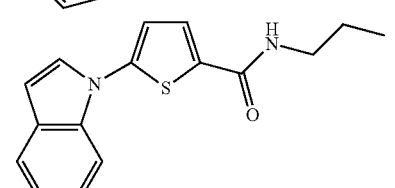
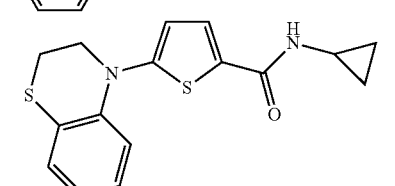
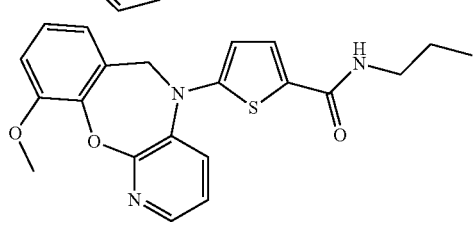

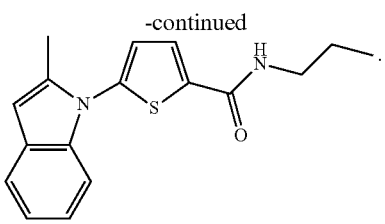

-continued

Another embodiment of the invention is a method of treating malaria comprising the step of administering to a mammal in need of such treatment an effective amount of an antimalarial compound disclosed herein or a pharmaceutically acceptable salt thereof.

Another embodiment of the invention is the use of an antimalarial compound disclosed herein or a pharmaceutically acceptable salt thereof for the manufacture of a medicament for treating malaria in a mammal in need of such treatment.

Another embodiment of the invention is an antimalarial compound disclosed herein or a pharmaceutically acceptable salt thereof for use in treating malaria in a mammal in need of such treatment.

Another embodiment is a method of treating a subject with malaria, comprising the step of administering to the subject an effective amount of an antimalarial compound disclosed herein.

DEFINITIONS

The term "alkyl", used alone or as part of a larger moiety such as "alkoxyalkyl" or "alkylamine" means a straight or branched hydrocarbon radical having 1-10 carbon atoms and includes, for example, methyl, ethyl, n-propyl, isopropyl, n-butyl, sec-butyl, isobutyl, tert-butyl, n-pentyl, i-pentyl, n-hexyl, n-heptyl, n-octyl, n-nonyl, n-decyl and the like.

The term "cycloalkyl", used alone or as part of a larger moiety, means a monocyclic, bicyclic or tricyclic, saturated hydrocarbon ring having 3-10 carbon atoms and includes, for example, cyclopropyl, cyclobutyl, cyclopentyl, cyclohexyl, cycloheptyl, cyclooctyl, bicyclo[2.2.2]octyl, bicyclo[2.2.1]heptyl, spiro[4.4]nonane, adamantyl and the like. Unless otherwise described, exemplary substituents for a substituted cycloalkyl group include groups represented by $R^5$.

"Aryl", used alone or as part of a larger moiety as in "arylalkyl", "arylalkoxy", or "aryloxyalkyl", means a 6-10 membered carbocyclic aromatic monocyclic or polycyclic ring system. Examples include phenyl and naphthyl. The term "aryl" also includes phenyl rings fused to non-aromatic carbocyclic ring or to a heterocyclyl group. The term "aryl" may be used interchangeably with the terms "aromatic group", "aryl ring" "aromatic ring", "aryl group" and "aromatic group". Unless otherwise described, exemplary substituents for a substituted aryl group include the include groups represented by $R^5$.

"Hetero" refers to the replacement of at least one carbon atom member in a ring system with at least one heteroatom selected from N, S, and O. A hetero ring may have 1, 2, 3, or 4 carbon atom members replaced by a heteroatom.

"Heteroaryl", used alone or as part of a larger moiety as in "heteroarylalkyl" or "heteroarylalkoxy", means a 5-10 membered monovalent heteroaromatic monocyclic and polycylic ring radical containing 1 to 4 heteroatoms independently selected from N, O, and S. The term "heteroaryl" also includes monocyclic heteroaryl ring fused to non-aromatic carbocyclic ring or to a heterocyclyl group. Heteroaryl groups include furyl, thienyl, thiophenyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridinyl-N-oxide, pyridazinyl, pyrimidinyl, pyrazinyl, indolizinyl, indolyl, isoindolyl, imidazo[4,5-b]pyridine, benzo[b]furyl, benzo[b] thienyl, indazolyl, benzimidazolyl, benzthiazolyl, purinyl, 4H-quinolizinyl, quinolinyl, isoquinolinyl, quinazolinyl, benzothienyl, benzofuranyl, 2,3-dihydrobenzofuranyl, benzodioxolyl, benzimidazolyl, indazolyl, benzisoxazolyl, benzoxazolyl, benzothiazolyl, cinnolinyl, phthalzinyl, quinazolinyl, quinoxalinyl, 1,8-naphthyridinyl, 1,2,3-triazolyl, 1,2,4-triazolyl, 1,3,4-oxadiazolyl, 1,2,5-thiadiazolyl, 1,2,5-thiadiazolyl-1-oxide, 1,2,5-thiadiazolyl-1,1-dioxide, 1,3,4-thiadiazolyl, 1,2,4-triazinyl, 1,3,5-triazinyl, tetrazolyl, and pteridinyl. The terms "heteroaryl", "heteroaromatic", "heteroaryl ring", "heteroaryl group" and "heteroaromatic group" are used interchangeably herein. "Heteroarylalkyl" means alkyl substituted with heteroaryl; and "heteroarylalkoxy" means alkoxy substituted with heteroaryl. Unless otherwise described, exemplary substituents for a substituted heteroaryl group include the include groups represented by $R^5$.

The term "heterocyclyl" means a 4-, 5-, 6- and 7-membered saturated or partially unsaturated heterocyclic ring containing 1 to 4 heteroatoms independently selected from N, O, and S. Exemplary heterocyclyls include azetidine, pyrrolidine, pyrrolidin-2-one, 1-methylpyrrolidin-2-one, piperidine, piperidin-2-one, 2-pyridone, 4-pyridone, piperazine, 1-(2,2,2-trifluoroethyl)piperazine, piperazin-2-one, 5,6-dihydropyrimidin-4-one, pyrimidin-4-one, tetrahydrofuran, tetrahydropyran, tetrahydrothiophene, tetrahydrothiopyran, isoxazolidine, 1,3-dioxolane, 1,3-dithiolane, 1,3-dioxane, 1,4-dioxane, 1,3-dithiane, 1,4-dithiane, oxazolidin-2-one, imidazolidin-2-one, imidazolidine-2,4-dione, tetrahydropyrimidin-2(1H)-one, morpholine, N-methylmorpholine, morpholin-3-one, 1,3-oxazinan-2-one, thiomorpholine, thiomorpholine 1,1-dioxide, tetrahydro-1,2,5-thiaoxazole 1,1-dioxide, tetrahydro-2H-1,2-thiazine 1,1-dioxide, hexahydro-1,2,6-thiadiazine 1,1-dioxide, tetrahydro-1,2,5-thiadiazole 1,1-dioxide and isothiazolidine 1,1-dioxide. Unless otherwise described, exemplary substituents for a substituted heterocyclyl group include groups represented by $R^5$.

As used herein the terms "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

Malaria is an infection of red blood cells with the single-celled parasite *Plasmodium*. Malaria parasites are transmitted by female *Anopheles* mosquitoes. The parasites multiply within red blood cells, causing symptoms that include symptoms of anemia (light headedness, shortness of breath, tachycardia), as well as other general symptoms such as an enlarged spleen, fatigue, fever, chills, nausea, flu-like illness, and in severe cases, coma and death.

Certain of the disclosed compounds may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms. The symbol "*" in a structural formula represents the presence of a chiral carbon center. "R" and "S" represent the configuration of substituents around one or more chiral carbon atoms. Thus, "R*" and "S*" denote the relative configurations of substituents around one or more chiral carbon atoms.

"Racemate" or "racemic mixture" means a compound of equimolar quantities of two enantiomers, wherein such mixtures exhibit no optical activity; i.e., they do not rotate the plane of polarized light.

"Geometric isomer" means isomers that differ in the orientation of substituent atoms in relationship to a carbon-carbon double bond, to a cycloalkyl ring, or to a bridged bicyclic system. Atoms (other than H) on each side of a carbon-carbon double bond may be in an E (substituents are on opposite sides of the carbon-carbon double bond) or Z (substituents are oriented on the same side) configuration.

"R," "S," "S*," "R*," "E," "Z," "cis," and "trans," indicate configurations relative to the core molecule.

The compounds of the invention may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods.

When a disclosed compound is named or depicted by structure without indicating the stereochemistry, and the compound has at least one chiral center, it is to be understood that the name or structure encompasses one enantiomer of compound free from the corresponding optical isomer, a racemic mixture of the compound and mixtures enriched in one enantiomer relative to its corresponding optical isomer.

When a disclosed compound is named or depicted by structure without indicating the stereochemistry and has at least two chiral centers, it is to be understood that the name or structure encompasses a diastereomer free of other diastereomers, a pair of diastereomers free from other diastereomeric pairs, mixtures of diastereomers, mixtures of diastereomeric pairs, mixtures of diastereomers in which one diastereomer is enriched relative to the other diastereomer(s) and mixtures of diastereomeric pairs in which one diastereomeric pair is enriched relative to the other diastereomeric pair(s).

The compounds of the invention may be present in the form of pharmaceutically acceptable salts. For use in medicines, the salts of the compounds of the invention refer to non-toxic "pharmaceutically acceptable salts." Pharmaceutically acceptable salt forms include pharmaceutically acceptable acidic/anionic or basic/cationic salts.

Pharmaceutically acceptable acidic/anionic salts include, the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, malonate, mandelate, mesylate, methylsulfate, mucate, napsylate, nitrate, pamoate, pantothenate, phosphate/diphosphate, polygalacturonate, salicylate, stearate, subacetate, succinate, sulfate, hydrogensulfate, tannate, tartrate, teoclate, tosylate, and triethiodide salts.

Pharmaceutically acceptable basic/cationic salts include, the sodium, potassium, calcium, magnesium, diethanolamine, N-methyl-D-glucamine, L-lysine, L-arginine, ammonium, ethanolamine, piperazine and triethanolamine salts.

The disclosed compounds can be used alone (i.e. as a monotherapy) or in combination with another therapeutic agent effective for treating malaria. Alternatively, a pharmaceutical composition of the invention may comprise an antimalarial compound disclosed herein or a pharmaceutical salt thereof, as the only pharmaceutically active agent in the pharmaceutical composition. The disclosed antimalarial compounds can be used alone or in a combination therapy with one or more additional agents for the treatment of malaria.

A pharmaceutical composition of the invention may, alternatively or in addition to an antimalarial compound disclosed herein comprise a pharmaceutically acceptable salt of an antimalarial compound disclosed herein or a prodrug or pharmaceutically active metabolite of such a compound or salt and one or more pharmaceutically acceptable carriers therefore. Alternatively, a pharmaceutical composition of the invention may comprise an antimalarial compound disclosed herein or a pharmaceutical salt thereof as the only pharmaceutically active agent in the pharmaceutical composition.

The invention includes a therapeutic method for treating malaria in a subject in need thereof comprising administering to a subject in need thereof an effective amount of an antimalarial compound disclosed herein or pharmaceutically acceptable salt thereof of composition thereof. As used herein, "treating" or "treatment" includes both therapeutic and prophylactic treatment. Therapeutic treatment includes reducing the symptoms associated with a disease or condition and/or increasing the longevity of a subject with the disease or condition. Prophylactic treatment includes delaying the onset of a disease or condition in a subject at risk of developing the disease or condition or reducing the likelihood that a subject will then develop the disease or condition in a subject that is at risk for developing the disease or condition.

An embodiment of the invention includes administering an antimalarial compound disclosed herein or composition thereof in a combination therapy with one or more additional agents for the treatment of malaria. Agents for the treatment of malaria include quinine, atovaquone, chloroquine, cycloguanil, hydroxycholoroquine, amodiaquine, pyrimethamine, sulphadoxine, proguanil, mefloquine, halofantrine, pamaquine, primaquine, artemesinin, artemether, artesunate, artenimol, lumefantrine, dihydroartemisinin, piperaquine, artether, doxycycline and clindamycin.

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Additionally, the compounds of the present invention can be administered intranasally or transdermally. It will be obvious to those skilled in the art that the following dosage forms may comprise as the active ingredient, either compounds or a corresponding pharmaceutically acceptable salt of a compound of the present invention.

For preparing pharmaceutical compositions from the compounds of the present invention, pharmaceutically acceptable carriers can either be solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material. In powders, the carrier is a finely divided solid which is in a mixture with the finely divided active ingredient.

In tablets, the active ingredient is mixed with the carrier having the necessary binding properties in suitable proportions and compacted in the shape and size desired.

The powders and tablets preferably contain from about one to about seventy percent of the active ingredient. Suitable carriers are magnesium carbonate, magnesium stearate, talc, sugar, lactose, pectin, dextrin, starch, gelatin, tragacanth, methylcellulose, sodium caboxymethylcellulose, a low-melting wax, cocoa butter, and the like. Tablets, powders, cachets, lozenges, fast-melt strips, capsules and pills can be used as solid dosage forms containing the active ingredient suitable for oral administration.

For preparing suppositories, a low-melting wax, such as a mixture of fatty acid glycerides or cocoa butter, is first-melted and the active ingredient is dispersed homogeneously therein, as by stirring. The molten homogeneous mixture is then poured into convenient sized molds, allowed to cool, and thereby to solidify.

Liquid form preparations include solutions, suspensions, retention enemas, and emulsions, for example, water or water propylene glycol solutions. For parenteral injection, liquid preparations can be formulated in solution in aqueous polyethylene glycol solution.

Aqueous solutions suitable for oral administration can be prepared by dissolving the active ingredient in water and adding suitable colorants, flavors, stabilizing, and thickening agents as desired. Aqueous suspensions for oral administration can be prepared by dispersing the finely divided active ingredient in water with viscous material, such as natural or synthetic gums, resins, methylcellulose, sodium carboxymethylcellulose, and other well-known suspending agents.

The pharmaceutical composition is preferably in unit dosage form. In such form, the composition is subdivided into unit doses containing appropriate quantities of the active ingredient. The unit dosage form can be a packaged preparation, the package containing discrete quantities of, for example, tablets, powders, and capsules in vials or ampules. Also, the unit dosage form can be a tablet, cachet, capsule, or lozenge itself, or it can be the appropriate amount of any of these in packaged form.

The dosages may be varied depending upon the requirements of the patient, the severity of the condition being treated, and the compound being employed. Determination of the proper dosage for a particular situation is within the skill in the art. Also, the pharmaceutical composition may contain, if desired, other compatible therapeutic agents.

Materials and Methods

DHODH Expression Plasmid Construction, Protein Expression, and Purification.

Type 2 DHODH enzymes, such as the human and *Plasmodium* isoforms, generally contain a transmembrane domain that aids with localization to the inner mitochondrial space [23, 24, 29, 30]. The recombinantly expressed DHODH variants described herein lack this N-terminal mitochondrial signal peptide as it is not a catalytically essential structural feature and its presence hinders solubility and expression [31]. The A/T-rich sequence and unusual codon usage of *Plasmodium* spp. often limits the utility of bacterial protein expression systems. Hence, the previously described pfDHODH-pRSET (GeneID: 3885966) codon-optimized, synthetic DNA construct [32] encoding amino acids 159-565 was subcloned into the pET101D vector (Invitrogen) in-frame with a C-terminal 6×-His tag. Full-length, codon optimized DNA encoding the pbDHODH and pvDHODH genes were donated by GlaxoSmithKline and subcloned into the pET101D expression vector in-frame with the C-terminal 6×His tag. To improve solubility, the *P. berghei* (GeneID: 3427844) and *P. vivax* (GeneID: 5475357) DHODH genes were truncated to include amino acids 132-518 and 160-573, respectively, based upon sequence alignment with pfD-HODH. hsDHODH (GeneID: 1723) was subcloned into the pET101D expression vector in an analogous manner to the *Plasmodium* isoforms from a previously described expression plasmid with the final construct encoding amino acids 30-396 [33]. Full-length scDHODH (GeneID: 853664) was amplified from genomic DNA and cloned directly into the pET101D expression vector in-frame with the C-terminal 6×His tag. The DHODH ORFs of all isoforms were sequenced in their entirety.

*E. coli* BL-21(DE3) cells (Invitrogen) containing either the pfDHODH, pvDHODH, pbDHODH, hsDHODH, or scD-HODH pET101D expression plasmid were grown in Terrific Broth with 100 μg/mL ampicillin at 30° C. Protein expression was induced at $OD_{600}$~0.8 with the addition of isopropyl-beta-D-thiogalactopyranoside to a final concentration of 100 μM, the cultures were grown overnight at 22° C. Cells were pelleted by centrifugation at 7,000×g at 4° C. and frozen at −20° C. for later use. All subsequent purification steps were performed at 4° C.

Bacterial pellets were thawed in lysis buffer (50 mM HEPES (pH 7.5), 500 mM NaCl, 40 mM Imidazole, 0.1% Triton X-100) supplemented with Complete EDTA-free Protease Inhibitor Cocktail Tablets (Roche Applied Science). The cells were lysed by sonication and clarified by centrifugation at 48,000×g for 20 min. The supernatant was applied to a low-pressure column of Ni-NTA resin (Invitrogen) pre-equilibrated in buffer A (50 mM HEPES (pH 7.5), 500 mM NaCl, 40 mM Imidazole, 0.1% Triton X-100, 5 mM 2-mercaptoethanol). The column was washed with Buffer A until the $A_{280}$ reached a stable baseline; bound DHODH was eluted with Buffer B (50 mM HEPES (pH 7.5), 500 mM NaCl, 400 mM Imidazole, 0.1% Triton X-100, 5 mM 2-mercaptoethanol). The eluted protein was serially dialyzed against Buffer C (50 mM HEPES (pH 7.5), 150 mM NaCl, 10% Glycerol, 0.1% Triton X-100). Purity was assessed by SDS-PAGE and found to be greater than 85% for all DHODH isoforms. Total protein concentration was determined by Bradford analysis. DHODH requires a bound FMN cofactor for catalysis and thus, the concentration of FMN is equal to the concentration of active protein [25, 34]. FMN concentration was measured spectrophotometrically at 445 nM ($\epsilon_{445}$=12.5 mM$^{-1}$ cm$^{1}$) by heat-denaturing the protein to release bound cofactor. Purified DHODH was aliquoted, flash-frozen in liquid $N_2$, and stored at −80° C. for later use.

Enzymatic Assays for DHODH Activity.

Type 2 DHODH activity was monitored with either the direct assay measuring the formation of orotate or via a chromogen reduction assay using DCIP. Although the extinction coefficient and absorption wavelength are preferable for the chromogen reduction assay, the inorganic electron acceptor DCIP can be utilized by DHODH as the final electron acceptor in lieu of $CoQ_n$ when the endogenous substrate is at a low concentration. As such, the direct assay was used to measure the binding affinity of pfDHODH to $CoQ_D$ and L-DHO. The enzymatic reaction was performed by varying the L-DHO concentration (1-400 μM) or $CoQ_D$ concentration (1-200 μM) while keeping the other substrate constant and in excess. The formation of orotate was measured continuously at 296 nm ($\epsilon_{296}$=4.3 mM$^{-1}$ cm$^{-1}$). Inhibition of DHODH by small molecules was evaluated using the chromogen based assay with a final substrate concentration of 200 μM L-DHO, 18 μM $CoQ_D$, and 100 μM DCIP, unless otherwise noted. The reduction of DCIP was monitored at 600 nm ($\epsilon_{600}$=18.8 mM$^{-1}$ cm$^{-1}$). Reactions using either assay were performed at 25° C. in Buffer C and initiated with the addition of enzyme to a final concentration of 5-50 nM.

Inhibitors of DHODH, as classified by the chromogen reduction assay, were also evaluated for activity using FeCy as an electron acceptor. A final concentration of 5-50 nM DHODH, 200 μM L-DHO and 100 μM FeCy in Buffer C was used in this assay. Both the reduction of FeCy and the formation of orotate was monitored at 420 nm ($\epsilon_{420}$=1 mM$^{-1}$ cm$^{-1}$) and 290 nm ($\epsilon_{280}$=2 mM$^{-1}$ cm$^{-1}$), respectively, noting that two molecules of FeCy are reduced for one molecule of L-DHO. As with the previous assays, the reaction was performed at 25° C. and initiated with the addition of enzyme.

Inhibition of the Type 1 DHODH from *S. cerevisiae* was measured using the DCIP assay described above for assaying Type 2 DHODH enzymes except that 115 μM fumarate was used in lieu of $CoQ_D$. The concentration of fumarate corresponds with the previously reported substrate $K_m$, the concentration of L-DHO is in slight excess [35].

Substrate specificity and enzyme inhibition data was analyzed with GraphPad Prism Version 4 for Windows (GraphPad Software). Kinetic constants were calculated by non-linear regression fitting of the data to the Michaelis-Menten equation [36]. $IC_{50}$ values were determined by non-linear regression fitting of the data to Equation 1:

$$v_i = \frac{v_0}{1 + \frac{[I]}{IC_{50}}} \quad \text{(Eq. 1)}$$

where $v_i$=maximum initial velocity of product formation in the presence of inhibitor, $v_0$=maximum initial velocity of product formation, I=concentration of inhibitor, and $IC_{50}$=half maximal inhibitory concentration.

HTS to Identify pfDHODH Inhibitors.

The chromogen reduction assay for pfDHODH activity was adapted for HTS in 384-well plates based upon previous studies [37]. The assay was performed in a final volume of 50 μL of 100 mM HEPES (pH 8.0), 150 mM NaCl, 5% Glycerol, 0.05% Triton X-100, 175 μM L-DHO, 11 μM decylubiquinone, 95 μM DCIP, and 10 nM pfDHODH. Compounds from the Genzyme Corporation Small Molecule Library, comprised of 208,000 diverse, largely commercially available molecules, were pin-transferred into the 384-well assay plates to give a final drug concentration of 10 μM for the initial screen. The reaction proceeded at room temperature for 20 min after which, $A_{600}$ was measured using an automated microplate reader. The quality of data from the final assay was assessed using a statistical measure described by Zhang et al. [38] where the Z-factor 0.6; a Z-factor between 0.5 and 1 is generally favorable for a HTS. Primary hits were defined as compounds that inhibited ≥70% of pfDHODH activity at the initial screening concentration of 10 These compounds were cherry-picked and re-tested at a concentration of 1 μM, com pounds that inhibit ≥50% of enzymatic activity were selected for IC$_{50}$ determination.

Re-Screening of Primary Hits from HTS.

IC$_{50}$ values, with respect to pfDHODH activity, for selected inhibitors were calculated using the aforementioned chromogen reduction assay with sixteen different drug concentrations and reagent concentrations of 200 μM L-DHO, 18 μM CoQ$_D$, and 100 μM DCIP. Compounds confirmed to inhibit pfDHODH activity were tested in an analogous manner for inhibition of hsDHODH, pvDHODH, pbDHODH, and scDHODH.

Inhibition of In Vitro *P. falciparum* Cultures.

*P. falciparum* strains D10, 3D7, HB3, and Dd2 were obtained from the Malaria Research and Reference Reagent Resource Center (Manassas, Va.). The parasite strains were maintained in vitro by method of Trager and Jensen [39]. The inhibition of *P. falciparum* growth in the presence of drug was assessed by the relative reduction of [$^3$H]-hypoxanthine uptake as previously described [40, 41]. Inhibition data were fitted to Equation 1 using non-linear regression analysis except that the relative velocity of parasite growth was substituted for the rate of product formation.

Transgenic parasites expressing scDHODH were generated as described by Painter et al. [28] except that full length scDHODH was cloned directly into the pGem3Z vector without a GFP tag. The resultant plasmid was transfected into ring stages of *P. falciparum* D10 by electroporation and maintained in culture using standard methods under the selection of WR99210.

EXEMPLIFICATION

Example 1

Synthesis of Compound 1 and Related Compounds

Two routes, exemplified in Scheme 1, can be used to synthesize Compound 1:

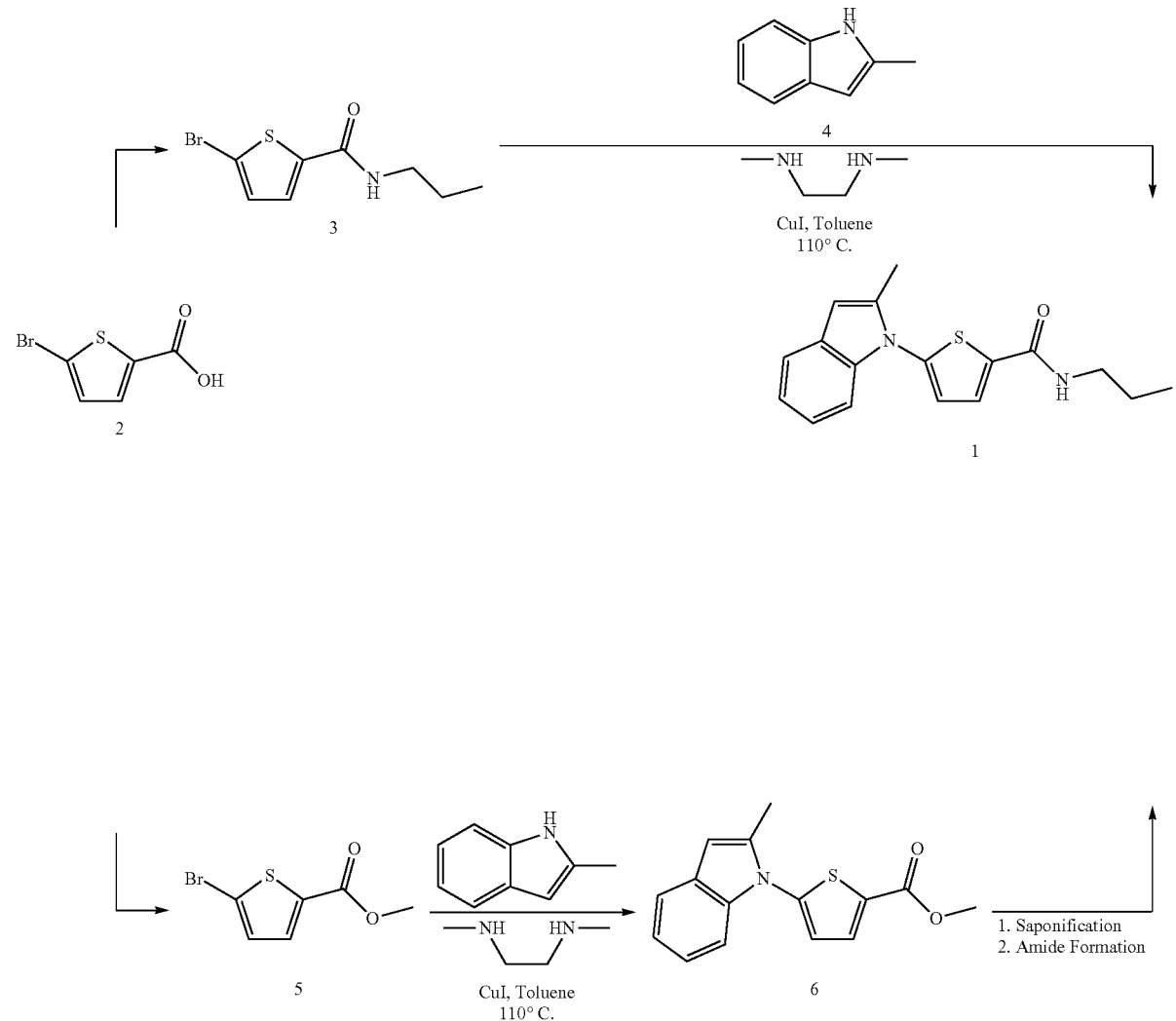

Synthetic Pathway 1

The synthesis relied on commercially available starting material, 2-bromo-5-carboxy-thiophene 2. One synthetic route commenced with formation of the amide 3 using standard amide coupling conditions. Introduction of the aryl amine moiety was achieved through metal-mediated coupling as described by Buchwald et al. to provide Compound 1 [42]. The procedure is exemplified employing dimethyl-diaminoethane as the ligand, although a variety of amine ligands have been described in the literature to affect this coupling. This synthetic scheme was followed to access a small library of analogs of Compound 1.

Synthetic Pathway 2

A second route to Compound 1 involved protecting the carboxylic acid 2 as its ester 5. Any suitable ester may be employed. Next, the amine functionality was introduced following the coupling procedure previously described to afford the protected amino thiophene 6. The ester was then saponified to afford the carboxylic acid which was subjected to standard amide coupling conditions to afford Compound 1.

Alternate Synthesis of Compound 1 and Related Compounds

A library of compounds was synthesized utilizing the following representative procedure:

To a microwave reactor vial, bromo-thiophene (1.0 equiv), CuI (20 mol %), Proline (40 mol %), and potassium carbonate (3.0 equiv) were added. DMSO (0.22M) was added and the vial evacuated with nitrogen. Amine (2.0 equiv) was then added and the vial was heated at 140° C. in a microwave reactor for 1 h. The reaction was cooled to room temperature and the reaction mixture was quenched by the addition of $H_2O$. The aqueous layer was extracted with EtOAc (3×). The combined organic layers were washed with brine and dried over $MgSO_4$ before they were concentrated in vacuo. The product was purified on silica gel running 0%→100 EtOAc/hexanes.

Compound 1

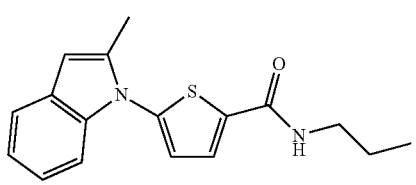 [SMILES: CCCNC(=O)c1ccc(-n2c(C)cc3ccccc32)s1]

5-(2-methyl-1H-indol-1-yl)-N-propylthiophene-2-carboxamide $^1$H NMR (CDCl$_3$, 400 MHz) δ 7.54-7.52 (m, 1H), 7.49 (d, 1H, J=4.0 Hz), 7.25-7.23 (m, 1H), 7.15-7.12 (m, 2H), 6.99 (d, 1H, J=4.0 Hz), 6.41 (s, 1H), 5.87 (br s, 1H), 4.44 (q, 2H, J=6.4 Hz), 2.36 (s, 3H), 1.69-1.64 (m, 2H), 1.00 (t, 3H, J=7.6 Hz)

Compound 5

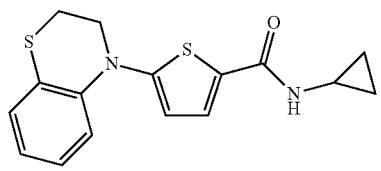 [SMILES: O=C(NC1CC1)c1ccc(N2CCSc3ccccc32)s1]

5(2H-benzo[b][1,4]thiazin-4(3H)-yl)-N-cyclopropylthiophene-2-carboxamide

MS m/z 316.9 (M+H)$^+$

Compound 7

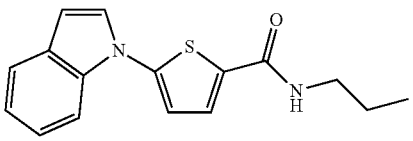 [SMILES: CCCNC(=O)c1ccc(-n2ccc3ccccc32)s1]

5-(1H-indol-1-yl)-N-propylthiophene-2-carboxamide $^1$H NMR (CDCl$_3$, 400 MHz) δ 7.69 (d, 1H, J=8.0 Hz), 7.65 (d, 1H, J=8.0 Hz), 7.42 (d, 1H, J=4.0 Hz), 7.30 (d, 1H, J=3.2 Hz), 7.30-7.27 (m, 1H), 7.22-7.19 (m, 1H), 7.03 (d, 1H, J=4.0 Hz), 6.69 (d, 1H, J=3.2 Hz), 5.95 (br s, 1H, 3.42 (q, 2H, J=6.4 Hz), 1.68-1.63 (m, 2H), 1.00 (t, 3H, J=7.6 Hz); MS m/z 299.2 (M+H)$^+$ Compound 8

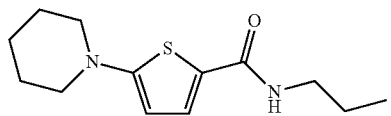 [SMILES: CCCNC(=O)c1ccc(N2CCCCC2)s1]

5-(piperidin-1-yl)-N-propylthiophene-2-carboxamide $^1$H NMR (CDCl$_3$, 400 MHz) δ 7.19 (d, 1H, J=4.4 Hz), 5.95 (d, 1H, J=4.4 Hz), 5.68 (br s, 1H), 3.34 (q, 2H, J=6.0 Hz), 3.19

(t, 4H, J=5.6 Hz), 1.72-1.66 (m, 4H), 1.61-1.56 (m, 4H), 0.95 (t, 3H, J=7.6 Hz); MS m/z 253.2 (M+H)⁺

Compound 9

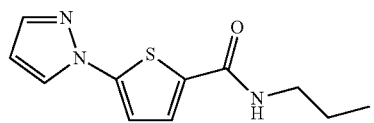 [SMILES: CCCNC(=O)c1ccc(-n2cccn2)s1]

N-propyl-5-(1H-pyrazol-1-yl)thiophene-2-carboxamide $^1$H NMR (CDCl$_3$, 400 MHz) δ 7.82 (d, 1H, J=2.8 Hz), 7.68 (d, 1H, J=1.2 Hz), 7.34 (d, 1H, J=4.0 Hz), 6.99 (d, 1H, J=4.0 Hz), 6.46 (dd, 1H, J=1.2, 2.8 Hz), 5.93 (Br s, 1H), 3.40 (q, 2H, J=7.2 Hz), 1.66-1.60 (m, 2H), 0.98 (t, 3H, J=7.6 Hz); MS m/z 236.1 (M+H)⁺

Compound 10

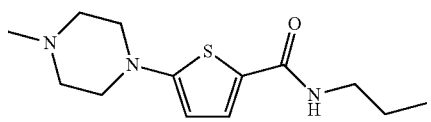 [SMILES: CCCNC(=O)c1ccc(N2CCN(C)CC2)s1]

5-(4-methylpiperazin-1-yl)-N-propylthiophene-2-carboxamide $^1$H NMR (CDCl$_3$, 400 MHz) δ 7.19 (d, 1H, J=4.4 Hz), 5.98 (d, 1H, J=4.4 Hz), 5.68 (br s, 1H), 3.35 (q, 2H, J=6.4 Hz), 3.23 (t, 4H, J=4.8 Hz), 2.54 (t, 4H, J=4.8 Hz), 2.33 (s, 3H), 1.62-1.56 (m, 2H), 0.95 (t, 3H, J=7.6 Hz); MS m/z 368.2 (M+H)⁺

Compound 11

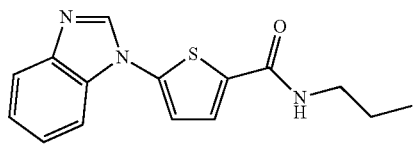 [SMILES: CCCNC(=O)c1ccc(-n2cnc3ccccc32)s1]

5-(1H-benzo[d]imidazol-1-yl)-N-propylthiophene-2-carboxamide $^1$H NMR (CDCl$_3$, 400 MHz) δ 8.09 (s, 3H), 7.86 (d, 1H, J=8.0 Hz), 7.63 (d, 1H, J=8.0 Hz), 7.46 (d, 1H, J=4.0 Hz), 7.39-7.36 (m, 2H), 7.12 (d, 1H, J=4.0 Hz), 5.60 (br s, 1H), 3.44 (q, 2H, J=6.4 Hz), 1.69-1.63 (m, 2H), 1.00 (t, 3H, J=7.6 Hz); MS m/z 286.1 (M+H)⁺

Compound 12

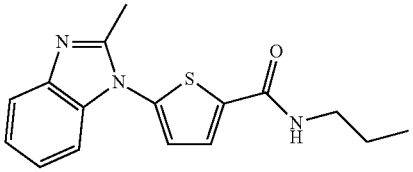 [SMILES: CCCNC(=O)c1ccc(-n2c(C)nc3ccccc32)s1]

5-(2-methyl-1H-benzo[d]imidazol-1-yl)-N-propylthiophene-2-carboxamide $^1$H NMR (CDCl$_3$, 400 MHz) δ 7.72 (d, 1H, J=8.0 Hz), 7.49 (d, 1H, J=4.0 Hz), 7.31-7.28 (m, 1H), 7.27-7.24 (m, 2H), 6.03 (br s, 1H), 3.45 (q, 2H, J=6.4 Hz), 2.57 (s, 3H), 1.70-1.64 (m, 2H), 1.01 (t, 3H, J=6.8 Hz); MS m/z 300.1 (M+H)⁺

Compound 13

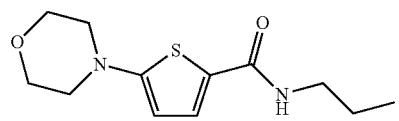 [SMILES: CCCNC(=O)c1ccc(N2CCOCC2)s1]

5-morpholino-N-propylthiophene-2-carboxamide $^1$H NMR (CDCl$_3$, 400 MHz) δ 7.20 (d, 1H, J=4.0 Hz), 6.02 (d, 1H, J=4.0 Hz), 5.72 (br s, 1H), 3.83 (t, 4H, J=4.8 Hz), 3.36 (q, 2H, J=6.0 Hz), 3.18 (t, 4H, J=4.8 Hz), 1.62-1.57 (m, 2H), 0.96 (t, 3H, J=7.6 Hz); MS m/z 255.1 (M+H)⁺

Compound 14

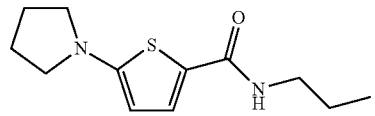 [SMILES: CCCNC(=O)c1ccc(N2CCCC2)s1]

N-propyl-5-(pyrrolidin-1-yl)thiophene-2-carboxamide $^1$H NMR (CDCl$_3$, 400 MHz) δ 7.20 (d, 1H, J=4.4 Hz), 5.65 (d, 1H, J=4.4 Hz), 5.63 (br s, 1H), 3.35 (q, 2H, J=6.8 Hz), 3.29

(t, 4H, J=6.84 Hz), 2.05-2.02 (m, 4H), 1.61-1.56 (m, 2H), 0.95 (t, 3H, J=7.6 Hz); MS m/z 239.2 (M+H)+

Compound 15

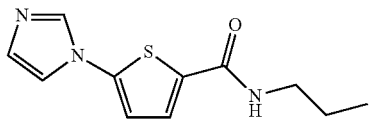

5-(1H-imidazol-1-yl)-N-propylthiophene-2-carboxamide

MS m/z 236.0 (M+H)+

Compound 16

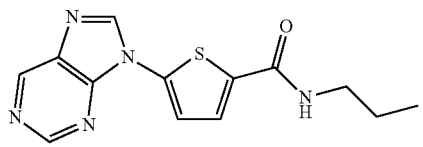 [SMILES: CCCNC(=O)c1ccc(-n2cnc3cncnc32)s1]

N-propyl-5-(9H-purin-9-yl)thiophene-2-carboxamide

MS m/z 287.9 (M+H)+

Compound 17

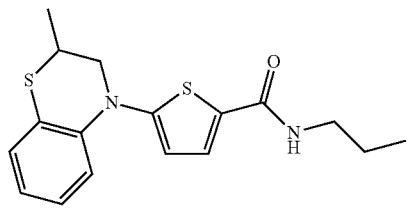 [SMILES: CCCNC(=O)c1ccc(N2CC(C)Sc3ccccc32)s1]

5-(2-methyl-2H-benzo[b][1,4]thiazin-4(3H)-yl)-N-propylthiophene-2-carboxamide

Compound 18

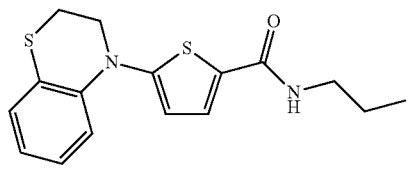 [SMILES: CCCNC(=O)c1ccc(N2CCSc3ccccc32)s1]

5-(2H-benzo[b][1,4]thiazin-4(3H)-yl)-N-propylthiophene-2-carboxamide

MS m/z 318.8 (M+H)+

Compound 19

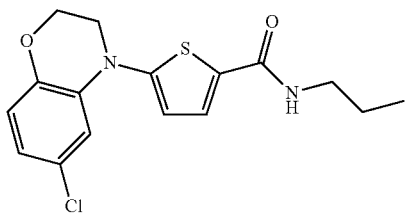 [SMILES: CCCNC(=O)c1ccc(N2CCOc3ccc(Cl)cc32)s1]

5-(6-chloro-2H-benzo[b][1,4]oxazin-4(3H)-yl)-N-propylthiophene-2-carboxamide

MS m/z 336.8 (M+H)+

Compound 20

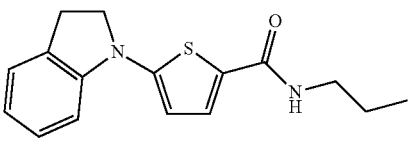 [SMILES: CCCNC(=O)c1ccc(N2CCc3ccccc32)s1]

5-(indolin-1-yl)-N-propylthiophene-2-carboxamide

MS m/z 286.9 (M+H)+

Compound 21

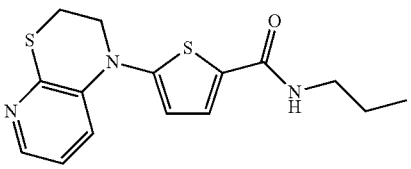 [SMILES: CCCNC(=O)c1ccc(N2CCSc3ncccc32)s1]

5-(2,3-dihydro-1H-pyrido[2,3-b][1,4]thiazin-1-yl)-N-propylthiophene-2-carboxamide MS m/z 319.8 (M+H)+

Compound 22

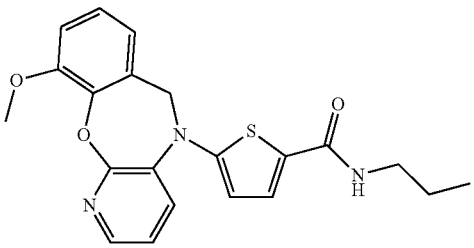 [SMILES: CCCNC(=O)c1ccc(N2Cc3cccc(OC)c3Oc3ncccc32)s1]

5-(10-methoxybenzo[f]pyrido[2,3-b][1,4]oxazepin-5(6H)-yl)-N-propylthiophene-2-carboxamide MS m/z 395.8 (M+H)+

Preparation of Benzimidazole Thiophene Carboxamides (VII)

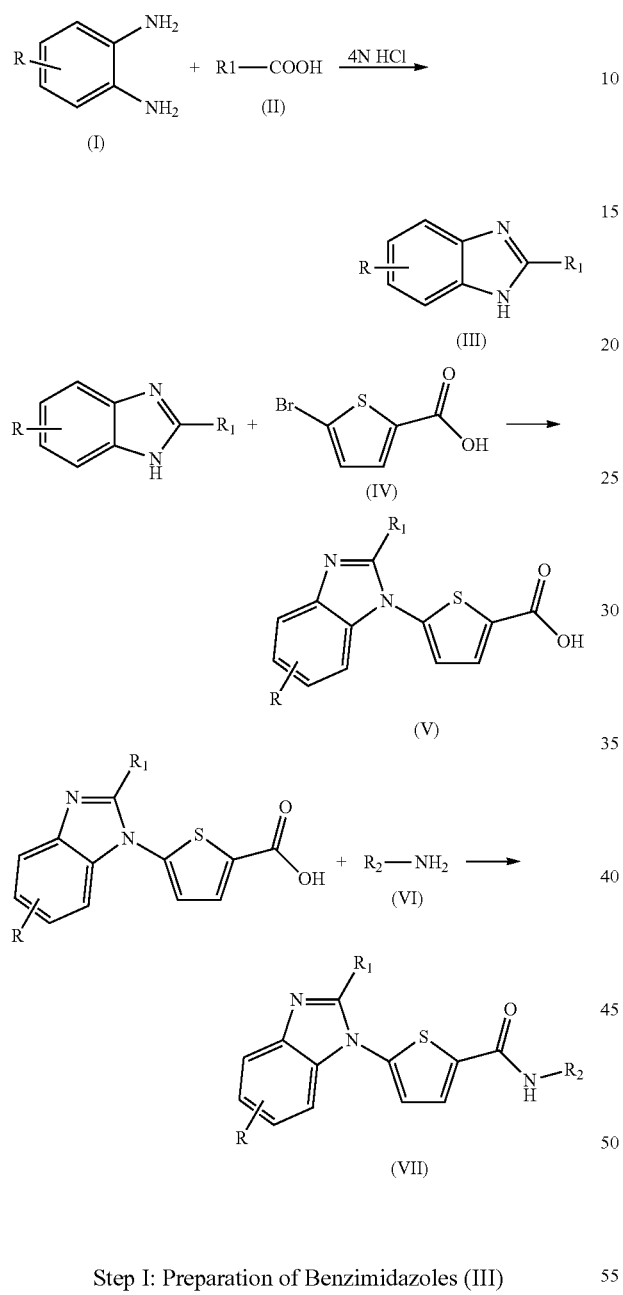

Step I: Preparation of Benzimidazoles (III)

A solution of 4 (3)-substituted-o-phenylenediamines (100 mmol) and organic acid (150 mmol) in 4N HCl (10 volumes) was refluxed for 24 h. After completion the reaction was cooled, charcoal was added and filtered over a celite bed. The filtrate was basified with aq. ammonia solution till the pH~10-12. Extracted the basified reaction with ethyl acetate (250 ml×3), dried the ethyl acetate layer with sodium sulphate and distilled off the solvent completely to residue. To the residue hexane (50 ml) was added and filtered to get the desired compound (III).

TABLE 1-continued benzimidazoles (III):

| Benzimidazole | Yield % |
|---|---|
| 5-fluoro-1H-benzimidazole | 69.76 |
| 4,2-dimethyl-1H-benzimidazole | 28.5 |
| 5-fluoro-2-methyl-1H-benzimidazole | 33.60 |

Step II: Preparation of Benzimidazole Thiophene Carboxylic Acid (V)

Charged benzimidazole (III) (28.98 mmoles), cesium carbonate (33.81 mmoles), cuprous oxide (0.918 mmoles), 2-amino-4,6-dihydroxypyrimidine (3.62 mmoles), PEG (28.98 mmoles), 5-bromo-thiophen-2-carboxylic acid (IV) (24.15 mmoles) and NMP (10 ml) to the 100 ml RB flask fitted with thermo well and condenser. The reaction mixture was heated to 160° C. and maintained for 18-20 hrs. After completion of reaction, cooled the reaction to room temperature, added water (100 ml) and adjusted the pH to ~4.5-5 using formic acid. Filtered off the precipitated solid and washed with water (2×25 ml). The solid was then dissolved in methanol (250 ml), filtered through a celite bed, distilled of the solvent completely under reduced pressure. To the residue IPA (25 ml) was added to precipitate the product, stirred for 30 min, filtered and dried to get the compound (V).

TABLE 2 benzimidazole thiophene carboxylic acids (V):

| Compound | Yield % |
|---|---|
| benzimidazole-thiophene carboxylic acid | 42 |
| 2-methyl-benzimidazole-thiophene carboxylic acid | 56.80 |
| 6-chloro-benzimidazole-thiophene carboxylic acid | 74.7 |
| 2-methyl-6-chloro-benzimidazole-thiophene carboxylic acid | 59.7 |
| 2-methyl-6-fluoro-benzimidazole-thiophene carboxylic acid | 33.60 |
| 6-methyl-benzimidazole-thiophene carboxylic acid | 81.4 |
| 2,6-dimethyl-benzimidazole-thiophene carboxylic acid | 79.7 |

Step III: Preparation of Benzimidazole Thiophene Carboxamides (VII)

A solution of amine (VI) (0.74 mmoles) in DCM (50 ml) was added to a stirred and cooled (0° C.) solution of benzimidazole thiophenecarboxylic acid (V) in DCM (200 ml) and the mixture was stirred for 5 min. To the above mass HOBt (0.25 .moles) and N-methylmorpholine (0.74 mmoles) were added and stirred for 30 min. After 30 min., EDC.HCl (0.74 mmoles) was added and stirred for 3 h at 0° C. and then at room temperature for 10 h. After completion of reaction, water (50 ml) was added and separated the organic layer, which was washed with sodium bicarbonate solution and brine solution, and dried over $Na_2SO_4$. Distilled off the solvent completely under reduced pressure to get the crude product, the crude compound is then purified by using silica gel 60-120 mesh column chromatography and DCM: MeOH 100-5% as mobile phase and by using preparative HPLC methods to get the pure compound.

TABLE 3 benzimidazole thiophene carboxamides (VII):

| Compound. | Yield % | [M − H]+ | 1H NMR |
|---|---|---|---|
| 23 | 27 | 284.3 | 1H (400 MHz, CDCl3) δ 8.09(s, 1H), 7.85-7.87(m, 1H), 7.62-7.65(m, 1H), 7.43(d, J = 4.4 Hz, 1H), 7.35-7.41(m, 2H), 7.12(d, J = 4.4 Hz, 1H), 6.15(m, 1H), 2.89-2.93(m, 1H), 0.88-0.83(m, 2H), 0.65-0.69(m, 2H). |
| 24 | 25 | 258.4 | 1H (400 MHz, CDCl3) δ 8.10(s, 1H), 7.85-7.88(m, 1H), 7.63-7.65(m, 1H), 7.46(d, J = 4.4 Hz, 1H), 7.35-7.42(m, 2H), 7.12(d, J = 4.4 Hz, 1H), 6.07 (m, 1H), 3.05(d, J = 5.2 Hz, 3H) |
| 25 | 72 | 272.1 | 1H (400 MHz, CDCl3) δ 8.09(s, 1H), 7.84-7.88(m, 1H), 7.61-7.65(m, 1H), 7.47(d, J = 4.4 Hz, 1H), 7.35-7.41(m, 2H), 7.12(d, J = 4.4 Hz, 1H), 6.18(brs, 1H), 3.48-3.55(m, 2H), 1.28(t, J = 7.2 Hz, 3H) |
| 27 | 25 | 272.4 | 1H (400 MHz, CDCl3) δ 8.10(s, 1H), 7.85-7.87(m, 1H), 7.64-7.66(m, 1H), 7.36(d, J = 4.4 Hz, 1H), 7.35-7.41(m, 2H), 7.11(d, J = 4.4 Hz, 1H), 3.25(s, 6H) |
| 26 | 22 | 298.5 | 1H (400 MHz, CDCl3) δ 8.11(s, 1H), 7.85-7.87(m, 1H), 7.65-7.68(m, 1H), 7.49(d, J = 4.4 Hz, 1H), 7.35-7.41(m, 2H), 7.14(d, J = 4.4 Hz, 1H), 3.71-3.83(m, 4H), 1.98-2.07 (m, 4H) |
| 30 | 34 | 288.3 | 1H (400 MHz, CDCl3) δ 8.10(s, 1H), 7.86-7.88(m, 1H), 7.62-7.67(m, 1H), 7.49(d, J = 4.4 Hz, 1H), 7.35-7.42(m, 2H), 7.14(d, J = 4.4 Hz, 1H), 3.86-3.89 (m, 2H), 3.64-3.68(m, 2H) |
| 35 | 80 | 312.0 | 1H (400 MHz, d6-DMSO) δ 8.64(s, 1H), 8.49(d, J = 7.6 Hz, 1H), 7.74-7.81(d, J = 4.4, 1H), 7.46(d, J = 4.4 Hz, 1H), 7.34-7.43(m, 2H), 4.18-4.23(m, 1H), 1.91 (m, 1H), 1.71(m, 2H), 1.50(m, 4H). |
| 36 | 76.9 | 286.1 | 1H (400 MHz, d6-DMSO) δ 8.62(s, 1H), 8.43(d, J = 7.6 Hz, 1H), 7.73-7.79(m, 2H), 7.46(d, J = 4.4 Hz, 1H), 7.33-7.42(m, 2H), 4.04-4.09(m, 1H), 1.18(d, J = 6.8 Hz, 6H). |
| 37 | 73 | 300.1 | 1H (400 MHz, d6-DMSO) δ 8.62(s,, 1H), 8.35(d, J = 7.6 Hz, 1H), 7.87(d, J = 7.4, 1H), 7.73-7.86(m, 2H), 7.46(d, J = 4.4 Hz, 1H), 7.33-7.45(m, 2H), 3.87-3.91(m, 1H), 1.48-1.56(m, 2H), 1.14(d, j = 6.4 Hz, 3H), 0.88(t, J = 7.2 Hz, 3H). |
| 38 | 74 | 298.0 | 1H (400 MHz, d6-DMSO) δ 8.82(d, J = 7.6 Hz, 1H), 8.64(s, 1H), 7.86(d, J = 4.4 Hz, 1H), 7.74-7.81(m, 2H), 7.486-7.67(m, 1H), (d, J = 4.4 Hz, 1H), 7.34-7.43(m, 2H), 4.38-4.42(m, 1H), 2.03-2.28(m, 4H), 1.64-1.73(m, 2H). |
| 46 | 69 | 284.1 | 1H (400 MHz, CDCl3) δ 8.11(brs, 1H), 7.86-7.88(m, 1H), 7.66-7.67(m, 1H), 7.43(d, J = 4.4 Hz, 1H), 7.35-7.40(m, 2H), 7.15(d, J = 4.4 Hz, 1H), 4.28-4.55(m, 4H), 2.42-2.50(m, 2H). |
| 47 | 73 | 300.1 | 1H (400 MHz, CDCl3) δ 8.11(brs, 1H), 7.86-7.88(m, 1H), 7.64-7.66(m, 1H), 7.46(d, J = 4.4 Hz, 1H), 7.36-7.41(m, 2H), 7.13(d, J = 4.4 Hz, 1H), 5.89(m, 1H), 4.09-4.16(m, 1H), 1.57-1.64(m, 2H), 1.27(d, j = 6.4 Hz, 3H), 0.99(t, J = 7.2 Hz, 3H). |
| 34 | 58.8 | 312.0 | 1H (400 MHz, d6-DMSO) δ 8.63(s, 1H), 7.80(d, J = 4.4 Hz, 1H), 7.73(d, J = 4.4, 1H), 7.34-7.48(m, 4H), 3.66(m, 4H), 1.58-1.66(m, 6H). |
| 28 | 70.2 | 244.4 | 1H (400 MHz, CDCl3) δ 8.63(s, 1H), 7.83(d, J = 4.4 Hz, 1H), 7.80(d, J = 7.6 Hz, 1H), 7.76(d, J = 7.6 Hz, 1H), 7.58 & 8.16 (brs, 2H), 7.47(d, J = 4.4 Hz, 1H), 7.34-7.43(m, 2H) |
| 29 | 56.0 | 300.4 | 1H (400 MHz, CDCl3) δ 8.09(s, 1H), 7.85-7.87(m, 1H), 7.62-7.65(m, 1H), 7.46(d, J = 4.4 Hz, 1H), 7.35-7.45(m, 2H), 7.12(d, J = 4.4 Hz, 1H), 6.07(brs, 1H), 3.48(t, J = 7.2 Hz, 2H)1.59-1.66 (m, 2H), 1.38-1.48(m, 2H), 0.97(t, J = 7.2 Hz, 3H) |
| 31 | 56.8 | 298.0 | 1H (400 MHz, d6-DMSO) δ 8.70(d, J = 3.6 Hz, 1H), 7.80(d, J = 4.4 Hz, 1H), 7.62-7.64(m, 1H), 7.37(d, J = 4.4 Hz, 1H), 7.25-7.36(m, 3H), 2.79-2.84(m, 1H), 0.71-0.76(m, 2H), 0.58-0.62(m, 2H). |
| 33 | 73.9 | 286.0 | 1H (400 MHz, d6-DMSO) δ 8.72(m, 1H), 7.83(d, J = 4.4 Hz, 1H), 7.62-7.82(m, 1H), 7.38(d, J = 4.4 Hz, 1H), 7.24-7.31(m, 3H), 3.27-3.32(m, 2H), 1.15(t, J = 7.2 Hz, 3H). |
| 55 | 74.7 | 318.1 | 1H (400 MHz, d6-DMSO) δ 8.70(m, 1H), 8.68(s, 1H), 7.68-7.88(m, 3H), 7.44-7.48(m, 1H), 7.37-7.41(m, 1H), 2.81(m, 1H), 0.93(m, 2H), 0.7.36(m, 2H). |

TABLE 3-continued benzimidazole thiophene carboxamides (VII):

| Compound. | Yield % | [M − H]+ | 1H NMR |
|---|---|---|---|
| 54 | 27.0 | 306.1 | 1H (400 MHz, d6-DMSO) δ 8.72(m, 1H), 8.68(s, 1H), 7.75-7.81(m, 3H), 7.45-7.51(m, 1H), 7.38-7.44(m, 1H), 3.26-3.31m, 2H), 1.14(t, J = 7.2 Hz, 3H). |
| 56 | 38.0 | 320.1 | 1H (400 MHz, d6-DMSO) δ 8.369-8.71(m, 1H), 8.68(s, 1H), 7.83(d, J = 4.4 Hz, 1H), 7.80-7.82(m, 1H), 7.75(d, J = 4.4 Hz, 1H), 7.48-7.51(m, 1H), 7.38-7.44(m, 1H), 3.21-3.25(m, 2H), 1.52-1.58(m, 2H), 0.89-0.94(1, J = 7.2 Hz, 3H). |
| 40 | 59.7 | 332.0 | 1H (400 MHz, CDCl3) δ 7.61-7.63(m, 1H), 7.46(d, J = 4.4 Hz, 1H), 7.14-7.23(m, 2H), 7.06(d, J = 4.4 Hz, 1H), 6.16(brs, 1H), 2.90-2.91(m, 1H), 2.55(s, 3H), 0.89(m, 2H), 0.68(m, 2H). |
| 52 | 20.5 | 320.1 | 1H (400 MHz, d6-DMSO) δ 8.72(m, 1H), 7.85-(d, J = 4.4 Hz, 1H), 7.71(m, 1H), 7.42(d, J = 4.4 Hz, 1H), 7.26-7.33(m, 2H), 3.25-3.30(m, 2H), 1.13(t, J = 7.2 Hz, 3H). |
| 51 | 30.0 | 334.1 | 1H (400 MHz, d6-DMSO) δ 8.70(m, 1H), 7.84(d, J = 4.4 Hz, 1H), 7.71(m, 1H), 7.41(d, J = 4.4 Hz, 1H) 7.26-7.33(m, 2H), 3.20-3.25(m, 2H), 2.48(s, 3H), 1.52-1.571(m, 2H), 0.91(t, J = 7.2 Hz, 3H). |
| 42 | 33.6 | 316.1 | 1H (400 MHz, CDCl3) δ 7.64(d, J = 4.4 Hz, 1H), 7.14-7.46(3m, 1H), 7.13(d, J = 4.4 Hz, 1H), 7.01-7.06(m, 1H), 6.92-6.99(m, 1H), 6.16(brs, 1H), 2.88-2.92(m, 1H), 2.54(s, 3H), 0.89(m, 2H), 0.68(m, 2H). |
| 53 | 15.2 | 304.1 | 1H (400 MHz, d6-DMSO) δ 8.74(m, 1H), 7.82-(d, J = 4.4 Hz, 1H), 7.41(d, J = 4.4 Hz, 1H) 7.29-7.66(3m, 1H), 7.09-7.14(m, 1H), 3.29-3.32(m, 2H), 2.47(m, 3H), 1.14(t, J = 7.2 Hz, 3H). |
| 50 | 14.7 | 318.1 | 1H (400 MHz, d6-DMSO) δ 8.70(t, 1H), 7.84(d, J = 4.4 Hz, 1H), 7.41(d, J = 4.4 Hz, 1H), 7.29(d, J = 4.4 Hz, 1H), 7.08-7.13(m, 2H), 3.21-3.27(m, 2H), 2.47(s, 3H), 1.51-1.601(m, 2H), 0.91(t, J = 7.2 Hz, 3H). |
| 60 | 81.4 | 298.1 | 1H (400 MHz, d6-DMSO) δ 8.66(m, 1H), 8.54(s, 1H), 7.77(m, 1H), 7.65(m, 1H), 7.43(m, 1H), 7.24(d, J = 4.4 Hz, 1H), 7.16(d, J = 4.4 Hz, 1H), 2.81(m, 1H), 2.47(s, 3H), 0.72(m, 2H), 0.59(m, 2H). |
| 61 | 25.3 | 286.1 | 1H (400 MHz, d6-DMSO) δ 8.68(m, 1H), 8.53(s, 1H), 7.79(m, 1H), 7.64(m, 1H), 7.43(m, 1H), 7.22(d, J = 4.4 Hz, 1H), 7.16(d, J = 4.4 Hz, 1H), 3.26-3.32(m, 2H), 2.45(s, 3H), 1.14(t, J = 7.2 Hz, 3H). |
| 44 | 79.7 | 312.1 | 1H (400 MHz, d6-DMSO) δ 8.71(brs, 1H), 7.80(d, J = 4.4 Hz, 1H), 7.68-7.41 (m, 1H), 7.49(d, J = 4.4 Hz, 1H), 7.20-7.36(m, 1H), 7.20-7.36(m, 1H), 7.06-7.18(m, 2H), 2.78-2.83(m, 1H), 2.46(s, 3H), 2.29(s, 3H), 0.71-0.76(m, 2H), 0.57-0.76(m, 2H). |
| 62 | 45.5 | 300.1 | 1H (400 MHz, d6-DMSO) δ 8.69(m, 1H), 7.80(m, 1H), 7.48(d, J = 4.4 Hz, 1H), 7.34(m, 1H), 7.18(d, J = 4.4 Hz, 1H), 7.042-708(m, 2H), 3.27-3.30(m, 2H), 2.44(s, 3H), 2.37(s, 3H), 1.13(t, J = 7.2 Hz, 3H). |

Preparation of Benzimidazole Thiophene Carboxamides (VII)

Scheme 2:

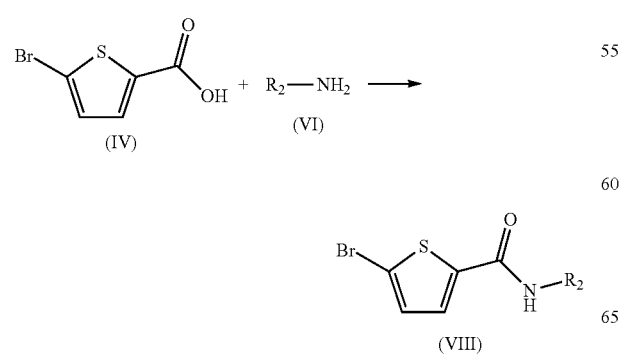

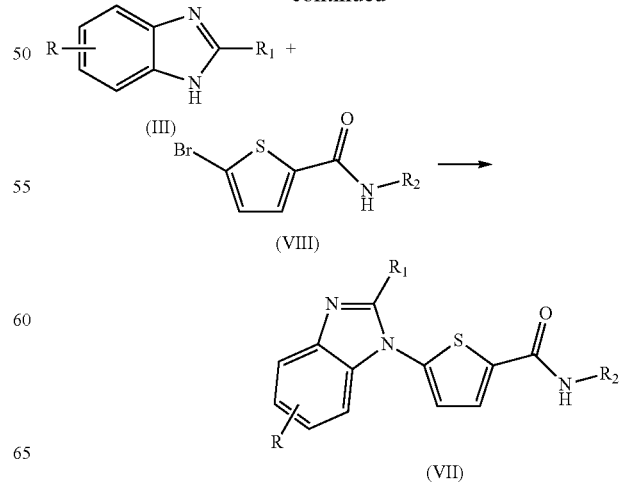

Step I: Preparation of Thiophenecarboxamides (VIII)

A solution of amine (VI) (28.98 mmoles) in DCM (200 ml) was added to a stirred and cooled (0° C.) solution of 5-bromo-2-thiophenecarboxylic acid (IV) (24.15 mmoles) in DCM (250 ml) and the mixture was stirred for 5 min. To the above mass HOBt (9.66 mmoles) and N-methylmorpholine (28.98 mmoles) were added and stirred for 30 min at 0-5° C. After 30 minutes EDC.HCl (28.98 mmoles) was added and stirred for 3 h at 0° C. and then at room temperature for 10 h. The mixture was diluted with water (100 ml) and organic layer was separated. The organic layer was washed with sodium bicarbonate solution and brine solution, dried over $Na_2SO_4$, distillation of solvent completely under reduced pressure to residue. To the residue hexane (50 ml) added and stirred for 30 min, filtered to get the desired compound (VIII).

TABLE 4 thiophenecarboxamides (VIII):

| $R_2$ | Yield % |
|---|---|
| Ethyl | 67.8 |
| propyl | 66.7 |
| cyclopropyl | 81.0 |

Step II: Preparation of Benzimidazole Thiophene Carboxamides (VII)

Charged benzimidazole (III) (5.115 mmoles), 2-bromo-thiophene-2-carboxamide (VIII) (3.938 mmoles), cesium carbonate (7.161 mmoles), cuprous oxide (0.307 mmoles), 4,7-dimethoxy-1,10-phenathroline (0.716 mmoles), PEG (5.115 mmoles) and DMSO to the RB flask fitted with thermo well and condenser. The reaction was heated to 110-115° C. under magnetic stirring for 24 hours. After completion of reaction cooled to room temperature, dichloromethane (500 ml) added and filtered through a celite bed, washed the bed with dichloromethane (100 ml×2), distilled off the solvent completely under reduced pressure. Aq. ammonia (10 ml) was added to the residue and extracted with ethyl acetate (250 ml×3).

Dry the ethyl acetate layer with sodium sulfate, distilled completely to get the crude compound. The crude compound is then purified by using silica gel 60-120 mesh column chromatography and DCM: MeOH 100-5% as mobile phase to get the pure compound. (Some compounds are isolated by preparative HPLC purification method.

TABLE 5 benzimidazole thiophenecarboxamides (VII)

| Compound | Yield % | [M − H]$^+$ | $^1$H NMR |
|---|---|---|---|
| 49 | 21.0 | 312.1 | $^1$H (400 MHz, CDCl3) δ 8.70(m, 1H), 7.81(d, J = 4.4 Hz, 1H), 7.65-7.67(m, 1H), 7.38(d, J = 4.4 Hz, 1H), 7.25(m, 3H), 2.79-2.84(m, 3H), 1.27(t, J = 7.2 Hz, 3H), 0.73(m, 2H), 0.60(m, 2H). |
| 63 | 1.83 | 300.1 | $^1$H (400 MHz, d$_6$-DMSO) δ 8.72(m, 1H), 7.80(d, J = 4.4 Hz, 1H), 7.64-7.66(m, 1H), 7.39(d, J = 4.4 Hz, 1H) 7.24-7.25(m, 3H), 3.25-3.30(m, 2H), 2.77-2.83(q, J = 7.2 Hz, 2H), 1.23(t, J = 7.2 Hz, 3H), 1.14(t, J = 7.2 Hz, 3H). |
| 67 | 1.4 | 326.1 | $^1$H (400 MHz, d$_6$-DMSO) δ 8.71(d, J = 3.6 Hz, 1H), 7.81(t, J = 4.4 Hz, 1H) 7.65-7.67(m, 1H), 7.37(t, J = 4.4 Hz, 1H), 7.15-7.28(m, 3H), 2.76-2.84(m, 3H), 1.69-1.78(m, 2H), 0.92(t, J = 7.2 Hz, 3H), 0.71-0.76(m, 2H), 0.58-0.61(m, 2H). |
| 59 | 2.0 | 314.1 | $^1$H (400 MHz, d$_6$-DMSO) δ 8.73(m, 1H), 7.82(d, J = 4.4 Hz, 1H), 7.65-7.66(m, 1H), 7.39(d, J = 4.4 Hz, 1H), 7.25(m, 3H), 3.26-3.39(m, 2H), 2.77(t, J = 7.6 Hz, 3H), 1.71-1.78(m, 2H), 1.14(t, J = 7.2 HZ, 3H), 0.91(t, J = 7.2 Hz, 3H), |
| 66 | 12.1 | 330.1 | $^1$H (400 MHz, d$_6$-DMSO) δ 8.70(d, J = 3.6 Hz, 1H), 7.80(d, J = 4.4 Hz, 1H), 7.40(d, J = 4.4 Hz, 1H), 7.25-7.69(3m, 1H), 7.07-7.13(m, 2H), 2.772-2.83(m, 3H), 1.26(t, J=7.2 Hz, 3H), 0.71-0.76(m, 2H), 0.58-0.61(m, 2H). |
| 69 | 1.51 | 318.1 | $^1$H (400 MHz, d$_6$-DMSO) δ 8.71(t, J = 5.6 Hz, 1H), 7.81(d, J = 4.4 Hz, 1H) 7.40(d, J = 4.4 Hz, 1H), 7.25-7.68(3m, 1H), 7.70-7.13(m, 1H), 3.26-3.31(m, 2H), 2.76-2.83(m, 2H), 1.25(t, J = 7.2 Hz, 3H), 1.14(t, J = 7.2 Hz, 3H). |
| 70 | 3.5 | 302.1 | $^1$H (400 MHz, d$_6$-DMSO) δ 8.66-8.69(m, 1H), 8.63(s, 1H), 7.78-7.83(d, J = 4.4 Hz, 1H), 7.46(d, J = 4.4 Hz, 1H) 7.20-7.29(m, 1H), 2.80-2.83(m, 1H), 0.71-0.74(m, 2H), 0.59-0.64(m, 2H). |
| 68 | 6.5 | 290.1 | $^1$H (400 MHz, d$_6$-DMSO) δ 8.64(d, J = 3.6 Hz, 1H), 8.59(s, 1H), 7.79(m, 1H), 7.76(d, J = 4.4 Hz, 1H) 7.49-7.72(3m, 1H), 7.44(d, J = 4.4 Hz, 1H), 7.16-7.26(m, 1H), 3.23-3.35(m, 2H), 1.11(t, J = 7.2 Hz, 3H). |
| 39 | 15.2 | 328.1 | $^1$H (400 MHz, CDCl3) δ 6.86-7.71(m, 5H), 6.47(brs, 1H), 3.86(s, 1H), 2.90(m, 1H), 2.54(s, 3H), 0.89(m, 2H), 0.68(m, 2H). |
| 57 | 3.2 | 382.1 | $^1$H (400 MHz, d$_6$-DMSO) δ 8.75(d, J = 3.6 Hz, 1H), 7.83(d, J = 4.4 Hz, 1H), 7.74-7.77(m, 1H), 7.44(d, J = 4.4 Hz, 1H), 7.27-7.29(m, 2H), 2.82-2.84(m, 1H), 2.48(s, 3H), 0.73-.0.76(m, 2H), 0.61-0.62(m, 2H) |

TABLE 5-continued benzimidazole thiophenecarboxamides (VII)

| Compound | Yield % | [M − H]+ | 1H NMR |
|---|---|---|---|
| 58 | 3.5 | 382.1 | 1H (400 MHz, d6-DMSO) δ 8.75(d, J = 3.6 Hz, 1H), 7.84(d, J = 4.4 Hz, 1H), 7.68(m, 1H), 7.44(d, J = 4.4 Hz, 1H), 7.39(m, 1H), 7.26-7.28(m, 1H), 2.82-2.84(m, 1H), 2.48(s, 3H), 0.76(m, 2H), 0.61(m, 2H) |
| 64 | 15.8 | 366.1 | 1H (400 MHz, d6-DMSO) δ 8.71(m, 1H), 7.43-7.97(m, 5H), 2.80-2.85(m, 1H), 2.54(s, 3H), 0.72-0.76(m, 2H), 0.58-0.61(m, 2H). |
| 60 | 32.0 | 398.1 | 1H (400 MHz, d6-DMSO) δ 8.66(m, 1H), 8.54(s, 1H), 7.77(m, 1H), 7.65(m, 1H), 7.43(m, 1H), 7.24(d, J = 4.4 Hz, 1H), 7.16(d, J = 4.4 Hz, 1H), 2.81(m, 1H), 2.47(s, 3H), 0.72(m, 2H), 0.59(m, 2H). |
| 61 | 36.0 | 286.1 | 1H (400 MHz, d6-DMSO) δ 8.68(m, 1H), 8.53(s, 1H), 7.79(m, 1H), 7.64(m, 1H), 7.43(m, 1H), 7.22(d, J = 4.4 Hz, 1H), 7.16(d, J = 4.4 Hz, 1H), 3.26-3.32(m, 2H), 2.45(s, 3H), 1.14(t, J = 7.2 Hz, 3H). |
| 65 | 26.3 | 312.0 | 1H (400 MHz, d6-DMSO) δ 8.69(d, J = 3.6 Hz, 1H), 7.81(d, J = 4.4 Hz, 1H), 7.05-7.15(m, 3H), 2.80-2.83(m, 1H), 2.54(s, 3H), 0.71-0.76(m, 2H), 0.58-0.62(m, 2H), |

Preparation of N-cyclopropyl-4-(2-methyl-1H-benzo[d]imidazol-1-yl)thiophene-3-carboxamide, Compound 77

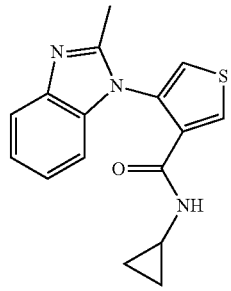 [SMILES: Cc1nc2ccccc2n1-c1cscc1C(=O)NC1CC1]

The compound has been prepared by using the method 2 and 4-bromo-N-cyclopropylthiophene-3-carboxamide.

Yield: 36.0%, M/Z [M−H]+1=298.1. 1H NMR data: 1H (400 MHz, d6-DMSO) δ 8.37 (m, 1H), 8.36 (d, J=4.4 Hz, 1H), 7.94 (d, J=4.4 Hz, 1H), 7.56 (m, 1H), 7.10-7.18 (m 2), 6.93 (m, 1H), 3.49 (m, 1H), 2.32 (s, 3H), 0.47-0.59 (m, 2H), 0.25-0.039 (m, 2H).

Preparation of N-cyclopropyl-5-(2-methyl-1H-benzo[d]imidazol-1-yl)thiophene-3-carboxamide, Compound 78

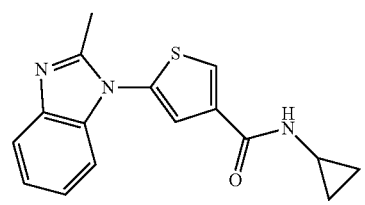 [SMILES: Cc1nc2ccccc2n1-c1cc(C(=O)NC2CC2)cs1]

By the method 1, and using 5-bromothiophene-3-carboxylic acid the compound has been prepared.

Yield: 10.4%. M/Z [M−H]+1=298.1. 1H NMR data: 1H (400 MHz, d6-DMSO) δ 8.40 (s, 1H), 8.25 (s, 1H), 7.66 (s, 1H), 7.62-7.64 (m, 1H), 7.256 (m, 3H), 2.79-2.83 (m, 1H), 2.48 (s, 1H), 0.71-0.72 (m, 2H), 0.56 (m, 2H).

Preparation of Heterocyclicbenzimidazole Thiophene Carboxamides (XIII), (XIV)

Scheme 3:

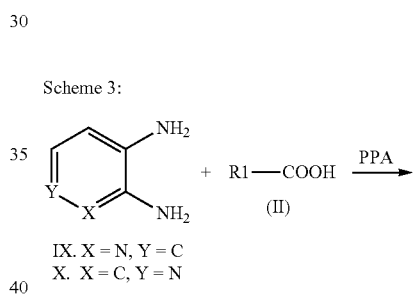

IX. X = N, Y = C
X. X = C, Y = N

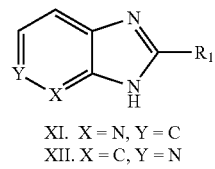

XI. X = N, Y = C
XII. X = C, Y = N

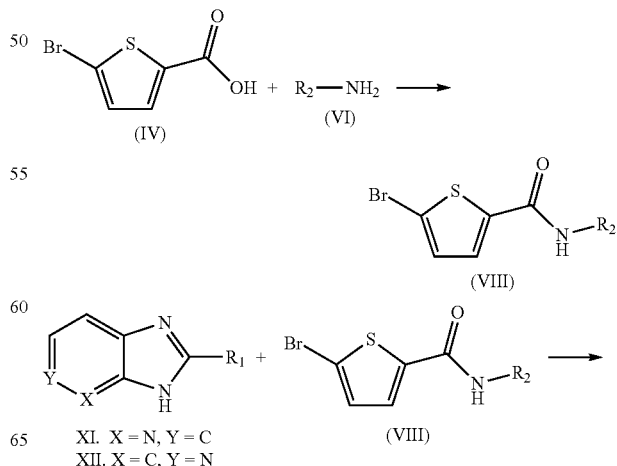

XI. X = N, Y = C
XII. X = C, Y = N

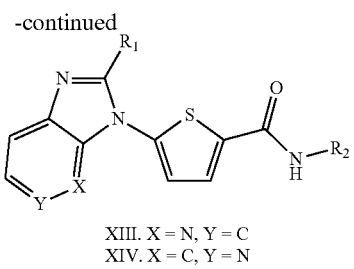

XIII. X = N, Y = C
XIV. X = C, Y = N

Step 1: Preparation of Imidazopyridines

A solution of pyridinediamine (IX), (X), (45.8 mmoles), acetic acid (458.0 mmoles) in PPA (50 ml) was heated to 135-140° C. for 2-4 h under nitrogen atmosphere. After completion of reaction, cooled, transferred the reaction to 250 ml of cold water, charcoal was added and the mixture filtered over a celite bed. The filtrate was basified with aq. ammonia solution till the pH~10-12. Extracted the basified reaction with ethyl acetate (250 ml×3), dried the ethyl acetate layer with sodium sulfate and distilled off the solvent completely to residue. To the residue hexane (50 ml) was added and filtered to get the desired compound (XI and XII).

TABLE 6

Imdiazopyridines (XI), (XII):

| imidazopyridines | Yield % |
|---|---|
| (structure) | 55.0 |
| (structure) | 41.0 |

Step II: Preparation of Thiophenecarboxamides (VIII)

A solution of amine (VI) (28.98 mmoles) in DCM (200 ml) was added to a stirred and cooled (0° C.) solution of 5-bromo-2-thiophenecarboxylic acid (IV) (24.15 mmoles) in DCM (250 ml) and the mixture was stirred for 5 min. HOBt (9.66 mmoles) and N-methylmorpholine (28.98 mmoles) were added to the reaction mixture and stirred for 30 min at 0-5° C. After 30 minutes EDC.HCl (28.98 mmoles) was added and stirred for 3 h at 0° C. and then stirred at room temperature for 10 h. The mixture was diluted with water (100 ml) and organic layer was separated. The organic layer was washed with sodium bicarbonate solution and brine solution, dried over $Na_2SO_4$, distillation of solvent completely under reduced pressure to residue. To the residue hexane (50 ml) added and stirred for 30 min, filtered to get the desired compound (VIII) in 81% yield.

Step III: Preparation of Imidazopyridine Thiophene Carboxamides (XIII), (XIV)

Charged imidazopyridines (XI or XII) (5.115 mmoles), 2-bromo-thiophene-2-carboxamide (VIII) (3.938 mmoles), cesium carbonate (7.161 mmoles), cuprous oxide (0.307 mmoles), 4,7-dimethoxy-1,10-phenathroline (0.716 mmoles), PEG (5.115 mmoles) and DMSO to the RB flask fitted with thermo well and condenser. The reaction mass was heated to 110-115° C. under magnetic stirring for 24 hours. After completion, it was cooled to room temperature, dichloromethane (500 ml) added and filtered through a celite bed, washed the bed with dichloromethane (100 ml×2), distilled off the solvent completely under reduced pressure. Aq. ammonia (10 ml) was added and extracted with ethyl acetate (250 ml×3). Dry the ethyl acetate layer with sodium sulfate, distilled completely to get the crude compound. The crude compound is then purified by using silica gel 60-120 mesh column chromatography and DCM: MeOH 100-5% as mobile phase and further by preparative HPLC method to get the pure compounds (XIII, XIV).

TABLE 7 preparation of imidazopyridine thiophene carboxamides (XIII), (XIV):

| Compound | Yield % | Final structures | $[M - H]^{+1}$ | $^1$H NMR data |
|---|---|---|---|---|
| 72 | 2.5 | (structure) | 299.1 | $^1$H (400 MHz, $d_6$-DMSO) δ 8.71 (d, J = 3.6 Hz, 1H), 8.41 (m, 1H), 7.79 (d, J = 4.4 Hz, 1H), 7.78 (m, 1H), 7.40 (d, J = 4.4 Hz, 1H), 7.24-7.27 (m, 1H), 2.78-2.80 (m, 1H), 2.53 (s, 3H), 0.71 (m, 2H), 0.57 (m, 2H). |
| 73 | 2.0 | (structure) | 299.1 | $^1$H (400 MHz, $d_6$-DMSO) δ 8.67 (brs, 1H), 8.26-8.29 (m, 1H), 8.03-8.05 (m, 1H), 7.75-7.76 (m, 1H), 7.36-7.37 (m, 1H), 7.30-7.32 (m, 1H), 2.80 (m, 1H), 2.54 (s, 3H), 0.70 (m, 2H), 0.57 (m, 2H). |

TABLE 7-continued preparation of imidazopyridine thiophene carboxamides (XIII), (XIV):

| Compound | Yield % | Final structures | [M − H]⁺¹ | ¹H NMR data |
|---|---|---|---|---|
| 71 | 3.6 | | 299.1 | ¹H (400 MHz, d₆-DMSO) δ 8.92 (brs, 1H), 8.72 (m, 1H), 8.36 (m, 1H), 7.82 (d, J = 4.4 Hz, 1H), 7.43 (d, J = 4.4 Hz, 1H), 7.35-7. (m, 1H), 2.79-2.84 (m, 1H), 2.53 (s, 1H), 0.71-0.76 (m, 2H), 0.57-0.61(m, 2H). |

Preparation of 2-Thiophene Substituted Benzimidazoles (XIX)

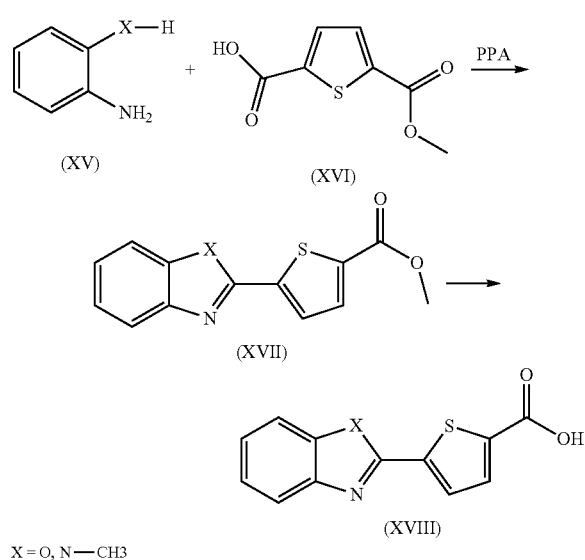

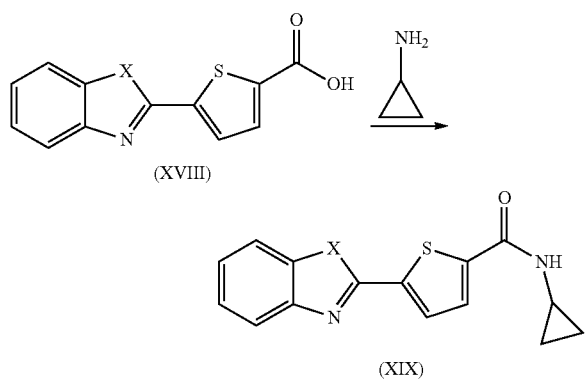

X = O, N—CH3

Step I: Preparation of Benzimidazole Thiophene Carboxylic Acid Ester (XVII)

A solution of amino compound (XV) (9.1 mmoles) and thiophene-2,5-dicarboxylic acid mono methyl ester (XVI) (9.1 m moles) in PPA (15 ml) was stirred under N₂ atmosphere at 150° C. for 2 h. Cooled the reaction to room temperature, poured into cold (0-5° C.) water (100 ml), neutralized with ammonia solution till the pH~9-10, and then extracted with ethyl acetate (50 ml×3), washed with brine, followed by water, dried the organic layer over anhydrous Na₂SO₄ and distilled to give the crude product. This was purified by column chromatography by using silica gel 60-120 mesh and DCM: methanol 100-5% as mobile phase to get the pure compound (XVII)

TABLE 8 benzimidazole thiophene carboxylic acid ester (XVII)

| X | Yield % |
|---|---|
| O | 36.0 |
| N—CH₃ | 22.7 |

Step II: Preparation of Benzimidazole Thiophene Carboxylic Acid (XVIII)

A solution of 10% sodium hydroxide (10 ml) was added to methyl ester (XVII) in dioxane (10 ml) drop by drop. After completion of addition, the reaction mass was heated to 60-65° C. and maintained for 2 hours (reaction monitored by TLC). After completion of reaction, transferred the reaction mass to water (50 ml) and acidified with Con. HCl to pH~4, filtered the precipitated solid, dried to get the desired compound (XVIII).

TABLE 9 preparation of benzimidazole thiophene carboxylic acid (XVIII)

| X | Yield % |
|---|---|
| O | 53.0 |
| N—CH3 | 48.0 |

Step III: Preparation of Benzimidazole Thiophene Carboxamides (XIX)

A solution of cyclopropylamine (1.714 mmoles) in DCM (20 ml) was added to a stirred and cooled (0° C.) solution of thiophene carboxylic acid benzimidazole (1.429 mmoles) in DCM (20 ml) and the mixture was stirred for 5 min. To the above mass HOBt (0.571 mmoles) and N-methyl morpholine (1.714 mmoles) were added and stirred for 30 min, then EDC.HCl (1.714 mmoles) was added and stirred for 3 h at 0° C. and then at room temperature for 4 h. The mixture was diluted with water (15 ml) and organic layer was separated and washed with sodium bicarbonate and brine solution and dried over Na₂SO₄. The solvent was removed off to get the crude compound which was then purified by using silica gel 60-120 mesh column chromatography and DCM: methanol 100-5% as mobile phase to get the pure compound (XIX).

TABLE 10 benzimidazole thiophene carboxamides (XIX)

| Compound | Yield % | [M − H]+ | 1H NMRr |
|---|---|---|---|
| 80 | 20.0 | 285.0 | $^1$H (400 MHZ, D$_6$-DMSO) δ 8.71(D, J = 3.6 HZ, 1H), 7.96(D, J = 4.4 HZ, 1H), 7.84(D, J = 4.4 HZ, 1H), 7.78-7.81(M, 2H), 7.42-7.47(M, 2H), 2.82-2.83(M, 1H), 0.74(M, 2H), 0.60(M, 2H). |
| 79 | 24.2 | 298.1 | $^1$H (400 MHZ, D$_6$-DMSO) δ 8.68(D, J = 3.6 HZ, 1H), 7.86(D, J = 4.4 HZ, 1H), 7.81 (D, J = 4.4 HZ, 1H), 7.65-7.69(M, 2H), 7.25-7.34(M, 2H), 4.05(S, 3H), 2.83-2.84(M, 1H), 0.74-0.75(M, 2H), 0.61-0.62(M, 2H). |

Preparation of Thiophene Benzimidazole Dimer

Scheme 5:

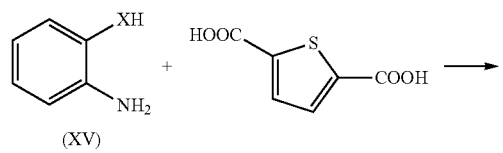

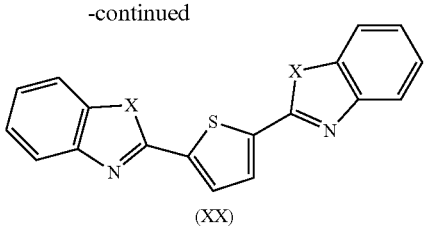

(XX)

X = O, N, N—CH3

A solution of amino compound (XV) (5.8 mmoles) and 2,5-thiophenedicarboxylic acid (5.8 mmoles) in PPA (10 ml) was stirred under N$_2$ atmosphere at 150° C. for 2 h. Cooled the reaction mass to RT, poured into cold water, neutralized with ammonia solution to pH~10-11, then extracted with ethyl acetate, washed with brine followed by water, dried the organic layer over anhydrous Na$_2$SO$_4$ and distilled to give the crude product, which was then purified by using silica gel 60-120 mesh column chromatography and DCM: methanol 100-5% as mobile phase to get the pure compound (XX).

TABLE 11 preparation of thiophene benzimidazole dimer (XX).

| Compound | Yield % | [M − H]+ | 1H NMR |
|---|---|---|---|
| 83 | 5.5 | 321.1 | $^1$H (400 MHZ, D$_6$-DMSO) δ 8.10(S, 2H), 7.83-7.86(M, 4H), 7.46-7.49(M, 4H). |
| 81 | 10.9 | 319.1 | $^1$H (400 MHZ, D$_6$-DMSO) δ 13.11(BRS, 2H), 7.89(M, 2H), 7.57-7.65(M, 4H), 7.24(M, 4H). |
| 82 | 15.0 | 347.1 | $^1$H (400 MHZ, D$_6$-DMSO) δ 7.92(S, 2H), 7.66-7.71(M, 4H), 7.25-7.34(M, 4H), 4.100(S, 6H). |

Preparation of Benzimidazole Thiophene Ketone, Alcohol and Oximes (84), (85), (86), (87), (88), (89), Scheme 6

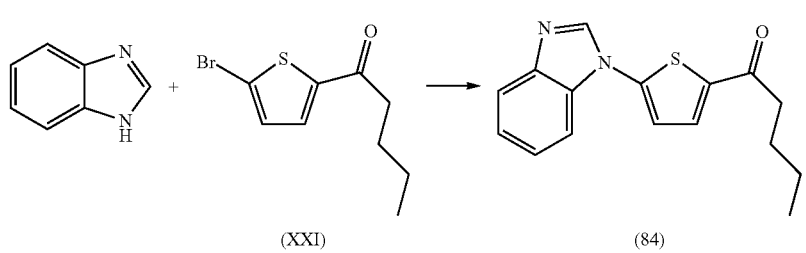

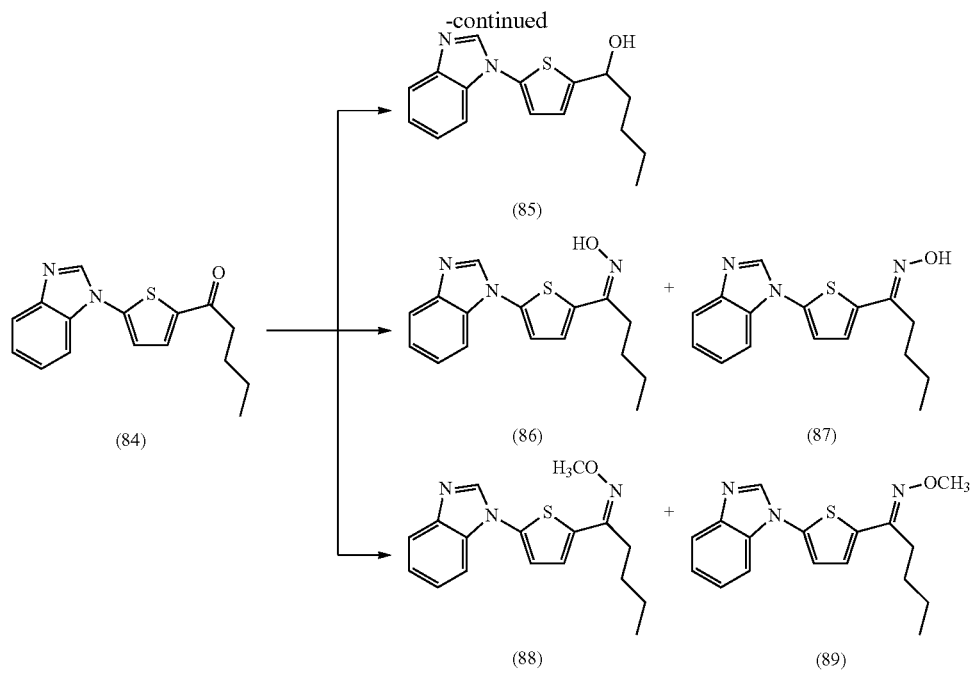

Step 1: Preparation of 1-(5-bromo-2-thienyl)pentan-1-one (XXI)

Charged aluminum chloride (183 mmoles), pentanoyl chloride (147 mmoles) and bromothiophene (122 mmoles) to the RB flask fitted with thermo well, stirred the reaction for 2 hours at 25-30° C. After completion of reaction, cooled the RM to 0-5° C. and added Water (100 ml). Extracted the reaction mass with ethyl acetate (2×200 ml), separated the organic layer and dried with sodium sulphate, distilled off the solvent under reduced pressure to the residue. Residue was high vacuum distilled to get the pure compound (XXI).

Step II: Preparation of 1-[5-(1H-benzimidazol-1-yl)-2-thienyl]pentan-1-one (84)

Charged Benzimidazole (12.11 mmoles), cesium carbonate (14.11 mmoles), cuprous oxide (0.4 mmoles), 2-Amino-4,6-dihydroxypyrimidine (1.5 mmoles), PEG (catalyst), keto thiophene (XXI) and NMP (5 ml) to the RB flask fitted with thermo well and condenser. The reaction mixture was heated to 155-160° C. and the temperature was maintained for 10-12 hrs at 155-160° C. After completion of reaction, cooled to room temperature, added water (25 ml), extracted with ethyl acetate (2×100 ml), washed with 10% brine solution, dried the ethyl acetate layer over sodium sulfate and distilled off the solvent completely at reduced pressure to get crude compound. The crude compound was purified by using silica gel 60-120 silica gel column chromatography and DCM: methanol: 100-5% as mobile phase to get the pure compound (84).

Preparation of 1-[5-(1H-benzimidazol-1-yl)-2-thienyl]pentan-1-ol (85)

The compound (84) (0.703 mmoles) was dissolved in methanol (10 ml), cooled to 0-5° C., added sodium borohydride in lots at 0-5° C. in 5 minutes, after completion of addition, the reaction mixture was warmed to 25 to 30° C., stirred for 2.0 hrs. After completion of reaction, quenched the reaction with water (10 ml) and extracted in ethyl acetate (2×100 ml), washed with 10% brine, and dried over sodium sulphate. Distilled off the ethyl acetate completely to residue to get the crude compound, The crude compound was purified by using silica gel 60-120 silica gel column chromatography and DCM: methanol: 100-5% as mobile phase to get the pure compound (85).

Preparation of (1E and z))-1-[5-(1H-benzimidazol-1-yl)-2-thienyl]pentan-1-one oxime (86 & 87)

To the solution of compound (84) (0.703 mmoles) in ethanol (10 ml) was added hydroxylamine HCl (2.878 mmoels) and pyridine (2.844 mmoles) at ambient temp. The reaction was heated to reflux for 2.0 hrs. After completion of reaction, distilled off the solvent completely, added water (20 ml) and the product was extracted in Ethyl acetate (2×100 ml), washed with 10% brine and dried over sodium sulphate. The solvent was distilled completely under reduced pressure to get the crude compound. This crude compound was purified by preparative HPLC to get the pure isomers (86 & 87).

Preparation of (1E and Z)-1-[5-(1H-benzimidazol-1-yl)-2-thienyl]pentan-1-one O-methyloxime (88 & 89)

To the solution of compound (84) (0.703 mmoles) in Ethanol (10 ml) was added N-methoxy amine HCl (2.878 m.moles) and Pyridine (2.844 m.moles) at ambient temp. The reaction mass was heated to reflux for 2.0 hrs. After completion of reaction, distilled off the solvent completely, added Water (20 ml) and the product was extracted in ethyl acetate (2×100 ml), washed with 10% brine and dried over sodium sulphate. The solvent was distilled completely under reduced pressure to get the crude compound. This crude compound was purified by preparative HPLC to get the pure isomers (88 & 89).

| Compound | Structure | Yield % | [M − H]⁺¹ | ¹H NMR data |
|---|---|---|---|---|
| 84 | 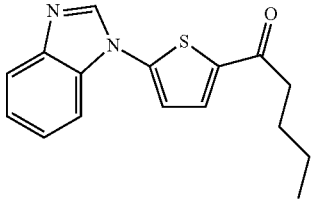 [SMILES: CCCCC(=O)c1ccc(-n2cnc3ccccc32)s1] | 43 | 285.1 | ¹H (400 MHZ, CDCL) δ 8.14 (S, 1H), 7.86-7.88 (M, 1H), 7.70-7.72 (M, 1H), 7.70 (D, J = 4.4 HZ, 1H), 7.38-7.43 (M, 2H), 7.18 (D, J = 4.4 HZ, 1H), 2.92 (T, J = 7.2 HZ, 1H), 1.42-1.47 (M, 2H), 0.97 (T, J = 7.2 HZ, 1H) |
| 85 | 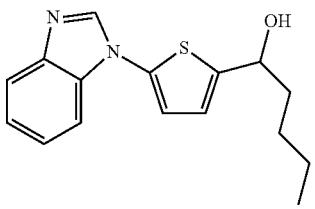 [SMILES: CCCCC(O)c1ccc(-n2cnc3ccccc32)s1] | 75 | 287.0 | ¹H (400 MHZ, CDCL₃) δ 7.99 (S, 1H), 7.79-7.81 (M, 1H), 7.53-7.56 (M, 1H), 7.32-7.35 (M, 2H), 6.97 (D, J = 4.4 HZ, 1H), 6.19 (D, J = 4.4 HZ, 1H), 4.94 (T, J = 6.8 HZ, 1H), 3.45 (BRS, 1H), 1.55-1.95 (M, 2H), 1.30-1.53 (M, 4H), 0.95 (T, J = 9.2 HZ, 3H), |
| 87 | 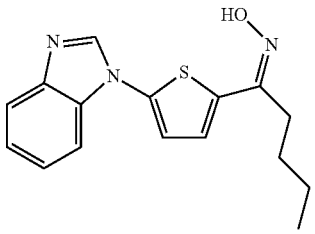 [SMILES: CCCC/C(=N/O)c1ccc(-n2cnc3ccccc32)s1] | 20 | 300.4 | ¹H (400 MHZ, CDCL₃) δ 8.83 (BRS, 1H), 8.28 (S, 1H), 7.85-7.87 (M, 1H), 7.66-7.69 (M, 1H), 7.35-7.41 (M, 2H), 7.20 (D, J = 4.4 HZ, 1H), 2.81 (T, J = 7.6 HZ, 2H), 1.64-1.72 (M, 2H), 1.45-1.53 (M, 2H), 0.99 (T, J = 7.6 HZ, 3H) |
| 86 | 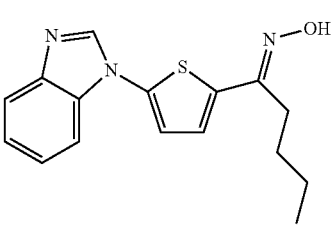 [SMILES: CCCC/C(=N\O)c1ccc(-n2cnc3ccccc32)s1] | 20 | 300.4 | ¹H (400 MHZ, CDCL₃) δ 10.10 (BRS, 1H), 8.17 (S, 1H), 7.87-7.91 (M, 1H), 7.46 (D, J = 4.4 HZ, 1H) 7.35-7.40 (M, 2H), 7.18 (D, J = 4.4 HZ, 1H), 2.78 (T, J = 7.6 HZ, 2H), 1.71-1.78 (M, 2H), 1.42-1.52 (M, 2H), 0.97 (T, J = 7.6 HZ, 3H) |
| 88 | 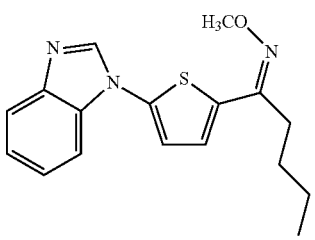 [SMILES: CCCC/C(=N/OC)c1ccc(-n2cnc3ccccc32)s1] | 18 | 314.1 | ¹H (400 MHZ, CDCL₃) δ 8.14 (S, 1H), 7.85-7.87 (M, 1H), 7.34-7.66 (M, 1 H), 7.27-7.39 (M, 2H), 7.15 (D, J = 4.4 HZ, 1H), 7.06 (D, J = 4.4 HZ, 1H), 3.96 (S, 3H), 2.71 (T, J = 7.6 HZ, 2H), 1.60 (M, 2H), 1.42 (M, 2H), 0.912 (T, J = 9.2 HZ, 3H). |
| 89 | 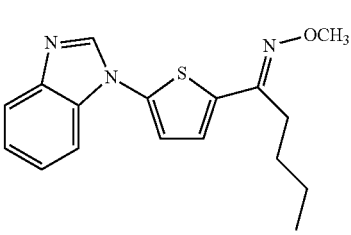 [SMILES: CCCC/C(=N\OC)c1ccc(-n2cnc3ccccc32)s1] | 27 | 314.1 | ¹H (400 MHZ, CDCL₃) δ 8.12 (S, 1H), 7.85-7.87 (M, 1H), 7.64-7.66 (M, 1 H), 7.41 (D, J = 4.4 HZ, 1H), 7.35-7.38 (M, 2H), 7.14 (D, J = 4.4 HZ, 1H), 2.72 (T, J = 7.6 HZ, 2H), 1.71 (M, 2H), 1.45 (M, 2H), 0.97 (T, J = 9.2 HZ, 3H). |

Preparation of Substituted Imidazole Thiophene Carboxamides (XXVIII)

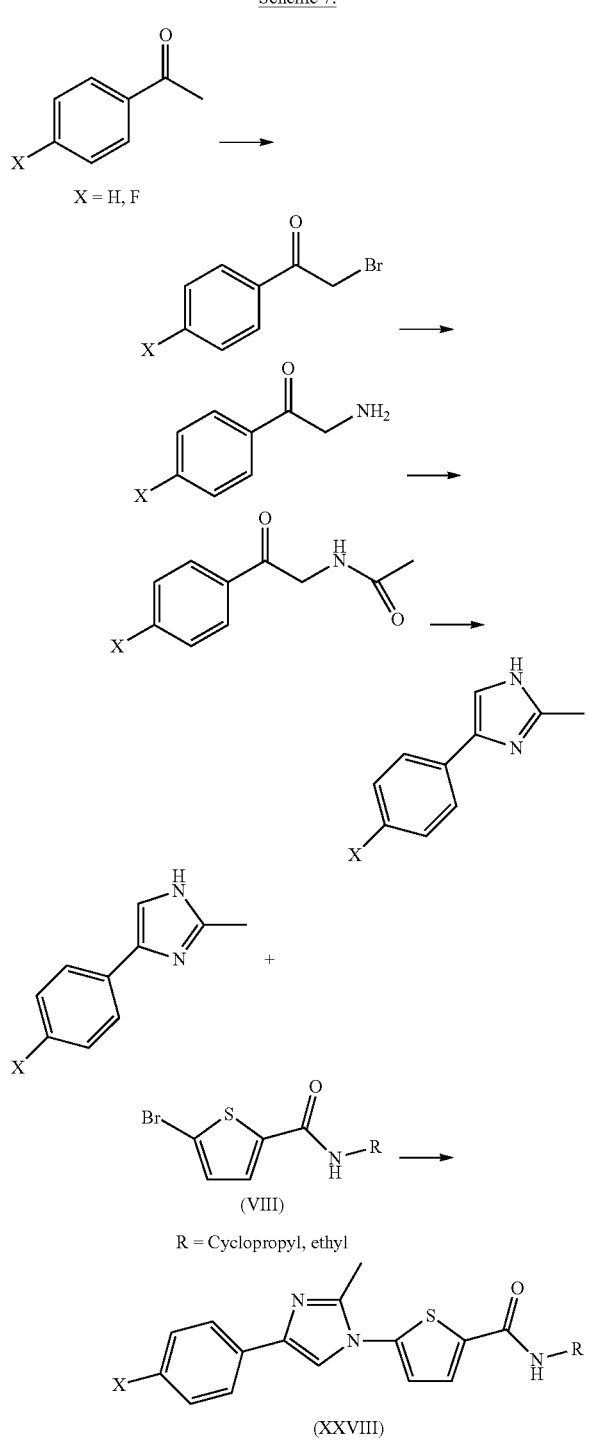

Scheme 7.

(VIII)
R = Cyclopropyl, ethyl (XXVIII)

Step I: Preparation of Phenacylbromides

Bromine (43.75 m. moles) was added to a solution of acetophenones (43.75 m. moles) in diethyl ether (25 ml) at 0° C. in 10 min and stirred for 1 hour at 0-5° C. After completion of reaction, water (10 ml) was added and separated the organic layer, dried the organic layer with sodium sulphate, distilled off the solvent to get the desired compound.

| X | Yield |
|---|---|
| H | 57.6% |
| F | 68.9% |

Step II: Preparation of Phenacylamines

To a solution of phenacylbromide (23.11 m. moles) in chloroform (50 ml), hexamine (23.54 m. moles) was added and stirred for 4 hours at RT, filtered the precipitated hexamine adduct. The adduct was then heated with methanol (100 ml) and Con.HCl (7 ml) for 3 hours under reflux, cooled, filtered the inorganics, washed with methanol (20 ml), distilled out the solvent completely under reduced pressure and column purified using DCM: methanol: 100-5% and silica gel as stationary phase to get the desired compound.

| X | Yield |
|---|---|
| H | 80.85% |
| F | 48.7% |

Step III: Preparation of Phenylacylacetamide

To a suspension of phenacylamine hydrochloride (60 m. moles) in tetrahydrofuran (240 ml), triethyl amine (120 m. moles) was added, followed by the addition of acetic anhydride (100 m. moles) at RT and stirred for 1 hr. Filtered the reaction mass and filtrate was concentrated under reduced pressure to get the desired compound.

| X | Yield |
|---|---|
| H | 80.85% |
| F | 48.7% |

Step IV: Preparation of 4-phenyl imidazoles

A solution phenacylacetamide (10.15 m. moles) ((IV), ammonium acetate (64.86 m. moles) and acetic acid (166.6 m. moles) in xylene (150 ml) was refluxed azeotropically for 6 hours along with the removal of water. After completion of reaction, cooled the reaction mass to RT, water (25 ml) washed, distilled to get the crude compound. This was then column purified using DCM: methanol 100-5% as mobile phase and silica gel 60-120, to get the desired compound.

| X | Yield |
|---|---|
| H | 25% |
| F | 55.5% |

Step V: Preparation of PMIMD-TCA Cyclopropylamide (XXVIII)

Charged, imidazole (V) (2.529 m. moles), cesium carbonate (3.54 m. moles), cuprous oxide (0.152 m. moles), PEG (2.549 m. moles), 5-bromo-thiophen-2-carboxylic acid amide (1.947 m. moles), 4,7-dimethoxy-1,10-phenanthrolein (0.354 m. moles) to the DMSO (50 ml) in RB flask, and the reaction mixture was heated to 115-120° C. and the temperature was maintained for 20 hrs. (Reaction is monitored by TLC). After completion of reaction, cooled to RT, diluted with DCM (250 ml) and filtered on hyflo bed. DCM was evaporated under reduced pressure. To the residue ammonia solution was added and extracted with ethyl acetate (250 ml×3 times), which was then washed with water and dried over sodium sulfate. Ethyl acetate was evaporated under reduced pressure to get the crude product, which was purified by silica gel column chromatography using DCM: methanol 100-5% to get the desired compound (89) in 25% yield.

| Compound | Yield | $[M - H]^{+1}$ | $^1$H NMR |
|---|---|---|---|
| 74 | 25% | 324.1 | $^1$H (400 MHz, d$_6$-DMSO) δ 8.64(brs, 1H), 7.69-7.91(m, 4H), 7.21-7.27(m, 4H), 2.79(m, 1H), 2.40(s, 3H), 0.71(m, 2H), 0.56(m, 2H), |
| 75 | 11.1% | 312.1 | $^1$H (400 MHz, DMSO d6) δ 8.65-8.64 (m, 1H), 7.93 (s, 1H), 7.25-7.82 (m, 7H), 3.26-3.33(m, 2H), 2.43(s, 3H), 1.15(t, 3H). |
| 76 | 10.5% | 342.1 | $^1$H (400 MHz, DMSO d6) δ 8.63-8.64 (d, 1H), 7.91 (s, 1H), 2.79-2.82(m, 1H), 2.41(s, 3H), 0.70-0.73(m, 2H), 0.57-0.60(m, 2H). |

Compounds 99 and 100

Compound 99

5-(1H-benzo[d][1,2,3]triazol-1-yl)-N-cyclopropylthiophene-2-carboxamide

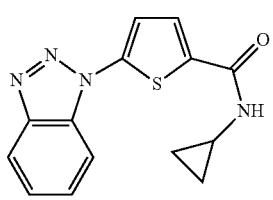

$^1$H NMR (400 MHz, DMSO) δ 8.68 (br, 1H), 8.20-8.18 (sd, 1H), 8.09-8.07 (sd, 1H), 7.81-7.80 (d, J=4 Hz, 1H), 7.73-7.70 (m, 1H), 7.68-7.67 (d, J=4 hZ, 1H), 7.56-7.52 (m, 1H), 2.83-2.77 (m, 1H), 0.75-0.69 (m, 2H), 0.60-0.56 (m, 2H).

$^{13}$C NMR (101 MHz, DMSO) δ 162.37, 146.32, 140.77, 137.42, 132.02, 130.31, 128.17, 126.10, 120.71, 119.60, 111.82, 23.60, 6.48.

Compound 100

N-cyclopropyl-5-(1H-indazol-1-yl)thiophene-2-carboxamide

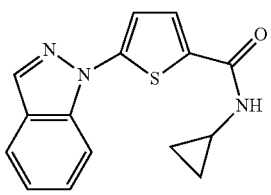 [SMILES: O=C(NC1CC1)c1ccc(-n2ncc3ccccc32)s1]

$^1$H NMR (400 MHz, DMSO) δ 8.52-8.51 (br, 1H), 8.41 (s, 1H), 8.02-8.00 (dd, 1H), 7.90-7.89 (sd, 1H), 7.71-7.70 (d, J=4 Hz, 1H), 7.59-7.55 (m, 1H), 7.44-7.43 (d, J=4 HZ, 1H), 7.33-7.29 (st, 1H), 2.80-2.75 (m, 1H), 0.71-0.66 (m, 2H), 0.57-0.54 (m, 2H).

$^{13}$C NMR (101 MHz, DMSO) δ 162.82, 146.58, 138.47, 137.93, 133.81, 129.28, 128.43, 126.00, 123.31, 122.60, 114.93, 111.60, 23.53, 6.48.

Example 2

High-Throughput Screen to Identify Inhibitors of pfDHODH

DHODH catalyzes the oxidation of L-DHO to orotate via a ping-pong mechanism using a FMN cofactor that is re-oxidized by fumarate or NAD$^+$ in Type 1 enzymes or CoQ$_n$ in mitochondrial, Type 2 DHODH variants such as the *Plasmodium* spp. and human isoforms.

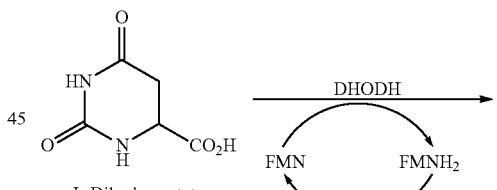
L-Dihydroorotate

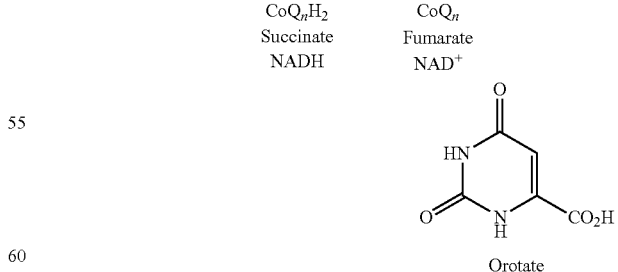
Orotate

Figure 1B:
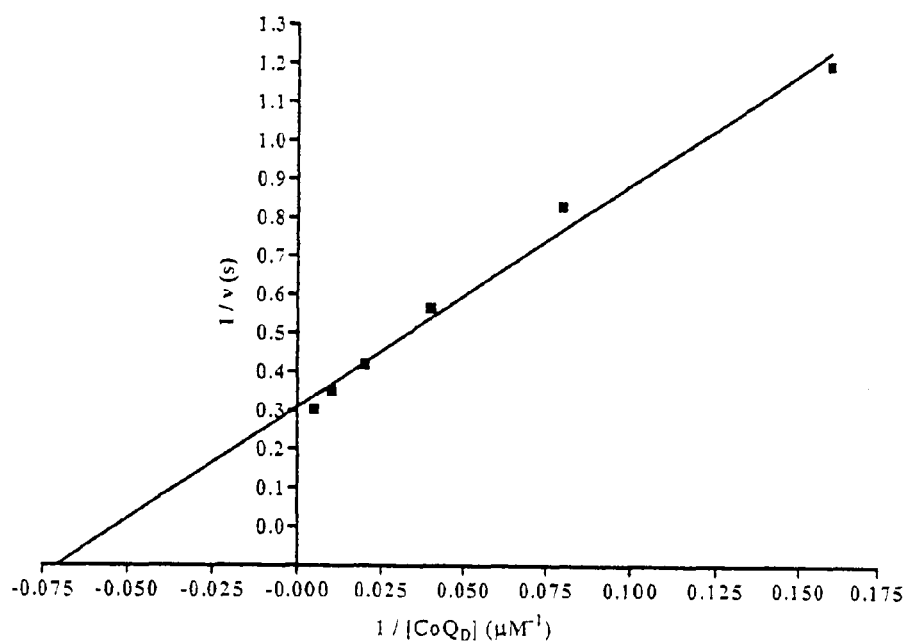

Enzymatic activity of DHODH can be assessed in the presence of L-DHO and CoQ$_n$ by directly measuring the formation of orotate or coupling the assay to the chromogen 2,6-dichloroindophenol (DCIP). The latter colorometric assay was adapted for high-throughput screening of pfD- HODH in 384-well plates in a manner similar to that described by Baldwin et al. [37]. Decylubiquinone (CoQ$_D$) was chosen as the second substrate as it is significantly more soluble than ubiquinone (CoQ$_{10}$) and has been previously described to be efficiently utilized by both pfDHODH and hsDHODH [43, 44]. The concentrations of L-DHO and CoQ$_D$ used in the high-throughput screen (HTS) were based upon substrate binding affinity as determined by the direct assay (FIG. 1). The optimized screening assay afforded a Z-factor≈0.6, a value between 0.5 and 1 is generally considered favorable for a HTS [38].

The Genzyme Corporation chemical library of 208,000 compounds was screened at an initial drug concentration of 10 μM to identify inhibitors of pfDHODH. Based upon the screening cascade highlighted in FIG. 3, 689 compounds were classified as primary hits with ≥70% inhibition of pfDHODH activity when compared to control reactions where no drug is present. These compounds were cherry-picked and re-tested at concentration of 1 μM yielding 55 compounds that were found to inhibit ≥50% of enzymatic activity. Of these, 38 compounds were grouped as secondary hits based upon submicromolar IC$_{50}$ values with respect to pfDHODH activity using the screening assay conditions. The long, hydrophobic quinone binding tunnel of pfDHODH likely accommodates a variety of ligands which is consistent with the structural diversity of compounds that were identified to inhibit the enzyme [32].

Example 3

Figure 2B:
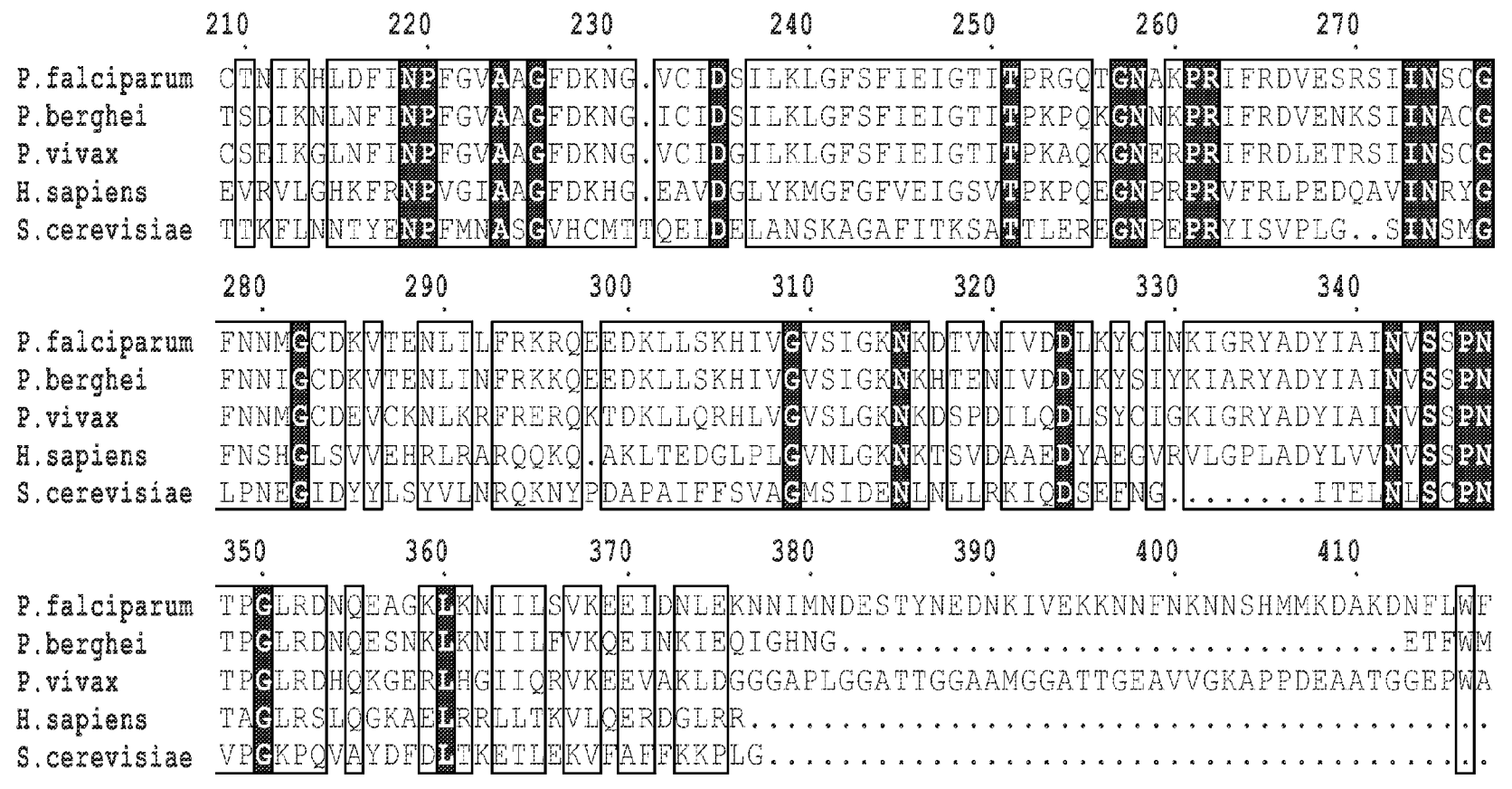

Inhibitory Activity and Species Selectivity of Screening Hits Against DHODH Isoforms Inhibitors that inhibited *P. falciparum* DHODH activity were tested for inhibition of DHODH activity of another human malaria parasite *P. vivax* and the causative agent for rodent malaria, *P. berghei*. Inhibition of both pfDHODH and *P. vivax* DHODH (pvDHODH) may allow for the development of a single drug for the treatment of the two major human malarias. The drug development pathway for *P. falciparum* malaria involves testing in mice, which are susceptible to *P. berghei* rather than *P. falciparum*. Since all three DHODH isoforms share significant homology, candidate phDHODH inhibitors may be efficacious against DHODH enzymes from other *Plasmodium* spp (FIGS. 2A-2C).

Figure 3:
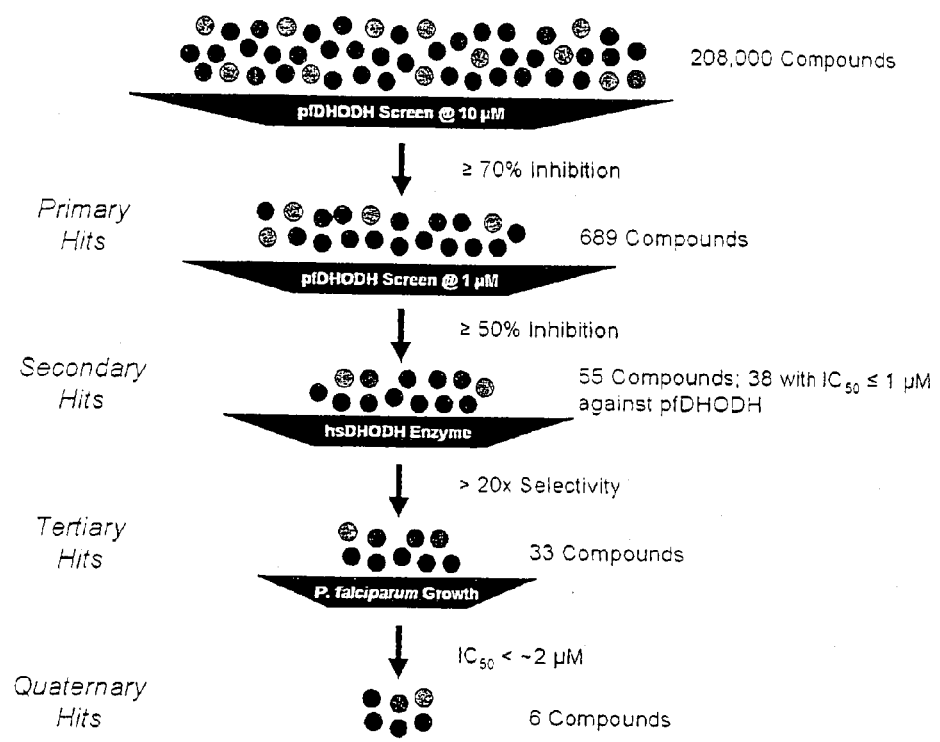
FIG. 3. Screening cascade for inhibitors of pfDHODH. 208,000 compounds from the Genzyme Chemical Library were screened at a concentration of 10 μM for enzymatic inhibition of pfDHODH using the DCIP assay. 689 compounds were classified as primary hits with ≥70% inhibition of pfDHODH activity and then re-tested at a concentration of 1 μM. 55 compounds were found to inhibit ≥50% of enzymatic activity at 1 μM, 38 of these compounds were grouped as secondary hits based upon submicromolar IC$_{50}$ values. Compounds selective for pfDHODH compared to the human isoform were categorized as tertiary hits. Six compounds, deemed quaternary hits, were found to inhibit pfDHODH activity and *P. falciparum* growth in culture.
Figure 4:
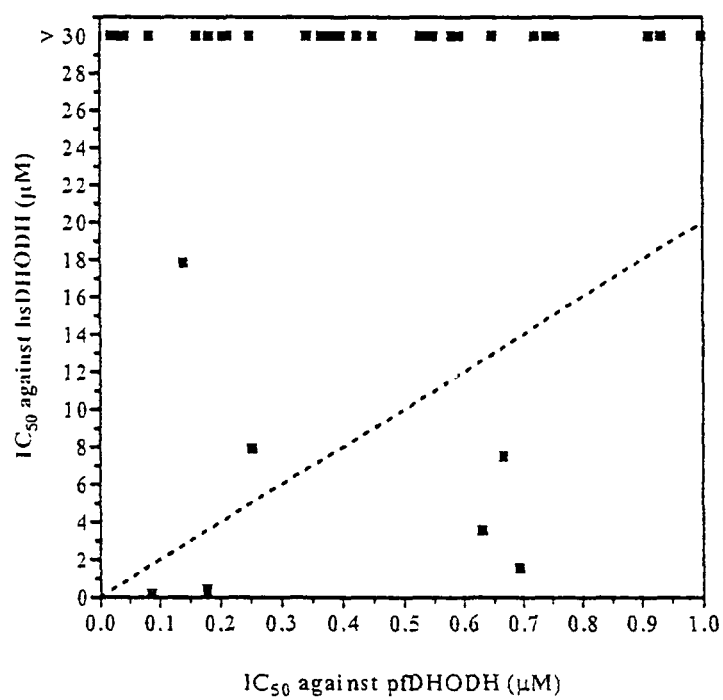
FIG. 4. Species selectivity of pfDHODH inhibitors. Compounds above the dashed line demonstrate ≥20× selectivity for pfDHODH over the human isoform, 33 of the 38 compounds met this criterion.

As part of the screening cascade depicted in FIG. 3, IC$_{50}$ values for the 38 compounds deemed secondary hits from HTS were determined for pfDHODH and hsDHODH using the DCIP assay. Most of the compounds (~87% or 33 compounds) were highly selective for the *P. falciparum* protein (FIG. 4). The 33 selective pfDHODH inhibitors, deemed tertiary hits, were then tested for efficacy against *P. berghei* (pbDHODH), pvDHODH, and *S. cerevisiae* DHODH (scDHODH) at a single concentration of 10 μM using the DCIP assay. Twenty-four of the compounds inhibited all three *Plasmodium* isoforms while none of the compounds were inhibitory against scDHODH. Interestingly, Compound 4 was the only compound found to inhibit only pfDHODH and none the other enzyme isoforms. IC$_{50}$ values for the six quaternary hits, their selection criteria is Example 4, were determined with respect to pbDHODH, pvDHODH, scDHODH in addition to the human and *P. falciparum* isoforms (Table 1). Inhibition of the Type 1 DHODH from *S. cerevisiae* was assessed as a control and will be discussed in greater detail in Example 6.

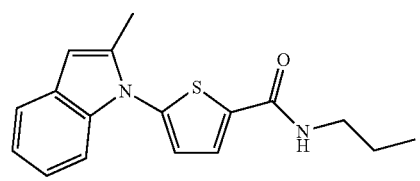

Compound 1

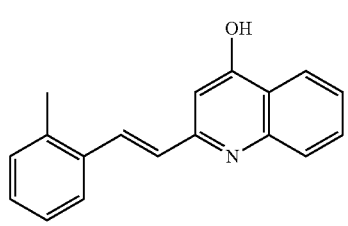

Compound 2

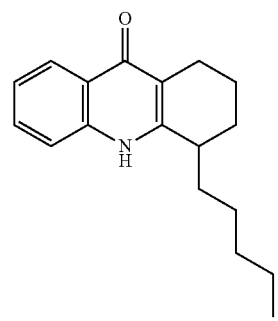

Compound 3

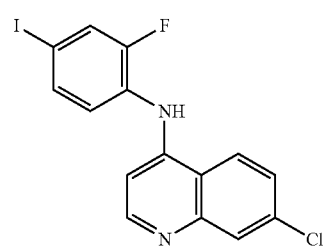

Compound 4

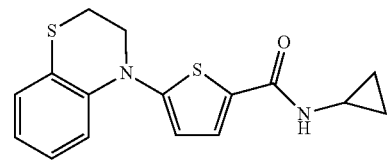

Compound 5

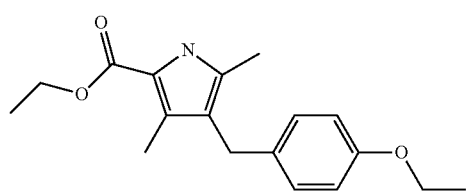

Compound 6

TABLE 1

Species selectivity of DHODH enzyme inhibitors.

| Compound # | IC$_{50}$ (μM)[1] | | | | |
|---|---|---|---|---|---|
| | pfDHODH | pbDHODH | pvDHODH | scDHODH | hsDHODH |
| 1 | 0.042 ± 0.007 | 0.06 ± 0.007 | 0.42 ± 0.02 | >10 | >30 |
| 2 | 0.93 ± 0.1 | 0.56 ± 0.07 | 5.6 ± 0.4 | >10 | >30 |
| 3 | 0.34 ± 0.1 | 0.11 ± 0.01 | 0.51 ± 0.03 | >10 | >30 |
| 4 | 0.58 ± 0.1 | >10 | >10 | >10 | >30 |
| 5 | 0.25 ± 0.03 | 0.38 ± 0.06 | 0.28 ± 0.01 | >10 | 7.9 ± 0.4 |
| 6 | 0.083 ± 0.01 | 0.06 ± 0.007 | 0.04 ± 0.002 | >10 | >30 |

[1]IC$_{50}$ values for secondary hits from the HTS were determined using the DCIP assay. The reagent concentrations were 200 μM L-DHO, 18 μM CoQ$_D$, 100 μM DCIP, and 20 nM pfDHODH, pbDHODH, pvDHODH, or hsDHODH; 115 μM fumarate was used in lieu of CoQ$_D$ to assay inhibition of scDHODH activity.

Example 4

Effect of DHODH Inhibitors on *P. falciparum* Cultures

To reach their DHODH target in vivo, the compounds must cross the red blood cell, parasite, and mitochondrial membranes to reach the enzyme target. The 33 selective pfDHODH inhibitors, or tertiary hits, were tested for their ability to inhibit an in vitro culture of *P. falciparum* 3D7. Inhibition of parasite proliferation was measured by the relative reduction of [³H]-hypoxanthine uptake by infected cultures [40]. An IC$_{50}$ of ≤2 μM was deemed necessary for classification as a quaternary hit, FIG. 3. Six compounds met this criterion and were subsequently tested for inhibitory activity against the HB3 and Dd2 *P. falciparum* strains, their IC$_{50}$ values are reported in Table 2. IC$_{50}$ values of additional compounds of the invention are reported in Table 2b.

TABLE 2

Inhibition of *P. falciparum* growth by pfDHODH inhibitors and known antimalarials.

| Compound # or Drug Name | IC$_{50}$ (μM)[1] | | | | |
|---|---|---|---|---|---|
| | 3D7 | Dd2 | HB3 | D10 | D10-scDHODH[2] |
| 1 | 0.47 | 0.29 | 0.47 | 0.61 | >10 |
| 2 | 0.32 | 0.25 | 0.24 | 0.30 | 8.8 |
| 3 | 0.32 | 0.23 | 0.27 | 0.37 | >10 |
| 4 | 1.8 | 2.3 | 2.2 | 1.0 | 0.98 |
| 5 | 0.89 | 0.62 | 0.91 | 0.95 | >10 |
| 6 | 0.77 | 0.44 | 0.69 | 1.2 | >10 |
| Chloroquine | 0.010 | 0.18 | 0.008 | 0.015 | 0.013 |
| Pyrimethamine | 0.036 | >10 | 0.94 | 0.055 | 0.047 |
| Atovaquone | 0.00018 | 0.0002 | 0.00022 | 0.00042 | >2 |

[1]IC$_{50}$ values were determined from dose-effect curves correlated with the relative reduction of [³H]-hypoxanthine uptake by parasite infected erythrocytes.
[2]The IC$_{50}$ values reported are based upon the second phase of the dose-effect curves shown in FIG. 5.

The 3D7 strain of *P. falciparum* is sensitive to common antimalarials such as chloroquine and pyrimethamine and thus, is generally used as a laboratory strain and ideal for preliminary testing of candidate drugs. The HB3 and Dd2 strains are derived from patient isolates and are both chloroquine resistant but have different sensitivities to pyrimethamine. HB3 is pyrimethamine resistant, while Dd2 is pyrimethamine resistant [45, 46]. Inhibition of the three *P. falciparum* strains by the DHODH inhibitors did not vary significantly.

TABLE 2b

Inhibition of *P. falciparum* growth by pfDHODH inhibitors and known antimalarials.

| Compound | Structure | pfDHODH IC50 uM | 3D7 EC50 uM | Dd2 EC50 uM |
|---|---|---|---|---|
| 7 | 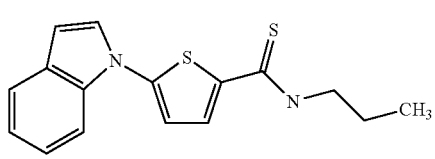 [SMILES: CCCNC(=S)c1ccc(-n2ccc3ccccc32)s1] | 0.459 (Hu: >30) | 0.708 | 1.030 |

TABLE 2b-continued
Inhibition of *P. falciparum* growth by pfDHODH inhibitors and known antimalarials.
| Compound | Structure | pfDHODH IC50 uM | 3D7 EC50 uM | Dd2 EC50 uM |
|---|---|---|---|---|
| 1 | 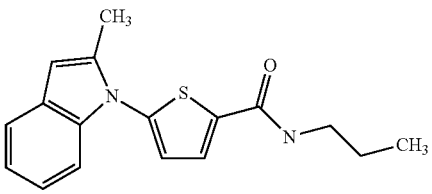 [SMILES: CCCNC(=O)c1ccc(-n2c(C)cc3ccccc32)s1] | 0.064 (Hu: >30) | 0.386 | 0.493 |
| 13 | 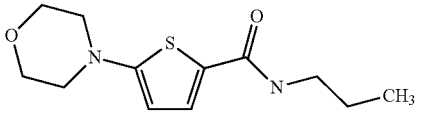 [SMILES: CCCNC(=O)c1ccc(N2CCOCC2)s1] | >250 | >10 | >10 |
| 14 | 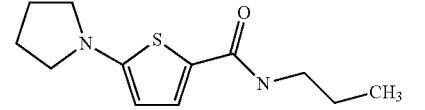 [SMILES: CCCNC(=O)c1ccc(N2CCCC2)s1] | >250 | >10 | >10 |
| 8 | 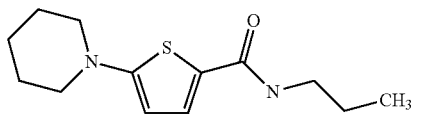 [SMILES: CCCNC(=O)c1ccc(N2CCCCC2)s1] | 230 | >10 | >10 |
| 11 | 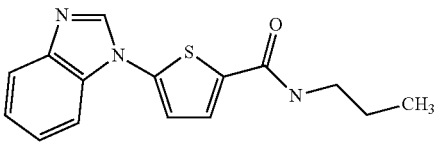 [SMILES: CCCNC(=O)c1ccc(-n2cnc3ccccc32)s1] | 0.703 (Hu: >30) | 0.472 | 1.102 |
| 9 | 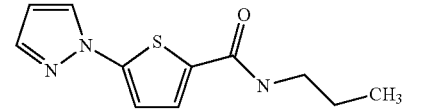 [SMILES: CCCNC(=O)c1ccc(-n2cccn2)s1] | >250 | >10 | >10 |
| 10 | 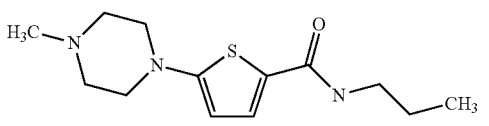 [SMILES: CCCNC(=O)c1ccc(N2CCN(C)CC2)s1] | >250 | >10 | >10 |
| 15 | 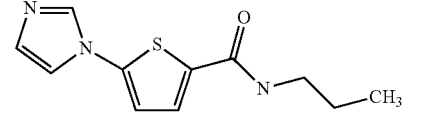 [SMILES: CCCNC(=O)c1ccc(-n2ccnc2)s1] | 165 | >10 | >10 |
| 16 | 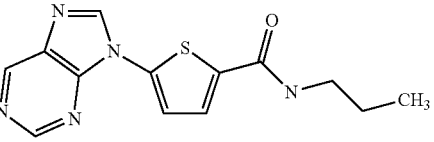 | Not done | >10 | >10 |
| 12 | 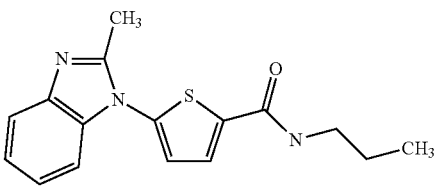 [SMILES: CCCNC(=O)c1ccc(-n2c(C)nc3ccccc32)s1] | 0.172 (Hu: >30) | 0.628 | Not done |

TABLE 2b-continued

*Inhibition of P. falciparum growth by pfDHODH inhibitors and known antimalarials.*

| Compound | Structure | pfDHODH IC50 uM | 3D7 EC50 uM | Dd2 EC50 uM |
|---|---|---|---|---|
| 17 | 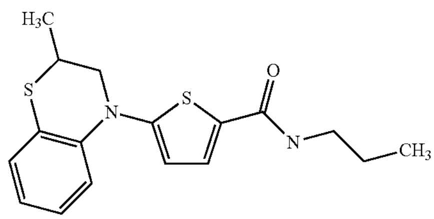 [SMILES: CCCNC(=O)c1ccc(N2CC(C)Sc3ccccc32)s1] | 19.1 | >10 | >10 |
| 18 | 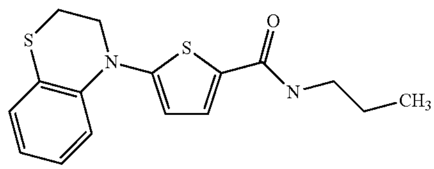 [SMILES: CCCNC(=O)c1ccc(N2CCSc3ccccc32)s1] | 9.2 | >10 | >10 |
| 19 | 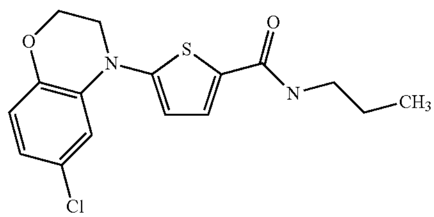 [SMILES: CCCNC(=O)c1ccc(N2CCOc3ccc(Cl)cc32)s1] | 7.5 | >10 | >10 |
| 20 | 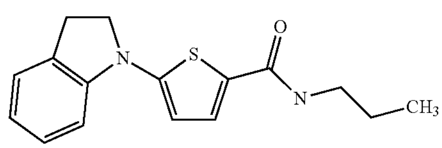 [SMILES: CCCNC(=O)c1ccc(N2CCc3ccccc32)s1] | >30 | >10 | >10 |
| 21 | 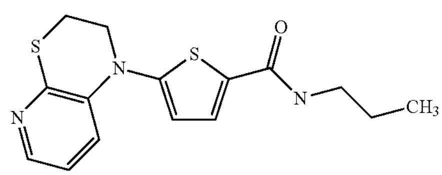 [SMILES: CCCNC(=O)c1ccc(N2CCSc3ncccc32)s1] | 13.8 | >10 | >10 |
| 22 | 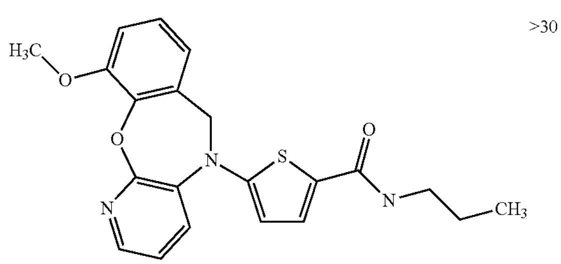 | >30 | >10 | >10 |
| 23 | 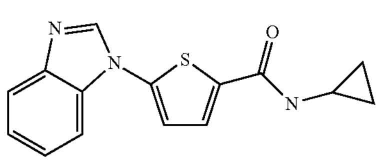 [SMILES: O=C(NC1CC1)c1ccc(-n2cnc3ccccc32)s1] | 0.056 (Hu: >30) | 0.079 | 0.088 |

TABLE 2b-continued

Inhibition of *P. falciparum* growth by pfDHODH inhibitors and known antimalarials.

| Compound | Structure | pfDHODH IC50 uM | 3D7 EC50 uM | Dd2 EC50 uM |
|---|---|---|---|---|
| 24 | 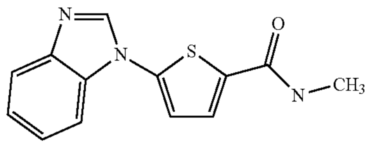 [SMILES: CNC(=O)c1ccc(-n2cnc3ccccc32)s1] | 1.076 (Hu: >30) | 0.276 | 0.422 |
| 25 | 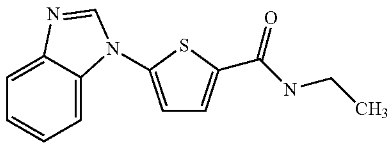 [SMILES: CCNC(=O)c1ccc(-n2cnc3ccccc32)s1] | 0.145 (Hu: >30) | 0.102 | 0.154 |
| 26 | 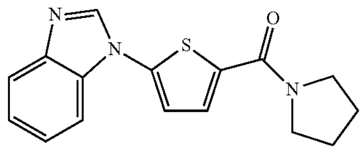 [SMILES: O=C(c1ccc(-n2cnc3ccccc32)s1)N1CCCC1] | >30 | 10 | 20 |
| 27 | 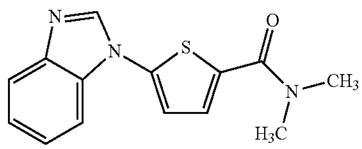 [SMILES: CN(C)C(=O)c1ccc(-n2cnc3ccccc32)s1] | >30 | >40 | >40 |
| 28 | 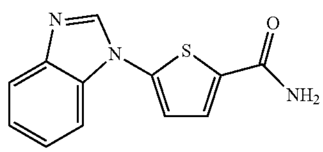 [SMILES: NC(=O)c1ccc(-n2cnc3ccccc32)s1] | >30 | >40 | 20 |
| 29 | 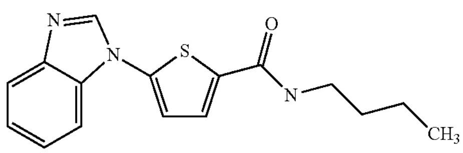 [SMILES: CCCCNC(=O)c1ccc(-n2cnc3ccccc32)s1] | 28.6 | 20 | 7.3 |
| 30 | 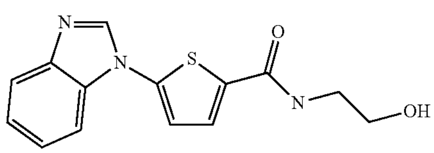 [SMILES: O=C(NCCO)c1ccc(-n2cnc3ccccc32)s1] | 14.0 (Hu: >30) | 5.9 | 6.5 |
| 31 | 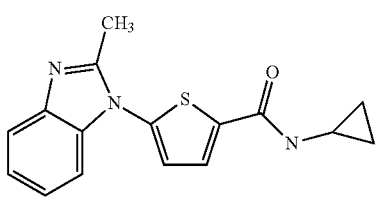 [SMILES: Cc1nc2ccccc2n1-c1ccc(C(=O)NC2CC2)s1] | 0.099 (Hu: >30) | 0.066 | 0.106 |
| 32 | 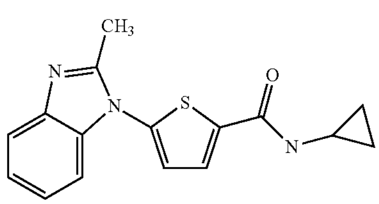 [SMILES: Cc1nc2ccccc2n1-c1ccc(C(=O)NC2CC2)s1] | 0.074 (Hu: >30) | 0.105 | 0.114 |

TABLE 2b-continued

Inhibition of *P. falciparum* growth by pfDHODH inhibitors and known antimalarials.

| Compound | Structure | pfDHODH IC50 uM | 3D7 EC50 uM | Dd2 EC50 uM |
|---|---|---|---|---|
| 33 | 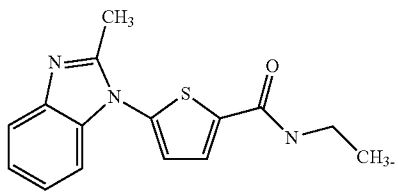 | 0.191 (Hu: >30) | 0.113 | 0.223 |
| 34 | 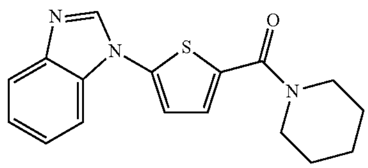 [SMILES: O=C(c1ccc(-n2cnc3ccccc32)s1)N1CCCCC1] | >30 | >20 | >20 |
| 35 | 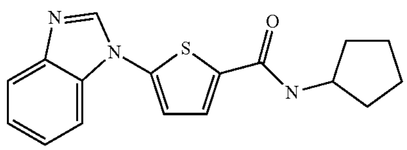 [SMILES: O=C(NC1CCCC1)c1ccc(-n2cnc3ccccc32)s1] | 2.506 (Hu: >30) | 4.4 | 5.5 |
| 36 | 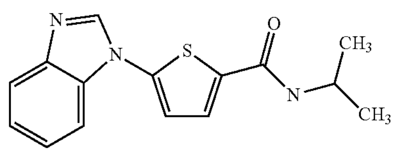 [SMILES: CC(C)NC(=O)c1ccc(-n2cnc3ccccc32)s1] | 0.684 (Hu: >30) | 0.579 | 0.812 |
| 37 | 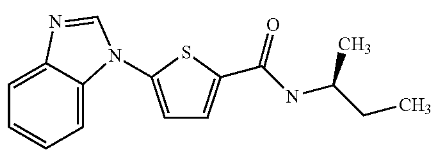 [SMILES: CC[C@H](C)NC(=O)c1ccc(-n2cnc3ccccc32)s1] | 17.9 | >20 | >20 |
| 38 | 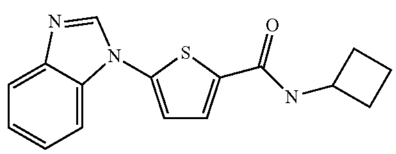 [SMILES: O=C(NC1CCC1)c1ccc(-n2cnc3ccccc32)s1] | 0.418 (Hu: >30) | 0.408 | 0.442 |
| 39 | 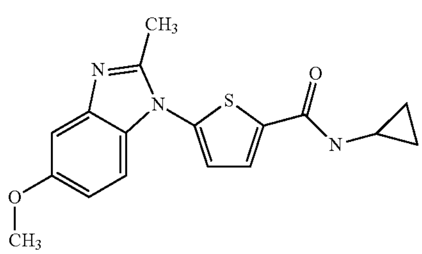 [SMILES: COc1ccc2c(c1)nc(C)n2-c1ccc(C(=O)NC2CC2)s1] | 0.212 (Hu: 24.6) | 0.180 | 0.247 |
| 40 | 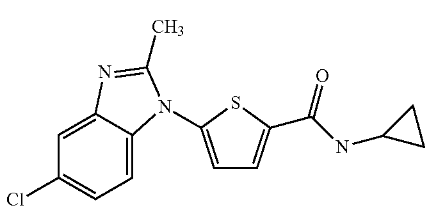 [SMILES: Cc1nc2cc(Cl)ccc2n1-c1ccc(C(=O)NC2CC2)s1] | 0.058 (Hu: >30) | 0.088 | 0.120 |

TABLE 2b-continued

Inhibition of *P. falciparum* growth by pfDHODH inhibitors and known antimalarials.

| Compound | Structure | pfDHODH IC50 uM | 3D7 EC50 uM | Dd2 EC50 uM |
|---|---|---|---|---|
| 41 | 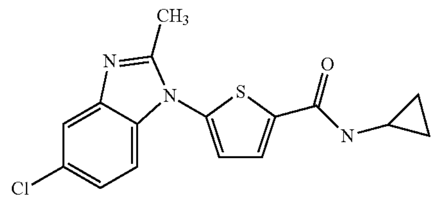 [SMILES: Cc1nc2cc(Cl)ccc2n1-c1ccc(C(=O)NC2CC2)s1] | 0.040 (Hu: >30) | 0.067 | 0.083 |
| 42 | 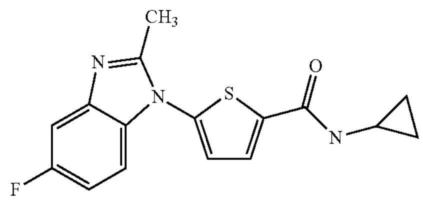 [SMILES: Cc1nc2cc(F)ccc2n1-c1ccc(C(=O)NC2CC2)s1] | 0.088 (Hu: >30) | 0.104 | 0.150 |
| 43 | 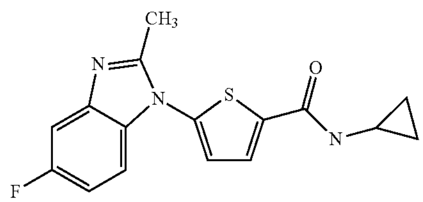 [SMILES: Cc1nc2cc(F)ccc2n1-c1ccc(C(=O)NC2CC2)s1] | 0.104 (Hu:20.3) | 0.039 | 0.036 |
| 44 | 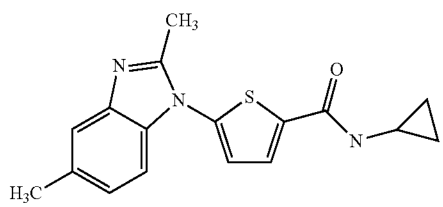 [SMILES: Cc1ccc2c(c1)nc(C)n2-c1ccc(C(=O)NC2CC2)s1] | 0.056 (Hu: >30) | 0.034 | 0.048 |
| 45 | 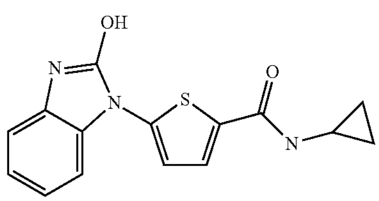 [SMILES: O=C(NC1CC1)c1ccc(-n2c(O)nc3ccccc32)s1] | >30 | 5 | 5 |
| 46 | 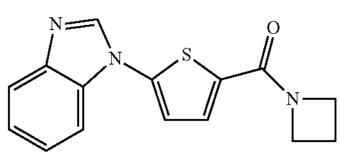 [SMILES: O=C(c1ccc(-n2cnc3ccccc32)s1)N1CCC1] | 16.5 | 5 | 5 |
| 47 | 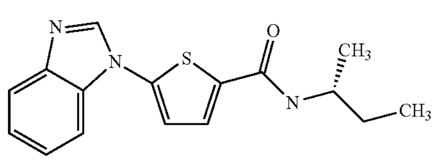 [SMILES: CC[C@@H](C)NC(=O)c1ccc(-n2cnc3ccccc32)s1] | >30 | >5 | >5 |

TABLE 2b-continued
Inhibition of P. falciparum growth by pfDHODH inhibitors and known antimalarials.
| Compound | Structure | pfDHODH IC50 uM | 3D7 EC50 uM | Dd2 EC50 uM |
|---|---|---|---|---|
| 48 | 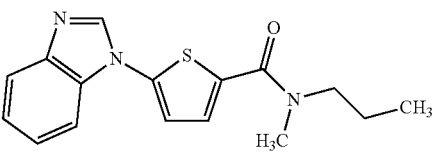 [SMILES: CCCN(C)C(=O)c1ccc(-n2cnc3ccccc32)s1] | >30 | >5 | >5 |
| 49 | 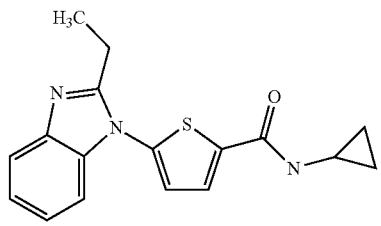 [SMILES: CCc1nc2ccccc2n1-c1ccc(C(=O)NC2CC2)s1] | 0.113 (Hu: >30) | 0.125 | 0.185 |
| 50 | 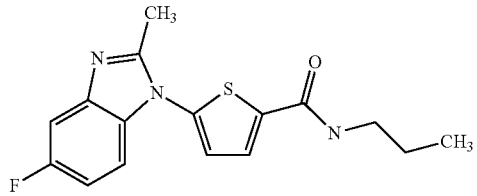 [SMILES: CCCNC(=O)c1ccc(-n2c(C)nc3cc(F)ccc32)s1] | 0.499 (Hu: >30) | 0.255 | 0.538 |
| 51 | 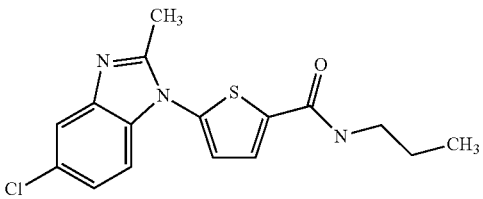 [SMILES: CCCNC(=O)c1ccc(-n2c(C)nc3cc(Cl)ccc32)s1] | 0.239 (Hu: >30) | 0.158 | 0.314 |
| 52 | 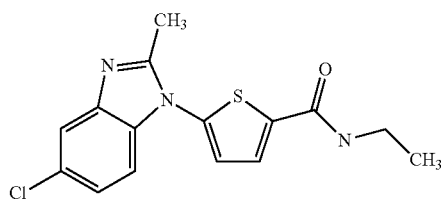 [SMILES: CCNC(=O)c1ccc(-n2c(C)nc3cc(Cl)ccc32)s1] | 0.094 (Hu: >30) | 0.053 | 0.104 |
| 53 | 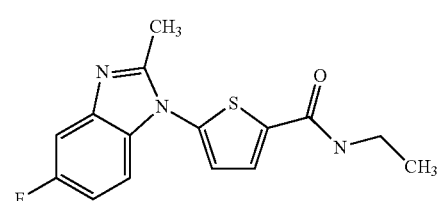 | 0.164 (Hu: >30) | 0.066 | 0.106 |
| 54 | 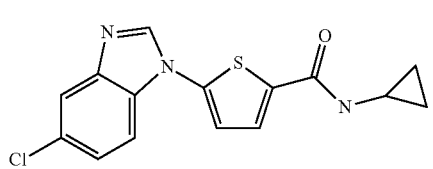 [SMILES: O=C(NC1CC1)c1ccc(-n2cnc3cc(Cl)ccc32)s1] | 0.166 (Hu: >30) | 0.060 | 0.116 |

TABLE 2b-continued

Inhibition of *P. falciparum* growth by pfDHODH inhibitors and known antimalarials.

| Compound | Structure | pfDHODH IC50 uM | 3D7 EC50 uM | Dd2 EC50 uM |
|---|---|---|---|---|
| 55 | 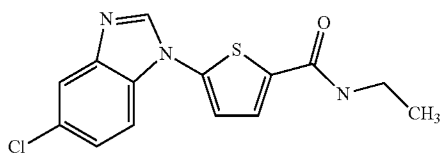 [SMILES: CCNC(=O)c1ccc(-n2cnc3cc(Cl)ccc32)s1] | 0.056 (Hu: 25.1) | 0.028 | 0.050 |
| 56 | 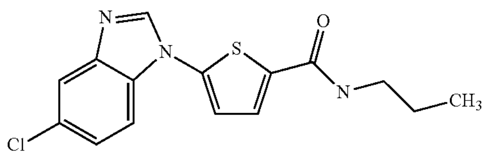 [SMILES: CCCNC(=O)c1ccc(-n2cnc3cc(Cl)ccc32)s1] | 0.324 (Hu: >30) | 0.203 | Not done |
| 57 | 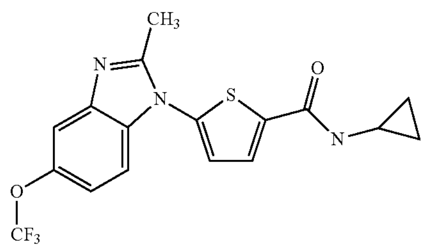 [SMILES: Cc1nc2cc(OC(F)(F)F)ccc2n1-c1ccc(C(=O)NC2CC2)s1] | 0.064 (Hu: >30) | 0.033 | 0.060 |
| 58 | 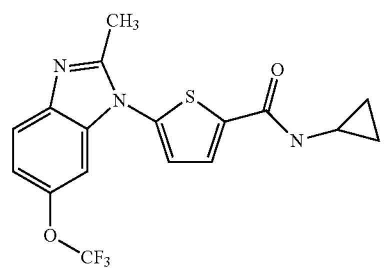 [SMILES: Cc1nc2ccc(OC(F)(F)F)cc2n1-c1ccc(C(=O)NC2CC2)s1] | 0.036 (Hu: >30) | 0.009 | 0.016 |
| 59 | 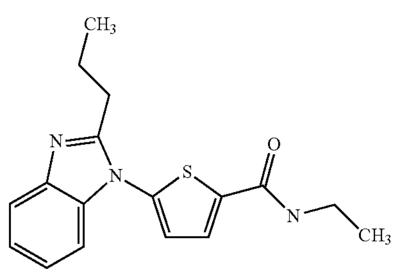 [SMILES: CCCc1nc2ccccc2n1-c1ccc(C(=O)NCC)s1] | 0.334 (Hu: 19.4) | 0.382 | 0.467 |
| 60 | 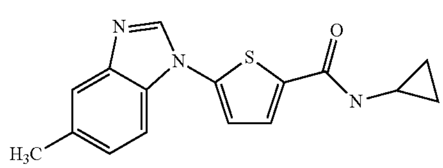 [SMILES: Cc1ccc2c(c1)ncn2-c1ccc(C(=O)NC2CC2)s1] | 0.038 (Hu: 24.6) | 0.020 | 0.021 |
| 61 | 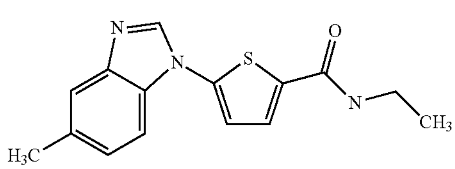 [SMILES: CCNC(=O)c1ccc(-n2cnc3cc(C)ccc32)s1] | 0.075 (Hu: 21.2) | 0.027 | 0.039 |

TABLE 2b-continued

Inhibition of *P. falciparum* growth by pfDHODH inhibitors and known antimalarials.

| Compound | Structure | pfDHODH IC50 uM | 3D7 EC50 uM | Dd2 EC50 uM |
|---|---|---|---|---|
| 62 | 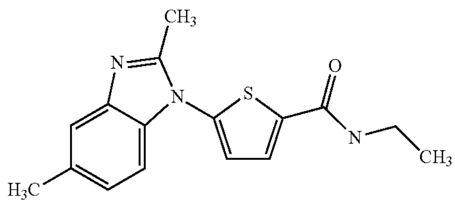 [SMILES: CCNC(=O)c1ccc(-n2c(C)nc3cc(C)ccc32)s1] | 0.112 (Hu: >30) | 0.089 | 0.087 |
| 63 | 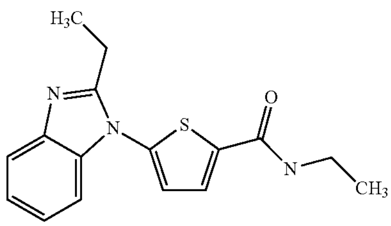 [SMILES: CCNC(=O)c1ccc(-n2c(CC)nc3ccccc32)s1] | 0.137 (Hu: >30) | 0.141 | 0.146 |
| 64 | 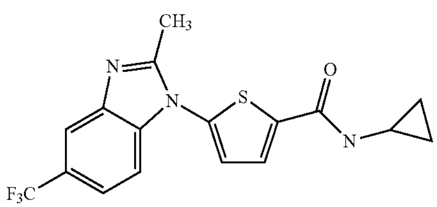 [SMILES: Cc1nc2cc(C(F)(F)F)ccc2n1-c1ccc(C(=O)NC2CC2)s1] | 0.041 (Hu: 28.0) | 0.008 | 0.012 |
| 65 | 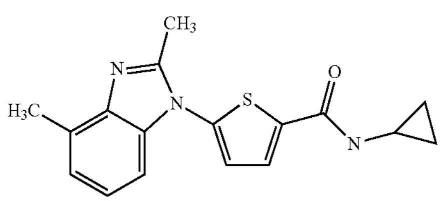 [SMILES: Cc1cccc2c1nc(C)n2-c1ccc(C(=O)NC2CC2)s1] | 0.042 (Hu: >30) | 0.009 | 0.013 |
| 66 | 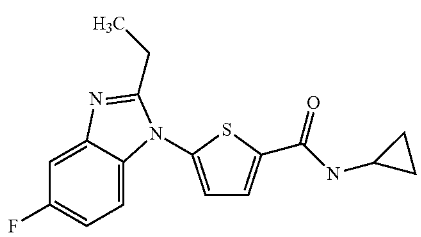 [SMILES: CCc1nc2cc(F)ccc2n1-c1ccc(C(=O)NC2CC2)s1] | 0.067 (Hu: >30) | 0.136 | 0.253 |
| 67 | 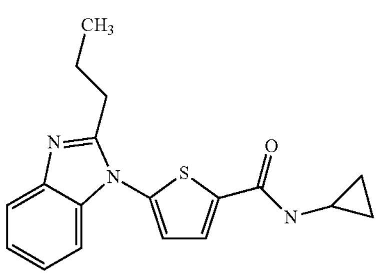 [SMILES: CCCc1nc2ccccc2n1-c1ccc(C(=O)NC2CC2)s1] | 0.180 (Hu: 25.6) | 0.389 | 0.629 |

TABLE 2b-continued

Inhibition of *P. falciparum* growth by pfDHODH inhibitors and known antimalarials.

| Compound | Structure | pfDHODH IC50 uM | 3D7 EC50 uM | Dd2 EC50 uM |
| --- | --- | --- | --- | --- |
| 68 | 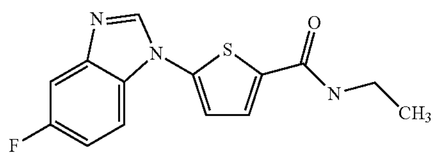 [SMILES: CCNC(=O)c1ccc(-n2cnc3cc(F)ccc32)s1] | 0.105 (Hu: >30) | 0.090 | 0.132 |
| 69 | 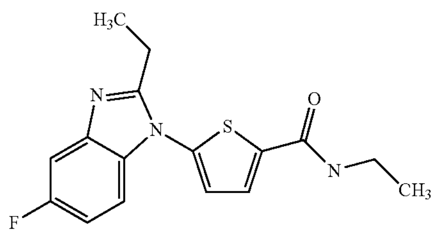 [SMILES: CCNC(=O)c1ccc(-n2c(CC)nc3cc(F)ccc32)s1] | 0.178 (Hu: >30) | 0.226 | 0.361 |
| 70 | 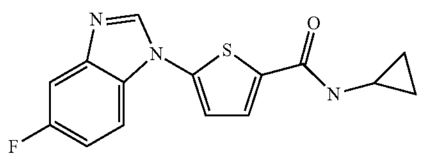 [SMILES: O=C(NC1CC1)c1ccc(-n2cnc3cc(F)ccc32)s1] | 0.058 (Hu: >30) | 0.062 | 0.105 |
| 71 | 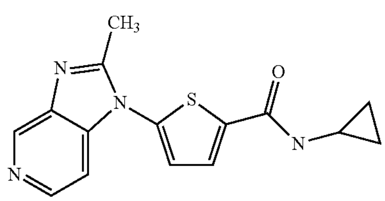 [SMILES: Cc1nc2cnccc2n1-c1ccc(C(=O)NC2CC2)s1] | 3.084 | 3.7 | 6.3 |
| 72 | 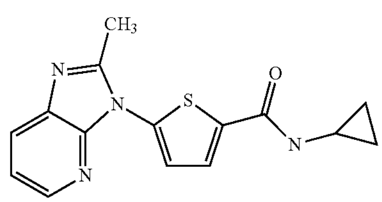 | 1.118 | 0.364 | 0.520 |
| 73 | 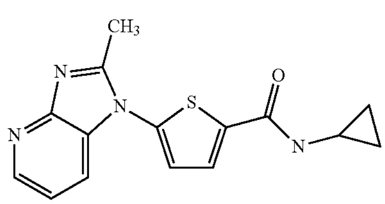 [SMILES: Cc1nc2ncccc2n1-c1ccc(C(=O)NC2CC2)s1] | 4.766 | 1.3 | 2.4 |
| 74 | 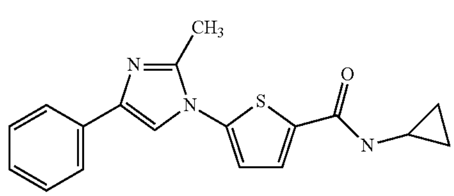 [SMILES: Cc1nc(-c2ccccc2)cn1-c1ccc(C(=O)NC2CC2)s1] | 0.220 (Hu: >30) | 0.124 | 0.206 |

TABLE 2b-continued

Inhibition of *P. falciparum* growth by pfDHODH inhibitors and known antimalarials.

| Compound | Structure | pfDHODH IC50 uM | 3D7 EC50 uM | Dd2 EC50 uM |
|---|---|---|---|---|
| 75 | 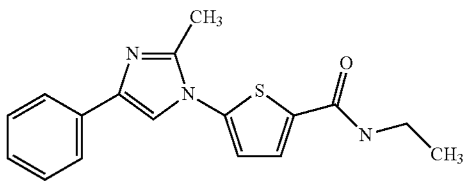 [SMILES: CCNC(=O)c1ccc(-n2cc(-c3ccccc3)nc2C)s1] | 0.416 (Hu: >30) | 0.278 | 0.283 |
| 76 | 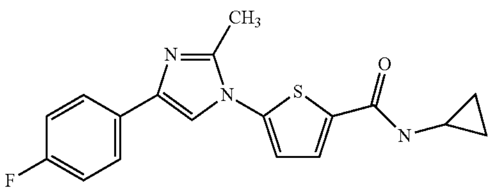 [SMILES: Cc1nc(-c2ccc(F)cc2)cn1-c1ccc(C(=O)NC2CC2)s1] | 0.240 (Hu: >30) | 0.226 | 0.217 |
| 77 | 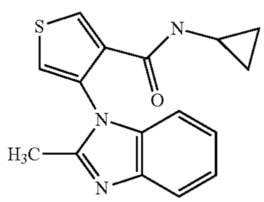 [SMILES: Cc1nc2ccccc2n1-c1cscc1C(=O)NC1CC1] | >30 | >5 | >5 |
| 78 | 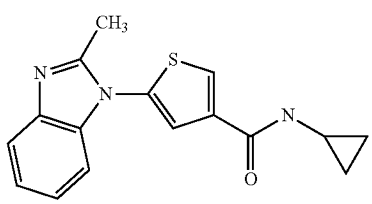 [SMILES: Cc1nc2ccccc2n1-c1cc(C(=O)NC2CC2)cs1] | 1.7 | 1.017 | 2.051 |
| 79 | 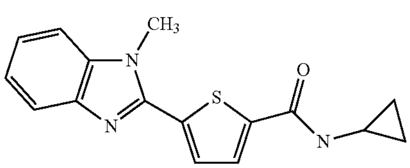 [SMILES: Cn1c(-c2ccc(C(=O)NC3CC3)s2)nc2ccccc21] | >30 | >5 | >5 |
| 80 | 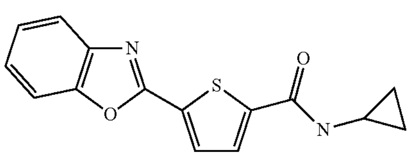 [SMILES: O=C(NC1CC1)c1ccc(-c2nc3ccccc3o2)s1] | >30 | 2.584 | 1.706 |
| 81 | 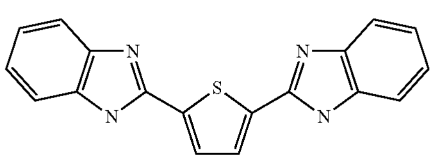 [SMILES: c1ccc2[nH]c(-c3ccc(-c4nc5ccccc5[nH]4)s3)nc2c1] | >30 | 5 | >5 |
| 82 | 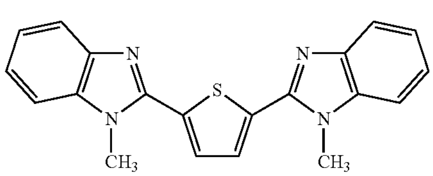 [SMILES: Cn1c(-c2ccc(-c3nc4ccccc4n3C)s2)nc2ccccc21] | >30 | >5 | >5 |

TABLE 2b-continued

Inhibition of *P. falciparum* growth by pfDHODH inhibitors and known antimalarials.

| Compound | Structure | pfDHODH IC50 uM | 3D7 EC50 uM | Dd2 EC50 uM |
|---|---|---|---|---|
| 83 | 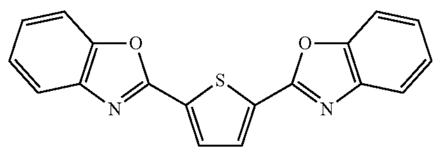 [SMILES: c1ccc2oc(-c3ccc(-c4nc5ccccc5o4)s3)nc2c1] | >30 | >5 | >5 |
| 84 | 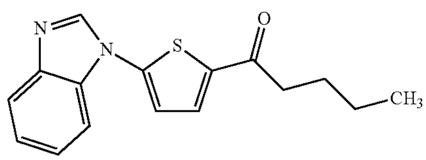 [SMILES: CCCCC(=O)c1ccc(-n2cnc3ccccc32)s1] | >30 (Hu: >30) | >40 | 20 |
| 85 | 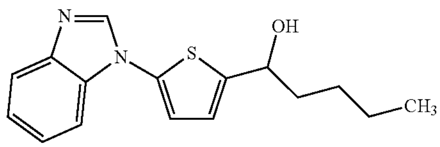 [SMILES: CCCCC(O)c1ccc(-n2cnc3ccccc32)s1] | >30 | 20 | 5.9 |
| 86 | 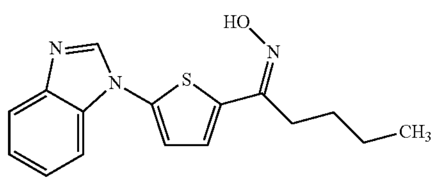 [SMILES: CCCC/C(=N/O)c1ccc(-n2cnc3ccccc32)s1] | >30 | 10 | 20 |
| 87 | 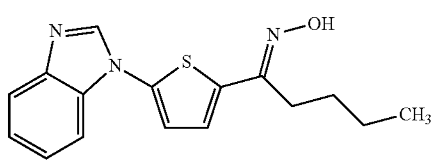 [SMILES: CCCC/C(=N\O)c1ccc(-n2cnc3ccccc32)s1] | >30 | 40 | 10 |
| 88 | 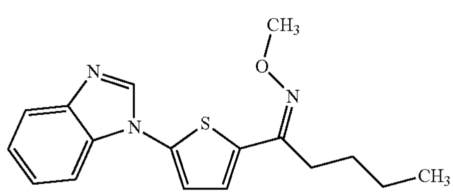 [SMILES: CCCC/C(=N/OC)c1ccc(-n2cnc3ccccc32)s1] | >30 | 5.4 | 2.6 |
| 89 | 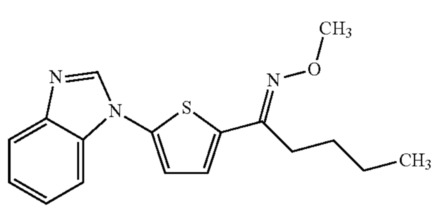 [SMILES: CCCC/C(=N\OC)c1ccc(-n2cnc3ccccc32)s1] | >30 | 5.3 | 4.4 |

TABLE 2b-continued

*Inhibition of P. falciparum growth by pfDHODH inhibitors and known antimalarials.*

| Compound | Structure | pfDHODH IC50 uM | 3D7 EC50 uM | Dd2 EC50 uM |
|---|---|---|---|---|
| 90 | 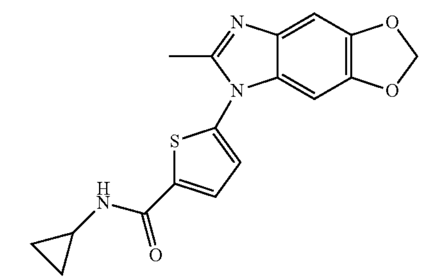 [SMILES: Cc1nc2cc3c(cc2n1-c1ccc(C(=O)NC2CC2)s1)OCO3] | 0.116 (Hu: >30) | 0.220 | 0.174 |
| 91 | 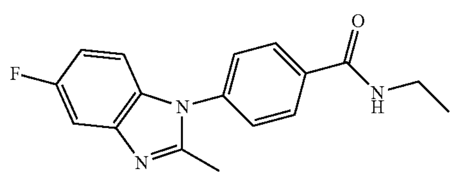 [SMILES: CCNC(=O)c1ccc(-n2c(C)nc3cc(F)ccc32)cc1] | 2.870 | >0.5 | >0.5 |
| 92 | 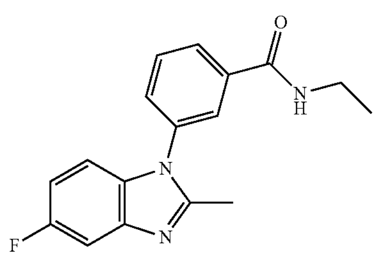 [SMILES: CCNC(=O)c1cccc(-n2c(C)nc3cc(F)ccc32)c1] | >30 | >1 | >1 |
| 93 | 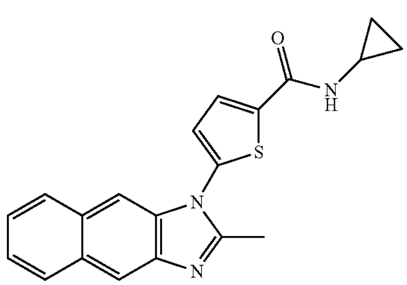 [SMILES: Cc1nc2cc3ccccc3cc2n1-c1ccc(C(=O)NC2CC2)s1] | 0.035 | 0.017 | 0.019 |
| 94 | 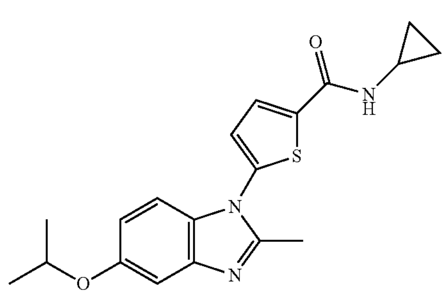 [SMILES: Cc1nc2cc(OC(C)C)ccc2n1-c1ccc(C(=O)NC2CC2)s1] | 0.121 | 0.051 | 0.061 |

TABLE 2b-continued
Inhibition of *P. falciparum* growth by pfDHODH inhibitors and known antimalarials.
| Compound | Structure | pfDHODH IC50 uM | 3D7 EC50 uM | Dd2 EC50 uM |
|---|---|---|---|---|
| 95 | 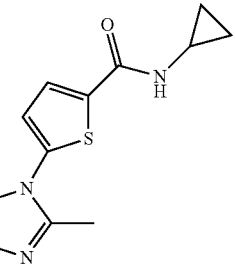 | 0.105 | | |
| 96 | 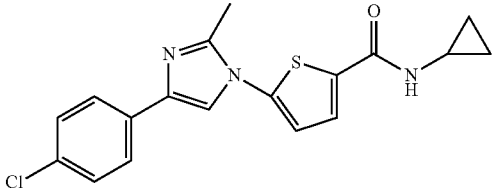 [SMILES: Cc1nc(-c2ccc(Cl)cc2)cn1-c1ccc(C(=O)NC2CC2)s1] | 0.252 | | |
| 97 | 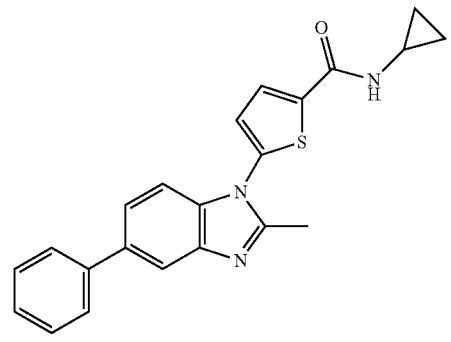 [SMILES: Cc1nc2cc(-c3ccccc3)ccc2n1-c1ccc(C(=O)NC2CC2)s1] | 0.178 | | |
| 98 | 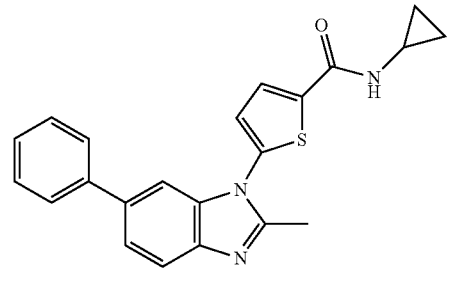 [SMILES: Cc1nc2ccc(-c3ccccc3)cc2n1-c1ccc(C(=O)NC2CC2)s1] | 0.089 | | |
| 99 | 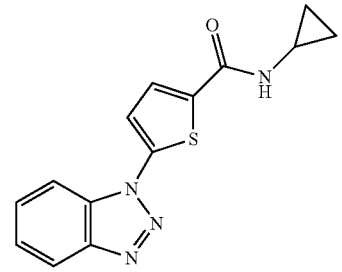 [SMILES: O=C(NC1CC1)c1ccc(-n2nnc3ccccc32)s1] | 28.0 | | |

TABLE 2b-continued

Inhibition of *P. falciparum* growth by pfDHODH inhibitors and known antimalarials.

| Compound | Structure | pfDHODH IC50 uM | 3D7 EC50 uM | Dd2 EC50 uM |
|---|---|---|---|---|
| 100 | 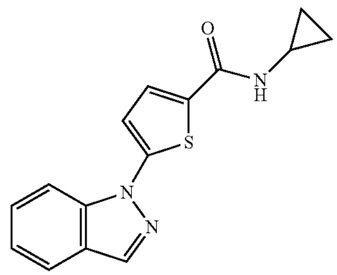 [SMILES: O=C(NC1CC1)c1ccc(-n2ncc3ccccc32)s1] | >30 | | |

Compounds similar in structure to Compound 1 were synthesized as described in Example 1 and were tested for their ability to inhibit in vitro cultures of 3D7 and Dd2 *P. falciparum* strains, and their $IC_{50}$ values are reported in Table 3.

TABLE 3

Structure-activity relationship of Compound 1 and Derivative Compounds.

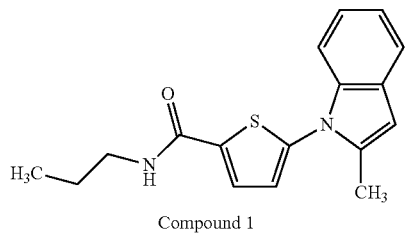

Compound 1

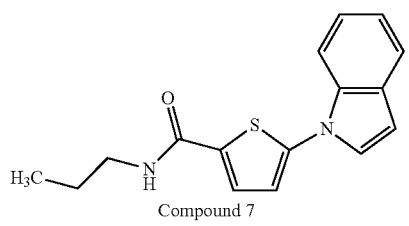

Compound 7

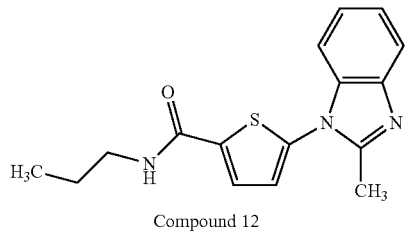

Compound 12

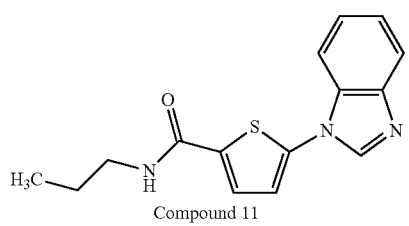

Compound 11

TABLE 3-continued

Structure-activity relationship of Compound 1 and Derivative Compounds.

Compound 8

Compound 10

Compound 9

| Compound Number | Inhibitory Activity | | 3D7 | Dd2 | Physical Properties | | |
|---|---|---|---|---|---|---|---|
| | pfDHODH $IC_{50}$ (μM)[1] | hsDHODH $IC_{50}$ (μM)[1] | $IC_{50}$ (μM)[2] | $IC_{50}$ (μM)[2] | Solubility (μg/mL) | Permeability (cm/sec × $10^{-6}$) | LogD |
| 1 | 0.07 | >30 | 0.39 | 0.25 | 0.9 | 0 | >3.5 |
| 7 | 0.46 | >30 | 0.71 | 0.23 | 1 | 52 | >3.5 |
| 8 | >30 | >30 | >10 | >10 | >30 | 43 | 3.2 |
| 9 | >30 | >30 | >10 | >10 | >30 | 22 | 2.2 |
| 10 | >30 | >30 | >10 | >10 | 24 | 11 | 1.5 |
| 11 | 0.7 | >30 | 0.47 | 0.955 1.25 | >30 | 32 | 3.3 |
| 12 | 0.17 | >30 | 0.63 | | >30 | 65 | 3.4 |

[1]Enzymatic $IC_{50}$ values were determined using the DCIP assay where the reagent concentrations were 200 μM L-DHO, 18 μM $CoQ_D$, and 100 μM DCIP, and 20 nM pfDHODH or hsDHODH.
[2]$IC_{50}$ values were calculated from dose-effect curves based upon the relative reduction of [$^3$H]–hypoxanthine uptake by parasite infected erythrocytes.

The relationship between the structure of the DHODH inhibitor and its inhibition activity and physical properties is summarized in Table 3. The inhibition data of these compounds showed that the indole moiety of the Compound 1 could be replaced with a benzimidazolyl ring system, such as in Compound 12, to significantly enhance the physical properties of the molecule while retaining anti-malarial activity. No adverse cytotoxicity to Compound 12 was apparent in kidney epithelial cells or dermal fibroblasts (see Example 9, Table 5).

Physical Properties
Solubility Measurements

Many standard techniques are known in the art to establish the solubility of a compound in a particular solvent. The following description is one such technique that could be used to determine the solubility:

Equilibrium solubility measurements start with the solid form of the compound (crystalline form preferred). The powder is physically mixed with an aqueous buffer (defined pH) until equilibrium is reached. Either centrifugation or filtration can be used to separate the solution from the remaining solid. The amount dissolved in the solution can be determined by any one of many known methods including HPLC or UV/Vis spectroscopic techniques.

Log D Measurements

Many standard techniques are known in the art to establish the distribution coefficient of a compound between two particular solvents. The following description is one such technique that could be used to determine the distribution coefficient:

The shake-flask method, which consists of dissolving some of the compound in a volume of octanol and water, then physically shaking the mixture and allowing the two solvents to fully separate. The concentration of the compound in each solvent is then measured. The most common method of measuring the distribution of the solute is by HPLC or UV/Vis spectroscopic techniques.

Permeability

Permeability assays using the Caco-2 colon carcinoma cell line are being used throughout the pharmaceutical industry to estimate the ability of potential drug compounds to cross the intestinal epithelium. Caco-2 cell permeability studies are performed using Caco-2 cell monolayers grown on microporous membranes in multiwell insert systems. With the inserts suspended in the wells of multiwell plates, test compounds can be added to either the upper (apical) or lower (basolateral) chamber to measure permeability in the absorptive (apical to basolateral) or secretive (basolateral to apical) directions. Samples are then taken from the opposite chamber at various time intervals to measure the amount of test compound that has crossed the cell monolayer. A representative method to generate permeability data similar to that in Table 3 can be found in Alsenz, J; Haenel, E. "Development of a 7-Day, 96-Well Caco-2 Permeability Assay with High-Throughput Direct UV Compound Analysis." *Pharmaceutical Research* 2003 20(12): p 1961-1969.

Parallel artificial membrane permeability assay (PAMPA) utilizes a simple phospholipid-coated filter disc to measure membrane permeability. It was developed as an alternative to the low throughput. Caco-2 cell permeability assay used to correlate passive permeability with in vivo oral absorption. A representative publication disclosing this method is Kerns, E H; Di, L; Petusky, S; Farris, M; Ley, R; Jupp, P. "Combined application of parallel artificial membrane permeability assay and Caco-2 permeability assays in drug discovery." *J. Pharma Sci.* 2004, 93 (6), pages 1440-53.

Cell culture methods (e.g. Caco-2, HT-29 and MDC) and physicochemical methods such as PAMPA and immobilized artificial membrane (IAM) columns are known in the art and can be used to obtain data such as that in Table 3. Hidalgo, I J; "Assessing the absorption of new pharmaceuticals." *Curr Top Med. Chem.* 2001 November; 1(5): p 385-401.

Example 5

Mechanism of pfDHODH Inhibition

Determination of meaningful inhibition constants by steady-state kinetic analysis is usually difficult when examining two-substrate enzymatic reactions, this is further complicated when studying a ping-pong mechanism such as that catalyzed by DHODH. Malmquist et al. [47] demonstrated that the $K_m^{app}$ for $CoQ_n$ to pfDHODH, as determined by the direct assay, likely reflects multiple kinetic steps and thus, does not necessarily mimic the true $K_m$. It was previously shown that in the absence of $CoQ_n$, the nonspecific inorganic oxidants ferricyanide (FeCy) or $O_2$ can re-oxide the FMN cofactor presumably via an alternative electron-transfer pathway [47]. Therefore, the ability of the six quaternary hits from the HTS to inhibit pfDHODH using FeCy as the terminal electron acceptor was examined. None of the compounds significantly inhibited this reaction at a concentration of 50 µM (Table 4).

TABLE 4

Inhibition of pfDHODH activity by quaternary hits from the HTS using $CoQ_D$ and FeCy as electron acceptors.

| Compound # | % Inhibition of Product Formation Rate with 50 µM Inhibitor | |
|---|---|---|
| | $CoQ_D$[1] | FeCy[2] |
| 1 | 104 | 31 |
| 2 | 94 | 1.2 |
| 3 | 100 | 17 |
| 4 | 97 | 7.7 |
| 5 | 97 | 23 |
| 6 | 102 | 4.8 |

[1]The rate of orotate formation was quantified with the coupled dye assay that measures the reduction of DCIP with an initial substrate concentration of 200 µM L-DHO, 100 µM $CoQ_D$, and 60 µM DCIP.
[2]The reduction of FeCy was measured continuously noting that two molecules of FeCy are reduced for each molecule of L-DHO. The substrate concentration was 200 µM L-DHO and 100 µM FeCy.

The inhibitory action of A77 1726 against the hsDHODH activity, with FeCy as the final electron acceptor, was minimal in contrast to complete inhibition of catalysis afforded when using $CoQ_n$ as the second substrate. This inability to inhibit DHODH activity when electrons are transferred from FMN to FeCy, suggests a mechanism of inhibition that is specific to the transfer of electrons from FMN to $CoQ_n$ such as an inhibitor sitting in the long, hydrophobic tunnel. To the best of our knowledge, this is first example of an HTS for pfDHODH inhibitors that has yielded candidate drugs that are specific for the *Plasmodium* enzyme and are efficacious against cultured malaria parasites. Our findings confirm the utility of pfDHODH as a target for anti-malarial chemotherapy.

Example 6

Target Validation of pfDHODH Inhibitors

A transgenic *P. falciparum* strain expressing a Type 1 DHODH from *S. cerevisiae* in addition to the endogenous mitochondrial pfDHODH was used to establish that pfDHODH was a likely mechanism of inhibition for the quaternary hits.

Figure 5A:
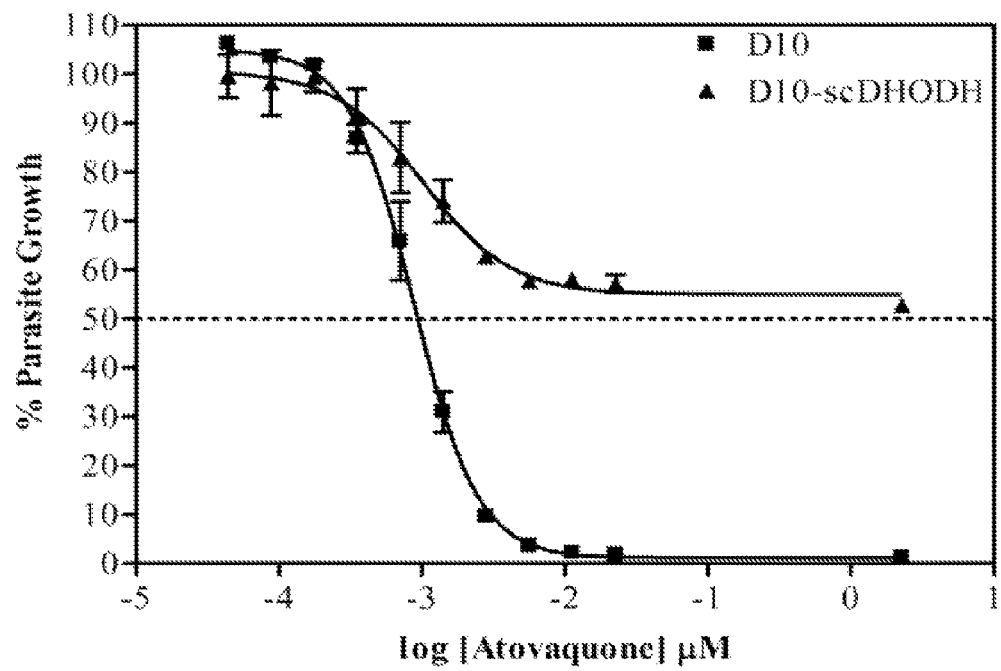
Figure 5A:
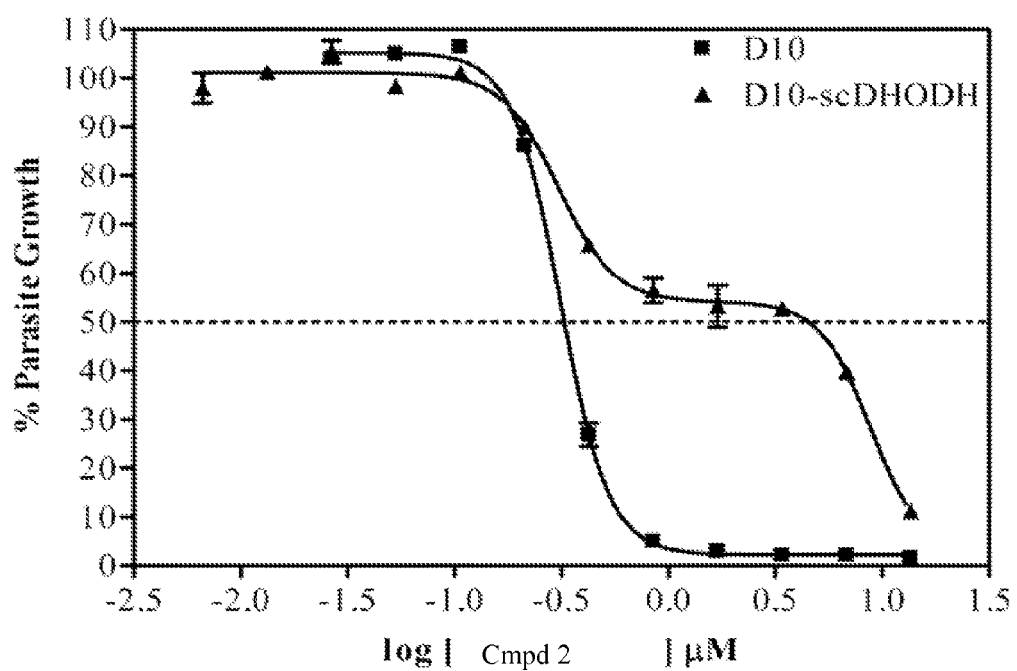
Figure 5B:
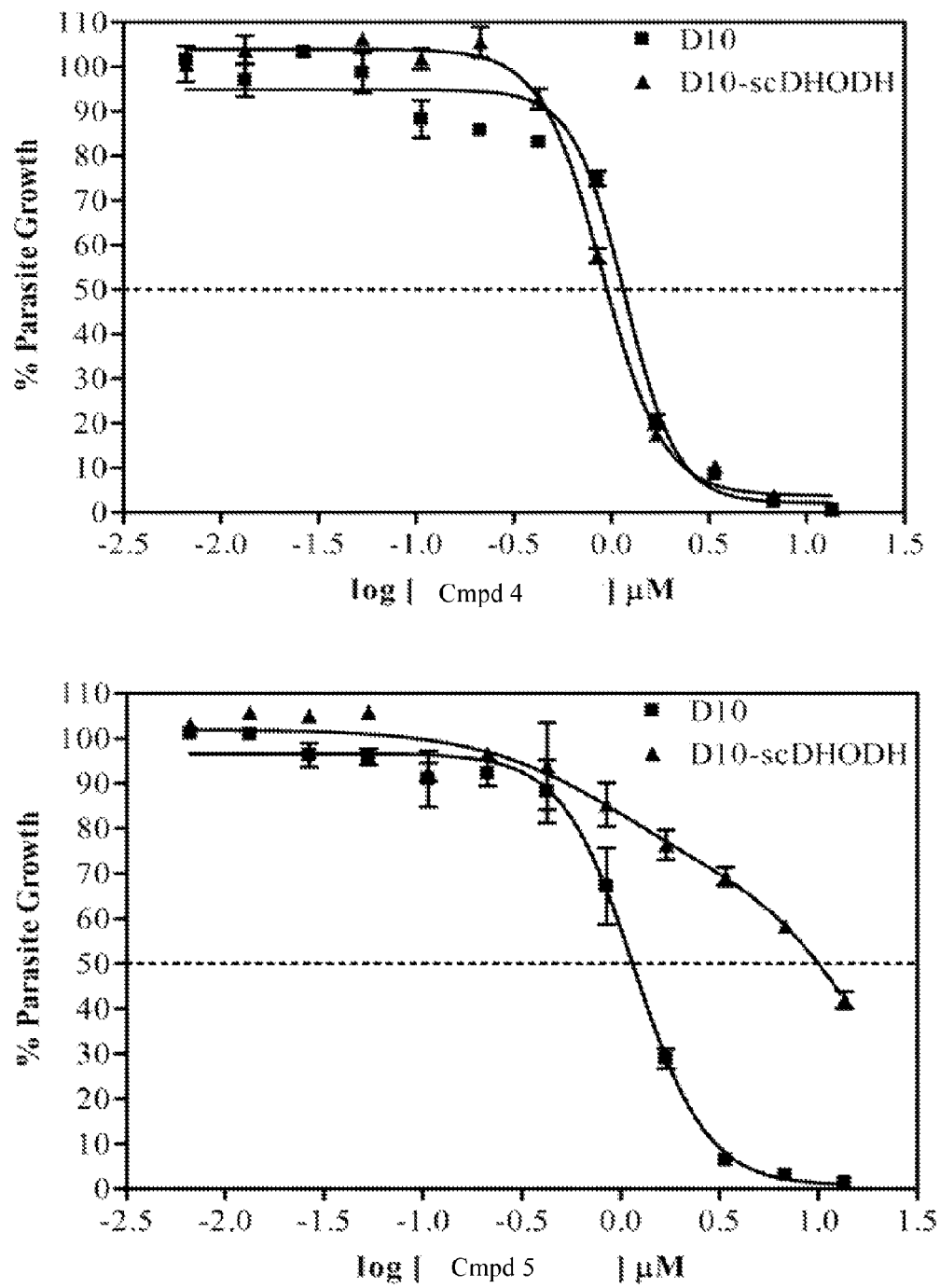
Figure 5C:
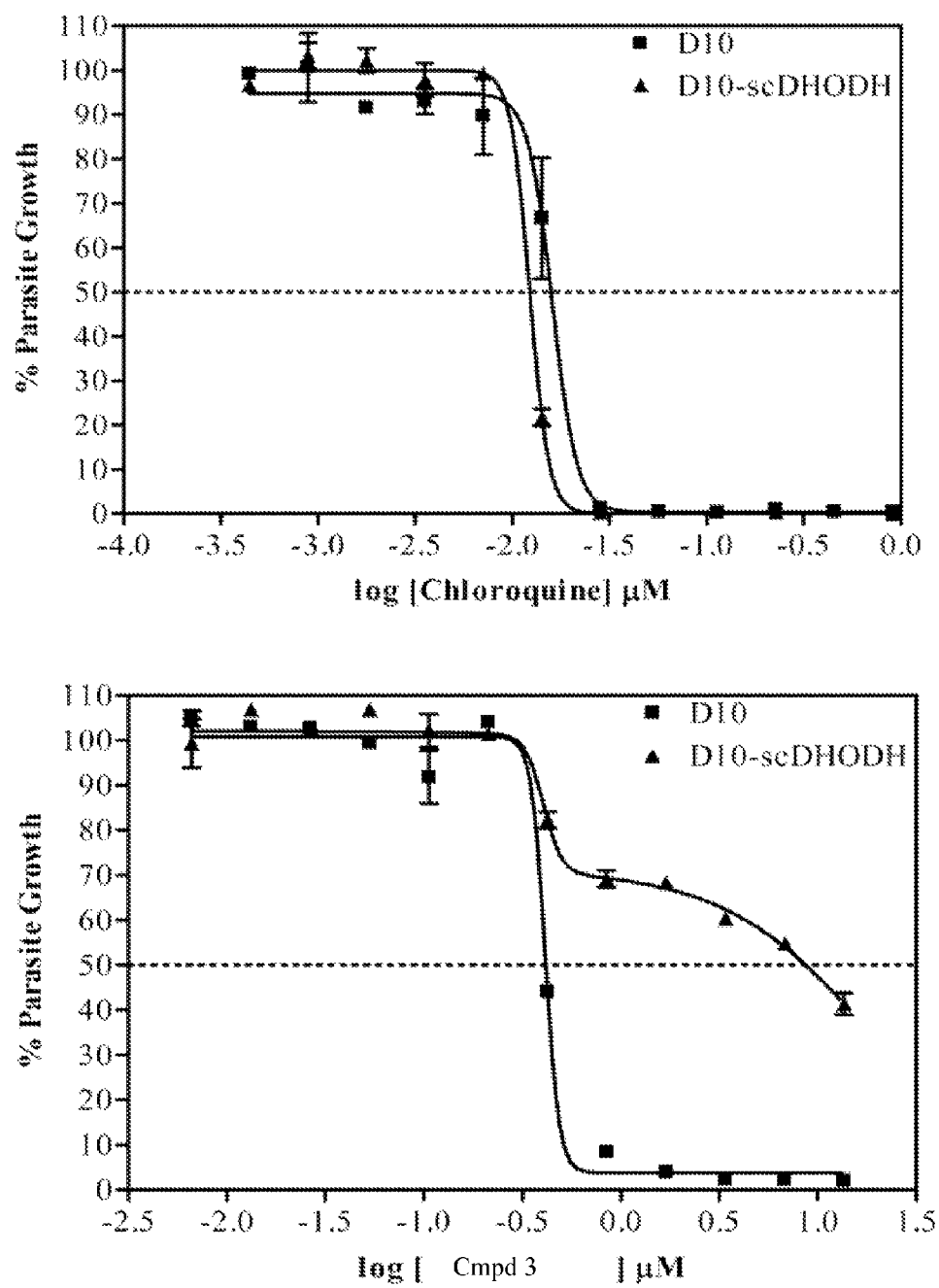
Figure 5D:
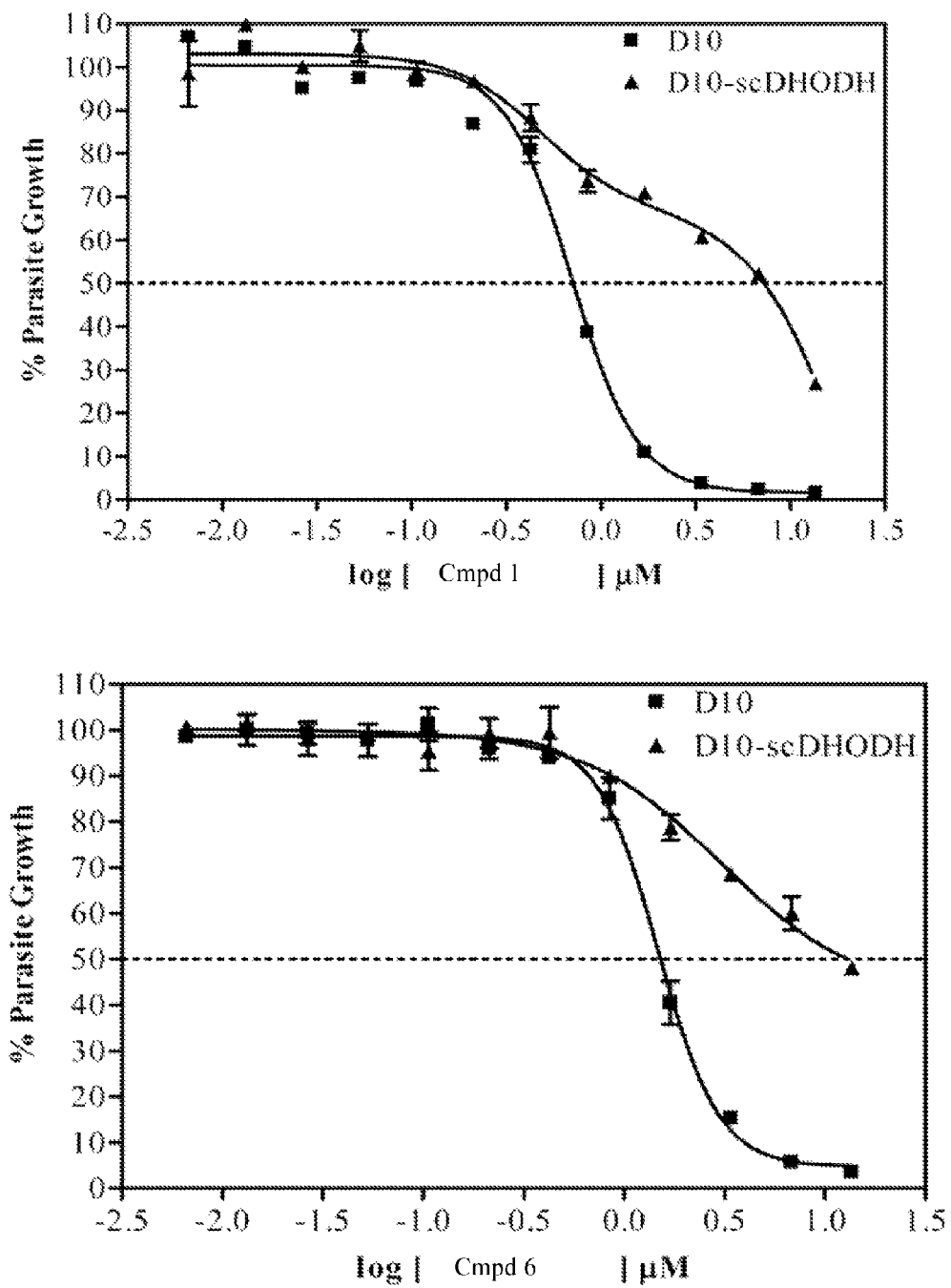

Painter et al [28] had previously shown in an analogous experiment that the role of the mitochondrial electron chain, maintained in part by the cytochrom $bc_1$ complex, in the asexual stage of *P. falciparum* growth was mainly to re-oxidize $CoQ_n$ to sustain pfDHODH activity and subsequent de novo pyrimidine biosynthesis [28,48]. Consistent with this premise, the dose-effect curve for the D10-scDHODH parasite strain grown in the presence of atovaquone, an inhibitor of the 9 $bc_1$ complex, demonstrated significantly reduced drug efficacy when compared to the D10 parent strain (FIG. 5A). Complete resistance to atovaquone was not observed; this is most likely due to variations in copy number of the scDHODH expression plasmid among the transgenic parasite population. Nevertheless, the D10-scDHODH parasite strain was effectively engineered to largely bypass the pfDHODH pathway. Unrelated biochemical pathways such as heme polymerization were not affected given that both strains remained equally sensitive to the known anti-malarial, chloroquine (FIG. 5C) [49-52].

Prior to testing the inhibitory activity of the quaternary hits against the transgenic parasites, it was determined that none of the six compounds inhibited in vitro scDHODH enzymatic activity using the DCIP assay (Table 1). Dose-effect curves measuring parasite proliferation for both the parent and D10-scDHODH strains grown in the presence of the quaternary hits are shown in FIGS. 5A-5D. The efficacy of Compound 1, Compound 5, Compound 6, and Compound 3 against the scDHODH-D10 strain is significantly reduced when compared to the parent parasite strain. Specifically, these four drugs exhibit a biphasic drug-effect profile against the transgenic strain when the $IC_{50}$ values for the second phase of curve is greater than 10 µM (Table 2). This rescued death phenotype concomitant with the addition of exogenous yeast DHODH argues that pfDHODH is the likely in vivo target of Compound 1, Compound 5, Compound 6, and Compound 3. The efficacy of Compound 2 against the scDHODH expressing parasites was markedly reduced in comparison to the parent strain but to a lesser degree than the aforementioned compounds. The anti-malarial activity of Compound 2 may therefore be attributed to multiple targets in addition to pfDHODH. The drug-effect curve for Compound 4 remained constant between the D10 parent and transgenic, scDHODH expressing strain suggesting a mechanism of action other than pfDHODH.

Example 9

Cytotoxicity and In Vitro Metabolism Studies

Cytotoxicity
A. Normal Human Dermal Fibroblast Toxicity Screen Protocol

The Normal Human Dermal Fibroblast Toxicity Screen Protocol is designed to determine whether compound mixtures, breakouts or single compounds are toxic to normal human dermal fibroblasts. The screen involves plating the dermal fibroblasts and then exposing them to the compounds for four days, then cell viability is measured using Alamar Blue reagent.

Reagents:

Normal Human Dermal Fibroblasts (Clonetics Cat# CC-2511); EMEM/EBSS Medium (Cambrex Cat#12-611F); Fetal Bovine Serum (Hyclone Cat# SH300-70); Complete Amino Acids (50×) (Sigma Cat# R-7131); MEM Vitamins (100×) (Sigma Cat# M6895); Pen Strep/L-glut (Cambrex Cat#17-718R); Trypsin, 0.025%/0.01% EDTA (Clonetics Cat# CC-5012); Alamar Blue (Biosource International Cat# DAL1100); 10×DPBS with calcium and magnesium; Dilute to 1× and adjust pH to 7.0 (Sigma Cat# D-1283); Tween 20 (Sigma, Note: 10% Tween 20 Stock is made by diluting the Tween 20 1:10 in Sterile DPBS); Dimethylsulfoxide (DMSO) (Sigma Cat#154938); Costar 96-well flat bottom tissue culture treated plates (Cat#29442-050).

| Growth Media Formulation (from Coriell cell bank) | |
|---|---|
| Formulation | Reagent Volume |
| EMEM/EBSS | 500 mL |
| 15% FBS | 75 mL |
| 2X Amino Acids | 20 mL |
| 2X MEM Vitamins | 10 mL |
| 2N HCl | 1.2 mL (Check pH before adding to see if necessary) |
| Pen-Strep/L-Glut | 4.5 mL (1 vial) |

Sterile Filter Before Use

Freezing Human Dermal Fibroblasts

One vial of Clonetics Dermal Fibroblasts cells was placed into 2 T225 flasks. Growth Media (80 mL) was added to each flask. Cells were grown to ~70-80% confluency. Clonetics Trypsin (4.5 mL) was added to the cells. The cells were incubated at room temperature for 2-3 minutes. Any remaining cells were dislodged and Growth Media (15 mL) was added. Cells were centrifuged for 15 minutes at 1100 rpm. During the centrifugation, freezing media (80% Growth Media, 10% FBS, 10% DMSO) was prepared. The cells were resuspended in freezing media and counted using a hemacytometer. The cells, placed on ice, were diluted to a final concentration of $1 \times 10^6$ cells/ml. Aliquots (1 mL) were dispensed into cryovials and incubated at −80° C. overnight. The cells were placed in a −150° C. freezer cell bank.

Dermal Fibroblast Cell Expansion and Plating:

Day 1:

An aliquot of cells (1 mL) was removed from −150 C freezer cell bank, and thawed in 37° C. water bath. Growth Media (80 mL) was added to cells (at 0.5 ml of $1 \times 10^6$ cells/ml per T225 flask).

Day 5:

Growth Media was removed and replaced with 80 mL of fresh Growth Media.

Day 8:

Growth Media was aspirated, DPBS (20 mL) was added and mixed. The DPBS was then aspirated. Trypsin (4.5 mL) was added to the flask and mixed so the solution coated the entire flask bottom, and the flask was laid flat at RT 2-3 minutes. Remaining cells were dislodged, and fresh Growth Media (30 mL) was added. The cells were counted using a hemacytometer. The Proliferation Assay (1 T225 flask will seed about 10 plates) was then initiated.

Proliferation Assay:

Day 1:

Harvested Dermal Fibroblast cells were diluted in Growth Media to 0.25 to $0.3 \times 10^5$ cells/mL. Cell suspension (200 µL) were plated into wells of Costar 96-well flat bottom tissue culture treated plates, which resulted in 5000-6000 cells/well. NOTE: One plate, the T=0 plate required that 20-30 wells be seeded and all the other plates had 96 wells seeded. Plates were incubated in 37° C./5% $CO_2$ incubator for 24 hours.

Day 2:

Alamar Blue solution (25 µL/well) was added to the T=0 plate and the plate was agitated. The plate in 37° C./5% $CO_2$ incubator was incubated for 3 hours, agitated the and the fluorescence was measured. 10% Tween 20 stock (10 µL) was added into rows A-D in column 1 (positive control). DMSO (0.5 µL) was added into column 2 (negative control). Compounds were placed into designated wells for desired testing as follows:

| Plates of Compound mixtures or Single compounds |
|---|
| Samples were tested at a final concentration of 12.5 µM and diluted using DMSO if necessary. The plates were tested in duplicate. |
| IC50 determination |
| Compounds were tested in duplicate. Compounds were serially diluted from top to bottom (row A contained the highest concentration) in a column. |

Plates were mixed on the shaker, then incubated in 37° C./5% $CO_2$ incubator for 96 hours.

Day 6:

Alamar Blue solution (25 µL/well) was added to the plates containing the compounds, and the plates were agitated. The plates were incubated in 37° C./5% $CO_2$ incubator for 3 hours, agitated and then the fluorescence was measured.

B. Renal Proximal Tubule Epithelial Cell Toxicity Screen

The Renal Proximal Tubule Epithelial Cell Toxicity Screen is designed to determine whether compound mixtures, breakouts or single compounds are toxic to normal renal epithelial cells. In the case of a single compound, they were tested to ascertain the $LC_{50}$, which is the compound concentration at which it is lethal to 50% of the epithelial cells in a well. Basically, the screen consists of plating renal epithelial cells, exposing them to the desired compound(s) for 4 days and measuring cell viability using the Alamar Blue reagent.

Reagents:

Renal Proximal Tubule Epithelial Cells (RPTEC, Clonetics Cat# CC-2553); Renal Epithelial Growth Medium bullet kit (REGM, Clonetics Cat# CC-3190); Fetal Bovine Serum (FBS, HyClone Cat# SH300-70); Trypsin, 0.025%/0.01% EDTA (Clonetics Cat# CC-5012); Trypsin neutralizing solution (TNS, Clonetics Cat# CC-5002); Alamar Blue (Biosource International Cat# DAL1100); 10×DPBS with calcium and magnesium (Dilute to 1× and adjust pH to 7.0; Sigma Cat# D-1283); Tween 20 (Sigma, Note: 10% Tween 20 Stock is made by diluting the Tween 20 1:10 in Sterile DPBS); Dimethylsulfoxide (DMSO, Sigma Cat#154938); Costar 96-well flat bottom tissue culture treated plates (Cat#29442-050)

Note: REGM was prepared AS IS from the bullet kit, no additional reagents were necessary. Media was filtered before use.

Freezing Kidney Epithelial Cells:

One vial of Clonetics renal cells was placed into a T225 flask. REGM (80 mL) was added into the flask. Cells were grown to ~70-80% confluency. The cells were trypsinized using Clonetics Trypsin. Trypsin Neutralization solution was added to the cells. The cells were centrifuged for 8 minutes at 1000 rpm. During the centrifugation step, the freezing media (80% REGM; 10% FBS; 10% DMSO) was prepared. The cells were resuspended in freezing media and counted using a hemacytometer. The cells, placed on ice, were diluted to a final concentration of $1 \times 10^6$ cells/mL. Aliquots (1 or 4 mL) were dispensed into cryovials and incubated at −80° C. overnight. The cells were then incubated in a −150° C. freezer cell bank.

Kidney Epithelial Cell Expansion and Plating

Day 1:

An aliquot (1 or 4 mL) was removed from −150° C. freezer cell bank, and thawed in 37° C. water bath. Cells (1 mL of $1 \times 10^6$ cells/mL) were placed in a T225 flask with REGM (80 mL).

Day 8:

REGM was aspirated, and DPBS (20 mL) was added and mixed. DPBS was aspirated. Trypsin (7 mL) was added and mixed so solution coated entire flask bottom. Cells were observed until they are trypsinized. Remaining cells were dislodged. Trypsin Neutralization solution (7 mL) was added. Cells were centrifuged for 8 minutes at 1000 rpms. The supernatant was removed, and cells were resuspended REGM (8 mL). Cells were counted using a hemacytometer. Proliferation Assay (1 T225 flask will seed about 10 plates) was initiated.

Proliferation Assay

Day 1:

Harvested Kidney Epithelial cells were diluted in REGM to $1.5 \times 10^4$ cells/mL. Cell suspension (200 μL) were placed into wells of Costar 96-well flat bottom tissue culture treated plates, which resulted in 3000 cells/well. NOTE: One plate, the T=0 plate required that 20-30 wells be seeded, and all the other plates had 96 wells seeded. Plates were incubated in 37° C./5% $CO_2$ incubator for 24 hours.

Day 2:

Alamar Blue solution (25 μL/well) was added to the T=0 plate and mixed. The plate was incubated in 37° C./5% $CO_2$ incubator for 4 hours, mixed and then the fluorescence was measured. 10% Tween 20 stock (10 μL) was added into rows A-D in column 1 (positive control). DMSO (0.5 μL) was added into column 2 (negative control). Compounds were placed into designated wells for desired testing as follows:

---

IC50 determination

The compounds were tested in duplicate. Compounds were serially diluted from top to bottom (row A should contain the highest concentration) in a column.
Plates of Compound mixtures or Single compounds

---

Samples were tested at a final concentration of 25 uM and were diluted using DMSO if necessary. The plates were tested in duplicate.

---

Plates were mixed on the shaker, and then incubated in 37° C./5% $CO_2$ incubator for 96 hours.

Day 6:

Alamar Blue solution (25 μL/well) was added to the plates containing the compounds and mixed. Plates were incubated in 37° C./5% $CO_2$ incubator for 4 hours, mixed and the fluorescence was measured.

In Vitro Metabolism

A. Cytochrome P450 Inhibition.

Rapid screening for cytochrome P450 inhibitors is part of the current paradigm for avoiding development of drugs likely to give clinical pharmacokinetic drug-drug interactions and associated toxicities. There are commercially available assays for such screenings. For example, BD Biosciences (http://www.bdbiosciences.com/index.shtml) provides a technical bulletin describing a detailed, step-by-step procedure for the performance of the high throughput cytochrome P450 inhibition testing method.

B. Hepatic Clearance

Clearance of drug by the liver will depend on the rate of delivery of drug to the liver (the hepatic blood flow) and on the efficiency of removal of drug which is presented to it (the extraction ratio). The hepatic clearance of compounds can be determined by standard methods known in the art. Such methods are described in, for example, Naritomi, Y; Terashita, S; Kagayama, A; Sugiyama, Y. "Utility of Hepatocytes in Predicting Drug Metabolism: Comparison of Hepatic Intrinsic Clearance in Rats and Humans in Vivo and in Vitro." 2003, 31 (5): pages 580-588.

TABLE 5

| | Cytotoxicity | | In Vitro Metabolism | |
|---|---|---|---|---|
| Compound # | Kidney Epithelial $LC_{50}$ (μM) | Dermal Fibroblast $LC_{50}$ (μM) | Cytochrome P450 Inhibition (μM) | Hepatic Clearance (μL/min/mg) |
| 1 | >62 | >62 | ND | ND |
| 2 | >62 | >62 | ND | ND |
| 3 | >62 | >62 | ND | ND |
| 4 | 49 | 64 | ND | ND |
| 5 | >62 | >62 | ND | ND |
| 6 | >62 | >62 | ND | ND |
| 7 | 50 | 50 | ND | ND |
| 8 | ND | ND | >5.0 in 1A2<br>>5.0 in 2C19<br>>5.0 in 2C9<br>>5.0 in 2D6<br>>5.0 in 3A4 | >72 Human<br>>119 Rat |
| 9 | ND | ND | >5.0 in 1A2<br>>5.0 in 2C19<br>>5.0 in 2C9<br>>5.0 in 2D6<br>>5.0 in 3A4 | 59 Human<br>104 Rat |
| 10 | ND | ND | >5.0 in 1A2<br>>5.0 in 2C19<br>>5.0 in 2C9<br>>5.0 in 2D6<br>>5.0 in 3A4 | 8 Human<br>16 Rat |
| 11 | >62 | >62 | >5.0 in 1A2<br>>5.0 in 2C19<br>>5.0 in 2C9<br>>5.0 in 2D6<br>>5.0 in 3A4 | 49 Human<br>>119 Rat |
| 12 | >62 | >62 | >5.0 in 1A2<br>>5.0 in 2C19<br>>5.0 in 2C9<br>>5.0 in 2D6<br>>5.0 in 3A4 | 33 Human<br>102 Rat |

REFERENCES

1 Subbayya, I. N., et al., *Metabolic enzymes as potential drug targets in Plasmodium falciparum*. Indian J Med Res, 1997. 106: p. 79-94.
2 Reyes, P.; Rathod, P. K.; Sanchez, D. J.; Mrema, J. E.; Rieckmann, K. H.; Heidrich, H. G. *Enzymes of purine and pyrimidine metabolism from the human malaria parasite, Plasmodium falciparum*. Mol Biochem Parasitol. 1982 May; 5(5):275-90

3 Caroline, D. F., *Pyrimidine synthesis in Neurospora crassa: gene-enzyme relationships.* J Bacteriol, 1969. 100(3): p. 1371-7.

4 Taylor, M. L., et al., *Biosynthetic dihydroorotate dehydrogenase from Lactobacillus bulgaricus.* J Bacteriol, 1971. 105(3): p. 1015-27.

5 Williams, J. C. and G. A. O'Donovan, *Repression of enzyme synthesis of the pyrimidine pathway in Salmonella typhimurium.* J Bacteriol, 1973. 115(3): p. 1071-6.

6 Jones, M. E., *Pyrimidine nucleotide biosynthesis in animals: genes, enzymes, and regulation of UMP biosynthesis.* Annu Rev Biochem, 1980. 49: p. 253-79.

7 Nagy, M., F. Lacroute, and D. Thomas, *Divergent evolution of pyrimidine biosynthesis between anaerobic and aerobic yeasts.* Proc Natl Acad Sci USA, 1992. 89(19): p. 8966-70.

8 Nara, T., T. Hshimoto, and T. Aoki, *Evolutionary implications of the mosaic pyrimidine-biosynthetic pathway in eukaryotes.* Gene, 2000. 257(2): p. 209-22.

9 Rowland, P., et al., *The crystal structure of the flavin containing enzyme dihydroorotate dehydrogenase A from Lactococcus lactis.* Structure, 1997. 5(2): p. 239-52.

10 Bjornberg, O., et al., *Dihydrooxonate is a substrate of dihydroorotate dehydrogenase (DHOD) providing evidence for involvement of cysteine and serine residues in base catalysis.* Arch Biochem Biophys, 2001. 391(2): p. 286-94.

11 Hines, V. and M. Johnston, *Analysis of the kinetic mechanism of the bovine liver mitochondrial dihydroorotate dehydrogenase.* Biochemistry, 1989. 28(3): p. 1222-6.

12 Marcinkeviciene, J., et al., *A second dihydroorotate dehydrogenase (Type A) of the human pathogen Enterococcus faecalis: expression, purification, and steady-state kinetic mechanism.* Arch Biochem Biophys, 2000. 377(1): p. 178-86.

13 Neidhardt, E. A., et al., *Expression and characterization of E. coli-produced soluble, functional human dihydroorotate dehydrogenase: a potential target for immunosuppression.* J Mol Microbiol Biotechnol, 1999. 1(1): p. 183-8.

14 van der Plas, J., et al., *Identification and localization of enzymes of the fumarate reductase and nitrate respiration systems of Escherichia coli by crossed immunoelectrophoresis.* J Bacteriol, 1983. 153(2): p. 1027-37.

15 Skophammer, R. G., et al., *Evidence for a gram-positive, eubacterial root of the tree of life.* Mol Biol Evol, 2007. 24(8): p. 1761-8.

16 Denis-Duphil, M., *Pyrimidine biosynthesis in Saccharomyces cerevisiae: the ura2 cluster gene, its multifunctional enzyme product, and other structural or regulatory genes involved in de novo UMP synthesis.* Biochem Cell Biol, 1989. 67(9): p. 612-31.

17 Jordan, D. B., J. J. Bisaha, and M. A. Picollelli, *Catalytic properties of dihydroorotate dehydrogenase from Saccharomyces cerevisiae: studies on pH, alternate substrates, and inhibitors.* Arch Biochem Biophys, 2000. 378(1): p. 84-92.

18 Chen, J. J. and M. E. Jones, *The cellular location of dihydroorotate dehydrogenase: relation to de novo biosynthesis of pyrimidines.* Arch Biochem Biophys, 1976. 176(1): p. 82-90.

19 Gero, A. M. and W. J. O'Sullivan, *Human spleen dihydroorotate dehydrogenase: properties and partial purification.* Biochem Med, 1985. 34(1): p. 70-82.

20 Knecht, W., et al., *Rat dihydroorotate dehydrogenase: isolation of the recombinant enzyme from mitochondria of insect cells.* Protein Expr Purif, 1997. 10(1): p. 89-99.

21 Taylor, W. H. and M. L. Taylor, *Enzymes of the Pyrimidine Pathway in Escherichia Coli. Ii. Intracellular Localization and Properties of Dihydroorotic Dehydrogenase.* J Bacteriol, 1964. 88: p. 105-10.

22 Loffler, M., et al., *Dihydroorotat-ubiquinone oxidoreductase links mitochondria in the biosynthesis of pyrimidine nucleotides.* Mol Cell Biochem, 1997. 174(1-2): p. 125-9.

23 Miller, R. W. and J. R. Curry, *Mammalian dihydroorotate—ubiquinone reducatse complex. II. Correlation with cytochrome oxidase, mode of linkage with the cytochrome chain, and general properties.* Can J Biochem, 1969. 47(7): p. 725-34.

24 Fry, M. and J. E. Beesley, *Mitochondria of mammalian Plasmodium spp.* Parasitology, 1991. 102 Pt 1: p. 17-26.

25 Aleman, V. and P. Handler, *Dihydroorotate dehydrogenase. I. General properties.* J Biol Chem, 1967. 242(18): p. 4087-96.

26 Gutteridge, W. E., D. Dave, and W. H. Richards, *Conversion of dihydroorotate to orotate in parasitic protozoa.* Biochim Biophys Acta, 1979. 582(3): p. 390-401.

27 Hill, B., et al., *Pyrimidine biosynthesis in Plasmodium berghei.* Int J Biochem, 1981. 13(3): p. 303-10.

28 Painter, H. J., et al., *Specific role of mitochondrial electron transport in blood-stage Plasmodium falciparum.* Nature, 2007. 446(7131): p. 88-91.

29 Eakin, R. T. and H. K. Mitchell, *A mitochondrial dihydroorotate oxidase system in Neurospora crassa.* Arch Biochem Biophys, 1969. 134(1): p. 160-71.

30 Kennedy, J., *Distribution, subcellular localization, and product inhibition of dihydroorotate oxidation in the rat.* Arch Biochem Biophys, 1973. 157(2): p. 369-73.

31 Copeland, R. A., et al., *Recombinant human dihydroorotate dehydrogenase: expression, purification, and characterization of a catalytically functional truncated enzyme.* Arch Biochem Biophys, 1995. 323(1): p. 79-86.

32 Hurt, D. E., A. E. Sutton, and J. Clardy, *Brequinar derivatives and species-specific drug design for dihydroorotate dehydrogenase.* Bioorg Med Chem Lett, 2006. 16(6): p. 1610-5.

33 Liu, S., et al., *Structures of human dihydroorotate dehydrogenase in complex with antiproliferative agents.* Structure, 2000. 8(1): p. 25-33.

34 Powell, G., Rajagopalan K V, Handler P: *Purification and properties of inosinic acid dehydrogenase from Escherichia coli.* J Biol Chem, 1969. 244(17): p. 4793-7.

35 Zameitat, E., et al., *Two different dihydroorotate dehydrogenases from yeast Saccharomyces kluyveri.* FEBS Lett, 2004. 568(1-3): p. 129-34.

36 Michaelis, L. and M. L. Menten, *Die kinetik der invertinwirkung.* Biochem. Z., 1913. 49: p. 333-369.

37 Baldwin, J., et al., *High-throughput screening for potent and selective inhibitors of Plasmodium falciparum dihydroorotate dehydrogenase.* J Biol Chem, 2005. 280(23): p. 21847-53.

38 Zhang, J. H., T. D. Chung, and K. R. Oldenburg, *A Simple Statistical Parameter for Use in Evaluation and Validation of High Throughput Screening Assays.* J Biomol Screen, 1999. 4(2): p. 67-73.

39 Trager, W. and J. B. Jensen, *Human malaria parasites in continuous culture.* Science, 1976. 193(4254): p. 673-5.

40 Chulay, J. D., J. D. Haynes, and C. L. Diggs, *Plasmodium falciparum: assessment of in vitro growth by [3H]hypoxanthine incorporation.* Exp Parasitol, 1983. 55(1): p. 138-46.

41 Geary, T. G., A. A. Divo, and J. B. Jensen, *An in vitro assay system for the identification of potential antimalarial drugs.* J Parasitol, 1983. 69(3): p. 577-83.

41 Antilla, J C; Klapars, A.; Buchwald, S. L. *The copper-catalyzed N-arylation of indoles*. J Am Chem. Soc. 2002 Oct. 2; 124(39):11684-8

43 Baldwin, J., et al., *Malarial dihydroorotate dehydrogenase. Substrate and inhibitor specificity*. J Biol Chem, 2002. 277(44): p. 41827-34.

44 Knecht, W., et al., *Functional expression of a fragment of human dihydroorotate dehydrogenase by means of the baculovirus expression vector system, and kinetic investigation of the purified recombinant enzyme*. Eur J Biochem, 1996. 240(1): p. 292-301.

45 Chen, G. X., et al., *Kinetic and molecular properties of the dihydrofolate reductase from pyrimethamine-sensitive and pyrimethamine-resistant clones of the human malaria parasite Plasmodium falciparum*. Mol Pharmacol, 1987. 31(4): p. 430-7.

46 Wang, P., et al., *Sulfadoxine resistance in the human malaria parasite Plasmodium falciparum is determined by mutations in dihydropteroate synthetase and an additional factor associated with folate utilization*. Mol Microbiol, 1997. 23(5): p. 979-86.

47 Malmquist, N. A., et al., *Analysis of Flavin Oxidation and Electron-Transfer Inhibition in Plasmodium falciparum Dihydroorotate Dehydrogenase*. Biochemistry, 2008. 47(8): p. 2466-75.

48 Fry, M. and M. Pudney, *Site of action of the antimalarial hydroxynaphthoquinone, 2-[trans-4-(4'-chlorophenyl)cyclohexyl]-3-hydroxy-1,4-naphthoquinone (566C80)*. Biochem Pharmacol, 1992. 43(7): p. 1545-53.

49 Banyal, H. S, and C. D. Fitch, *Ferriprotoporphyrin IX binding substances and the mode of action of chloroquine against malaria*. Life Sci, 1982. 31(11): p. 1141-4.

50 Jearnpipatkul, A., et al., *Binding of antimalarial drugs to hemozoin from Plasmodium berghei*. Experientia, 1980. 36(9): p. 1063-4.

51 Phifer, K. O., K. L. Yielding, and S. N. Cohen, *Investigations of the possible relation of ferrihemic acid to drug resistance in Plasmodium berghei*. Exp Parasitol, 1966. 19(1): p. 101-9.

52 Schueler, F. W. and W. F. Cantrell, *Antagonism of the Antimalarial Action of Chloroquine by Ferrihemate and an Hypothesis for the Mechanism of Chloroquine Resistance*. J Pharmacol Exp Ther, 1964. 143: p. 278-81.

While this invention has been particularly shown and described with references to example embodiments thereof, it will be understood by those skilled in the art that various changes in form and details may be made therein without departing from the scope of the invention encompassed by the appended claims.

---

What is claimed is:

1. A compound of Formula V:

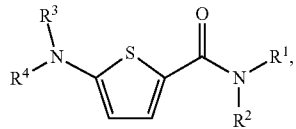

(V)

or a pharmaceutically acceptable salt thereof, wherein:
$R^1$ is ethyl, propyl or cyclopropyl;
$R^2$ is hydrogen;
$R^3$ and $R^4$, along with the nitrogen to which they are attached, form a benzoimidazolyl optionally substituted by one or more groups represented by $R^5$;
each $R^5$ is independently halogen, nitro, cyano, $(C_1-C_3)$ alkyl, halo$(C_1-C_3)$alkyl, hydroxy$(C_1-C_3)$alkyl, $(C_1-C_3)$ alkoxy, halo$(C_1-C_3)$alkoxy, $N(R^6)_2$, $C(=NOH)NH_2$, $NR^6CON(R^6)_2$, $CON(R^6)_2$, $CO_2R^6$, $COR^7$, $OC(O)R^6$, $SO_2N(R^6)_2$, $SO_2R^7$, $NR^6COR^7$, $NR^6CO_2R^6$, $NR^6SO_2R^7$ or $OC(=O)N(R^6)_2$;
each $R^6$ is independently (a) hydrogen; or (b) $(C_1-C_{10})$ alkyl or aryl$(C_0-C_3)$alkyl, each optionally substituted with halogen, $(C_1-C_3)$alkoxy, $(C_1-C_3)$alkyl, halo$(C_1-C_3)$ alkyl, halo$(C_1-C_3)$alkoxy, cyano or nitro; and
each $R^7$ is independently (a) hydrogen or halogen; or (b) $(C_1-C_{10})$alkyl, $(C_1-C_{10})$alkoxy, aryl$(C_0-C_3)$alkyl or aryl $(C_0-C_3)$alkoxy, each optionally substituted with halogen, $(C_1-C_3)$alkoxy, $(C_1-C_3)$alkyl, halo$(C_1-C_3)$alkyl, halo$(C_1-C_3)$alkoxy, cyano or nitro.

2. The compound of claim 1, wherein each $R^5$ is independently halogen, nitro, cyano, $(C_1-C_3)$alkyl, halo$(C_1-C_3)$alkyl, $(C_1-C_3)$alkoxy, halo$(C_1-C_3)$alkoxy, $N(R^6)_2$, $NR^6CON(R^6)_2$, or $CON(R^6)_2$.

3. The compound of claim 1, wherein $R^1$ is cyclopropyl.

4. The compound of claim 1, wherein the benzoimidazolyl formed by $R^3$ and $R^4$, along with the nitrogen to which they are attached, is optionally substituted by one to three groups represented by $R^5$.

5. The compound of claim 4, wherein $R^1$ is cyclopropyl.

6. A compound of Formula VI:

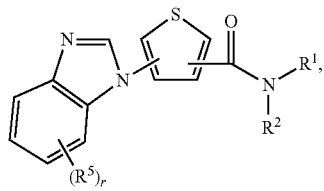

(VI)

or a pharmaceutically acceptable salt thereof, wherein:
$R^1$ is ethyl, propyl or cyclopropyl;
$R^2$ is hydrogen;
each $R^5$ is independently halogen, nitro, cyano, $(C_1-C_3)$ alkyl, halo$(C_1-C_3)$alkyl, hydroxy$(C_1-C_3)$alkyl, $(C_1-C_3)$ alkoxy, halo$(C_1-C_3)$alkoxy, $N(R^6)_2$, $C(=NOH)NH_2$, $NR^6CON(R^6)_2$, $CON(R^6)_2$, $CO_2R^6$, $COR^7$, $OC(O)R^6$, $SO_2N(R^6)_2$, $SO_2R^7$, $NR^6COR^7$, $NR^6CO_2R^6$, $NR^6SO_2R^7$ or $OC(=O)N(R^6)_2$;
each $R^6$ is independently (a) hydrogen; or (b) $(C_1-C_{10})$ alkyl or aryl$(C_0-C_3)$alkyl, each optionally substituted with halogen, $(C_1-C_3)$alkoxy, $(C_1-C_3)$alkyl, halo$(C_1-C_3)$ alkyl, halo$(C_1-C_3)$alkoxy, cyano or nitro;
each $R^7$ is independently (a) hydrogen or halogen; or (b) $(C_1-C_{10})$alkyl, $(C_1-C_{10})$alkoxy, aryl$(C_0-C_3)$alkyl or aryl $(C_0-C_3)$alkoxy, each optionally substituted with halogen, $(C_1-C_3)$alkoxy, $(C_1-C_3)$alkyl, halo$(C_1-C_3)$alkyl, halo$(C_1-C_3)$alkoxy, cyano or nitro; and
r is 0-3, wherein any substitutable hydrogen on a ring carbon atom may be substituted by $R^5$.

7. A pharmaceutical composition comprising: i) a pharmaceutically acceptable carrier or diluent; and ii) a compound of claim 1, or a pharmaceutically acceptable salt thereof.

8. A method of treating malaria in a subject in need thereof, comprising administering to the subject an effective amount of a compound of Formula V:

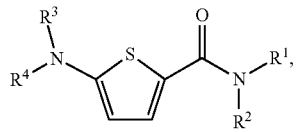

(V)

or a pharmaceutically acceptable salt thereof, wherein:
  $R^1$ and $R^2$ are independently (a) hydrogen; or (b) $(C_1-C_6)$ alkyl or $(C_3-C_6)$cycloalkyl, each optionally substituted with one or more groups represented by $R^5$; or
  $R^1$ and $R^2$, along with the nitrogen to which they are attached, form a heterocyclyl or heteroaryl, wherein each can be monocyclic, bicyclic or tricyclic, wherein the heterocyclyl or heteroaryl formed is optionally substituted by one or more groups represented by $R^5$;
  $R^3$ and $R^4$ are independently (a) hydrogen; or (b) $(C_1-C_{10})$ alkyl, aryl$(C_0-C_3)$alkyl, heteroaryl$(C_0-C_3)$alkyl, cycloalkyl$(C_0-C_3)$alkyl, or heterocyclyl$(C_0-C_3)$alkyl, each optionally substituted with one or more groups represented by $R^5$; or
  $R^3$ and $R^4$, along with the nitrogen to which they are attached, form a heterocyclyl or heteroaryl, wherein each can be monocyclic, bicyclic or tricyclic, wherein the heterocyclyl or heteroaryl formed is optionally substituted by one or more groups represented by $R^5$;
  each $R^5$ is independently halogen, nitro, cyano, $(C_1-C_3)$ alkyl, halo$(C_1-C_3)$alkyl, hydroxy$(C_1-C_3)$alkyl, $(C_1-C_3)$ alkoxy, halo$(C_1-C_3)$alkoxy, $N(R^6)_2$, $C(=NOH)NH_2$, $NR^6CON(R^6)_2$, $CON(R^6)_2$, $CO_2R^6$, $COR^7$, $OC(O)R^6$, $SO_2N(R^6)_2$, $SO_2R^7$, $NR^6COR^7$, $NR^6CO_2R^6$, $NR^6SO_2R^7$ or $OC(=O)N(R^6)_2$;
  each $R^6$ is independently (a) hydrogen; or (b) $(C_1-C_{10})$ alkyl or aryl$(C_0-C_3)$alkyl, each optionally substituted with halogen, $(C_1-C_3)$alkoxy, $(C_1-C_3)$alkyl, halo$(C_1-C_3)$ alkyl, halo$(C_1-C_3)$alkoxy, cyano or nitro; and
  each $R^7$ is independently (a) hydrogen or halogen; or (b) $(C_1-C_{10})$alkyl, $(C_1-C_{10})$alkoxy, aryl$(C_0-C_3)$alkyl or aryl $(C_0-C_3)$alkoxy, each optionally substituted with halogen, $(C_1-C_3)$alkoxy, $(C_1-C_3)$alkyl, halo$(C_1-C_3)$alkyl, halo$(C_1-C_3)$alkoxy, cyano or nitro.

9. The method of claim 8, wherein the compound is not represented by any of the following structural formulas:

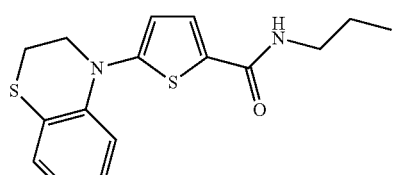

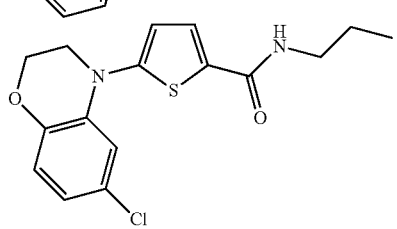

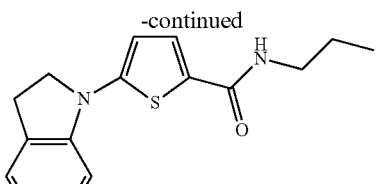

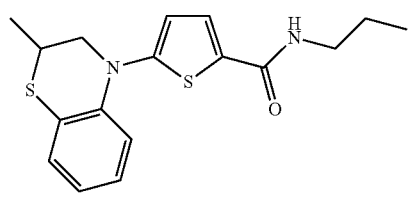

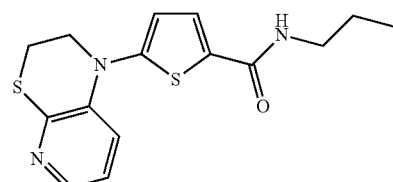

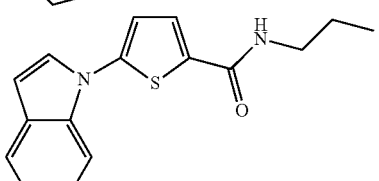

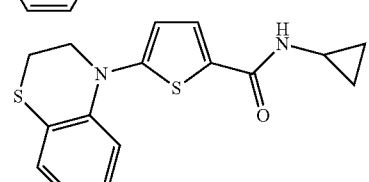

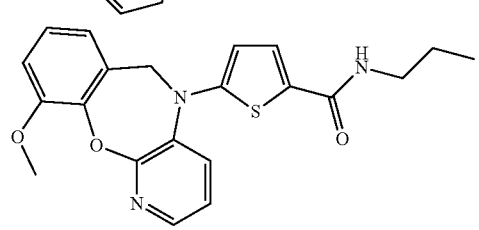

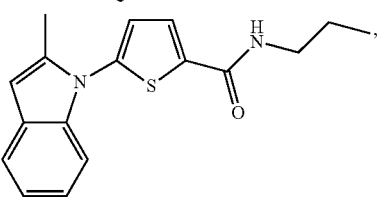

or a pharmaceutically acceptable salt thereof.

10. The method of claim 8, wherein the method is a method of therapeutically treating malaria in a subject in need thereof.

11. The method of claim 8, wherein the method is a method of prophylactically treating malaria in a subject in need thereof.

* * * * *

UNITED STATES PATENT AND TRADEMARK OFFICE
CERTIFICATE OF CORRECTION

PATENT NO.       : 8,703,811 B2
APPLICATION NO. : 12/991305
DATED            : April 22, 2014
INVENTOR(S)      : Bastos et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 276 days.

Signed and Sealed this

Twenty-ninth Day of September, 2015

Michelle K. Lee
*Director of the United States Patent and Trademark Office*

SEQUENCE LISTING

<160> NUMBER OF SEQ ID NOS: 5

<210> SEQ ID NO 1
<211> LENGTH: 569
<212> TYPE: PRT
<213> ORGANISM: Plasmodium falciparum

<400> SEQUENCE: 1

```
Met Ile Ser Lys Leu Lys Pro Gln Phe Met Phe Leu Pro Lys Lys His
1               5                   10                  15

Ile Leu Ser Tyr Cys Arg Lys Asp Val Leu Asn Leu Phe Glu Gln Lys
            20                  25                  30

Phe Tyr Tyr Thr Ser Lys Arg Lys Glu Ser Asn Asn Met Lys Asn Glu
        35                  40                  45

Ser Leu Leu Arg Leu Ile Asn Tyr Asn Arg Tyr Tyr Asn Lys Ile Asp
50                  55                  60

Ser Asn Asn Tyr Tyr Asn Gly Gly Lys Ile Leu Ser Asn Asp Arg Gln
65                  70                  75                  80

Tyr Ile Tyr Ser Pro Leu Cys Glu Tyr Lys Lys Lys Ile Asn Asp Ile
                85                  90                  95

Ser Ser Tyr Val Ser Val Pro Phe Lys Ile Asn Ile Arg Asn Leu Gly
            100                 105                 110

Thr Ser Asn Phe Val Asn Asn Lys Lys Asp Val Leu Asp Asn Asp Tyr
        115                 120                 125

Ile Tyr Glu Asn Ile Lys Lys Glu Lys Ser Lys His Lys Lys Ile Ile
130                 135                 140

Phe Leu Leu Phe Val Ser Leu Phe Gly Leu Tyr Gly Phe Phe Glu Ser
145                 150                 155                 160

Tyr Asn Pro Glu Phe Phe Leu Tyr Asp Ile Phe Leu Lys Phe Cys Leu
                165                 170                 175

Lys Tyr Ile Asp Gly Glu Ile Cys His Asp Leu Phe Leu Leu Leu Gly
            180                 185                 190
```

Lys Tyr Asn Ile Leu Pro Tyr Asp Thr Ser Asn Asp Ser Ile Tyr Ala
            195                 200                 205

Cys Thr Asn Ile Lys His Leu Asp Phe Ile Asn Pro Phe Gly Val Ala
    210                 215                 220

Ala Gly Phe Asp Lys Asn Gly Val Cys Ile Asp Ser Ile Leu Lys Leu
225                 230                 235                 240

Gly Phe Ser Phe Ile Glu Ile Gly Thr Ile Thr Pro Arg Gly Gln Thr
                245                 250                 255

Gly Asn Ala Lys Pro Arg Ile Phe Arg Asp Val Glu Ser Arg Ser Ile
            260                 265                 270

Ile Asn Ser Cys Gly Phe Asn Asn Met Gly Cys Asp Lys Val Thr Glu
        275                 280                 285

Asn Leu Ile Leu Phe Arg Lys Arg Gln Glu Glu Asp Lys Leu Leu Ser
    290                 295                 300

Lys His Ile Val Gly Val Ser Ile Gly Lys Asn Lys Asp Thr Val Asn
305                 310                 315                 320

Ile Val Asp Asp Leu Lys Tyr Cys Ile Asn Lys Ile Gly Arg Tyr Ala
                325                 330                 335

Asp Tyr Ile Ala Ile Asn Val Ser Ser Pro Asn Thr Pro Gly Leu Arg
            340                 345                 350

Asp Asn Gln Glu Ala Gly Lys Leu Lys Asn Ile Ile Leu Ser Val Lys
        355                 360                 365

Glu Glu Ile Asp Asn Leu Gly Lys Asn Asn Ile Met Asn Asp Glu Ser
    370                 375                 380

Thr Tyr Asn Glu Asp Asn Lys Ile Val Glu Lys Lys Asn Asn Phe Asn
385                 390                 395                 400

Lys Asn Asn Ser His Met Met Lys Asp Ala Lys Asp Asn Phe Leu Trp
                405                 410                 415

Phe Asn Thr Thr Lys Lys Pro Leu Val Phe Val Lys Leu Ala Pro
            420                 425                 430

Asp Leu Asn Gln Glu Gln Lys Lys Glu Ile Ala Asp Val Leu Leu Glu
        435                 440                 445

Thr Asn Ile Asp Gly Met Ile Ile Ser Asn Thr Thr Thr Gln Ile Asn
    450                 455                 460

Asp Ile Lys Ser Phe Glu Asn Lys Lys Gly Gly Val Ser Gly Ala Lys
465                 470                 475                 480

Leu Lys Asp Ile Ser Thr Lys Phe Ile Cys Glu Met Tyr Asn Tyr Thr
                485                 490                 495

Asn Lys Gln Ile Pro Ile Ile Ala Ser Gly Gly Ile Phe Ser Gly Leu
            500                 505                 510

Asp Ala Leu Glu Lys Ile Glu Ala Gly Ala Ser Val Cys Gln Leu Tyr
        515                 520                 525

Ser Cys Leu Val Phe Asn Gly Met Lys Ser Ala Val Gln Ile Lys Arg
    530                 535                 540

Glu Leu Asn His Leu Leu Tyr Gln Arg Gly Tyr Tyr Asn Leu Lys Glu
545                 550                 555                 560

Ala Ile Gly Arg Lys His Ser Lys Ser
                565

<210> SEQ ID NO 2
<211> LENGTH: 418
<212> TYPE: PRT
<213> ORGANISM: Plasmodium berghei

<400> SEQUENCE: 2

-continued

```
Met Lys Arg Phe Asp Glu Arg Met Asn Lys Glu Lys Ser Lys His Lys
 1               5                  10                  15
Lys Val Leu Phe Phe Ile Phe Ser Ser Ile Val Gly Leu Tyr Met Tyr
             20                  25                  30
Phe Glu Ser Tyr Asn Pro Glu Phe Phe Met Tyr Asp Val Phe Leu Asp
         35                  40                  45
Phe Cys Leu Asn Tyr Val Asp Ser Glu Val Cys His Asp Leu Phe Leu
     50                  55                  60
Leu Leu Gly Lys Tyr Gly Leu Leu Pro Tyr Asp Thr Ser Asn Asp Ser
 65                  70                  75                  80
Val Tyr Ala Thr Ser Asp Ile Lys Asn Leu Asn Phe Ile Asn Pro Phe
                 85                  90                  95
Gly Val Ala Ala Gly Phe Asp Lys Asn Gly Ile Cys Ile Asp Ser Ile
                100                 105                 110
Leu Lys Leu Gly Phe Ser Phe Ile Glu Ile Gly Thr Ile Thr Pro Lys
                115                 120                 125
Pro Gln Lys Gly Asn Asn Lys Pro Arg Ile Phe Arg Asp Val Glu Asn
        130                 135                 140
Lys Ser Ile Ile Asn Ala Cys Gly Phe Asn Asn Ile Gly Cys Asp Lys
145                 150                 155                 160
Val Thr Glu Asn Leu Ile Asn Phe Arg Lys Lys Gln Glu Glu Asp Lys
                165                 170                 175
Leu Leu Ser Lys His Ile Val Gly Val Ser Ile Gly Lys Asn Lys His
                180                 185                 190
Thr Glu Asn Ile Val Asp Asp Leu Lys Tyr Ser Ile Tyr Lys Ile Ala
            195                 200                 205
Arg Tyr Ala Asp Tyr Ile Ala Ile Asn Val Ser Ser Pro Asn Thr Pro
210                 215                 220
Gly Leu Arg Asp Asn Gln Glu Ser Asn Lys Leu Lys Asn Ile Ile Leu
225                 230                 235                 240
Phe Val Lys Gln Glu Ile Asn Lys Ile Glu Gln Ile Gly His Asn Gly
                245                 250                 255
Glu Thr Phe Trp Met Asn Thr Ile Lys Lys Pro Leu Val Phe Val
                260                 265                 270
Lys Leu Ala Pro Asp Leu Glu Asn Ser Glu Lys Lys Ile Ala Gln
            275                 280                 285
Val Leu Leu Asp Thr Gly Ile Asp Gly Met Ile Ile Ser Asn Thr Thr
        290                 295                 300
Ile Asn Lys Met Asp Ile Lys Ser Phe Glu Asp Lys Lys Gly Gly Val
305                 310                 315                 320
Ser Gly Lys Lys Leu Lys Asp Leu Ser Thr Asn Leu Ile Ser Asp Met
                325                 330                 335
Tyr Ile Tyr Thr Asn Lys Gln Ile Pro Ile Ile Ala Ser Gly Gly Ile
                340                 345                 350
Leu Thr Gly Ala Asp Ala Leu Glu Lys Ile Glu Ala Gly Ala Ser Val
            355                 360                 365
Cys Gln Leu Tyr Ser Cys Leu Val Phe Asn Gly Val Lys Ser Ala Ile
        370                 375                 380
Gln Ile Lys Arg Glu Phe Asn Asn Ala Leu Tyr Gln Lys Gly Tyr Tyr
385                 390                 395                 400
Asn Leu Arg Glu Ala Ile Gly Lys Lys His Ser Asn Ala Lys Ser Leu
            405                 410                 415
Lys Val
```

```
<210> SEQ ID NO 3
<211> LENGTH: 572
<212> TYPE: PRT
<213> ORGANISM: Plasmodium vivax

<400> SEQUENCE: 3

Met Leu Arg His Ser Cys Leu Arg Glu Lys Gly Asn Leu Ile Gly Gly
  1               5                  10                  15

Ser Leu Leu Arg Gly Ile Ser Ala Gln Leu Arg Ala Ala Gly Gly Gly
             20                  25                  30

Thr Phe Arg Ser Phe His Ser Tyr Arg Ser Phe Cys Ser Phe Cys Ile
         35                  40                  45

Phe Arg Arg Ala Asn Lys Ala Asp Ala Asn Trp Tyr Gly Cys Phe Pro
 50                  55                  60

Gly His Val Ala Gly Ala Thr Cys Gly Pro Leu Arg Gly Asp Cys
 65                  70                  75                  80

Ala Glu Arg His Lys Leu Met Ala His Val Arg Arg Phe Ser Gly Glu
                 85                  90                  95

Ser Thr Arg Ala Lys Gly Gly Asp Lys Arg Glu Gly Asp Ile Glu Gly
            100                 105                 110

Asn Arg Thr Asn Gly Ser Asp Lys Thr Lys Gln Leu Glu Glu Glu Met
        115                 120                 125

Lys Lys Leu Asn Glu Gln Ile Ala Arg Glu Lys Gly Asn His Lys Lys
130                 135                 140

Ala Leu Leu Phe Ile Phe Thr Cys Val Val Ala Leu Tyr Met Tyr Phe
145                 150                 155                 160

Glu Ser Tyr Asp Pro Glu Phe Phe Leu Tyr Asp Val Phe Leu Lys Met
                165                 170                 175

Leu Leu Lys Tyr Val Asp Gly Glu Thr Cys His Glu Leu Phe Leu Leu
            180                 185                 190

Met Gly Lys Tyr Lys Leu Leu Pro Tyr Asp Thr Gly Lys Asp Asn Ile
        195                 200                 205

Tyr Ser Cys Ser Glu Ile Lys Gly Leu Asn Phe Ile Asn Pro Phe Gly
210                 215                 220

Val Ala Ala Gly Phe Asp Lys Asn Gly Val Cys Ile Asp Gly Ile Leu
225                 230                 235                 240

Lys Leu Gly Phe Ser Phe Ile Glu Ile Gly Thr Ile Thr Pro Lys Ala
                245                 250                 255

Gln Lys Gly Asn Glu Arg Pro Arg Ile Phe Arg Asp Leu Glu Thr Arg
            260                 265                 270

Ser Ile Ile Asn Ser Cys Gly Phe Asn Asn Met Gly Cys Asp Glu Val
        275                 280                 285

Cys Lys Asn Leu Lys Arg Phe Arg Glu Arg Gln Lys Thr Asp Lys Leu
290                 295                 300

Leu Gln Arg His Leu Val Gly Val Ser Leu Gly Lys Asn Lys Asp Ser
305                 310                 315                 320

Pro Asp Ile Leu Gln Asp Leu Ser Tyr Cys Ile Gly Lys Ile Gly Arg
                325                 330                 335

Tyr Ala Asp Tyr Ile Ala Ile Asn Val Ser Ser Pro Asn Thr Pro Gly
            340                 345                 350

Leu Arg Asp His Gln Lys Gly Glu Arg Leu His Gly Ile Ile Gln Arg
        355                 360                 365

Val Lys Glu Glu Val Ala Lys Leu Asp Gly Gly Ala Pro Leu Gly
370                 375                 380
```

```
Gly Ala Thr Thr Gly Ala Ala Met Gly Gly Ala Thr Thr Gly Glu
385                 390                 395                 400

Ala Val Val Gly Lys Ala Pro Pro Asp Glu Ala Ala Thr Gly Gly Glu
                405                 410                 415

Pro Trp Ala Asn Thr Thr Lys Arg Arg Pro Leu Ile Phe Val Lys Leu
            420                 425                 430

Ala Pro Asp Leu Glu Glu Gly Glu Arg Lys Ser Ile Ala Asn Val Leu
            435                 440                 445

Leu Asn Ala Glu Val Asp Gly Met Ile Ile Cys Asn Thr Thr Thr Gln
    450                 455                 460

Lys Phe Asn Ile Lys Ser Phe Glu Asp Lys Lys Gly Gly Val Ser Gly
465                 470                 475                 480

Glu Lys Leu Lys Gly Val Ser Thr His Met Ile Ser Gln Met Tyr Asn
                485                 490                 495

Tyr Thr Asn Gly Lys Ile Pro Ile Ile Ala Ser Gly Gly Ile Phe Thr
            500                 505                 510

Gly Glu Asp Ala Leu Glu Lys Ile Glu Ala Gly Ala Ser Val Cys Gln
            515                 520                 525

Leu Tyr Ser Cys Leu Val Phe Asn Gly Met Lys Ala Ala Val Arg Ile
    530                 535                 540

Lys Arg Glu Leu Asp His Leu Leu Tyr Gln Arg Gly Tyr Tyr Lys Leu
545                 550                 555                 560

Gly Asp Ala Val Gly Arg Ala His Arg Arg Ala Ala
                565                 570

<210> SEQ ID NO 4
<211> LENGTH: 395
<212> TYPE: PRT
<213> ORGANISM: Homo sapiens

<400> SEQUENCE: 4

Met Ala Trp Arg His Leu Lys Lys Arg Ala Gln Asp Ala Val Ile Ile
1               5                   10                  15

Leu Gly Gly Gly Gly Leu Leu Phe Ala Ser Tyr Leu Met Ala Thr Gly
                20                  25                  30

Asp Glu Arg Phe Tyr Ala Glu His Leu Met Pro Thr Leu Gln Gly Leu
            35                  40                  45

Leu Asp Pro Glu Ser Ala His Arg Leu Ala Val Arg Phe Thr Ser Leu
    50                  55                  60

Gly Leu Leu Pro Arg Ala Arg Phe Gln Asp Ser Asp Met Leu Glu Val
65                  70                  75                  80

Arg Val Leu Gly His Lys Phe Arg Asn Pro Val Gly Ile Ala Ala Gly
                85                  90                  95

Phe Asp Lys His Gly Glu Ala Val Asp Gly Leu Tyr Lys Met Gly Phe
            100                 105                 110

Gly Phe Val Glu Ile Gly Ser Val Thr Pro Lys Pro Gln Glu Gly Asn
            115                 120                 125

Pro Arg Pro Arg Val Phe Arg Leu Pro Glu Asp Gln Ala Val Ile Asn
130                 135                 140

Arg Tyr Gly Phe Asn Ser His Gly Leu Ser Val Val Glu His Arg Leu
145                 150                 155                 160

Arg Ala Arg Gln Gln Lys Gln Ala Lys Leu Thr Glu Asp Gly Leu Pro
                165                 170                 175

Leu Gly Val Asn Leu Gly Lys Asn Lys Thr Ser Val Asp Ala Ala Glu
            180                 185                 190
```

```
Asp Tyr Ala Glu Gly Val Arg Val Leu Gly Pro Leu Ala Asp Tyr Leu
        195                 200                 205

Val Val Asn Val Ser Ser Pro Asn Thr Ala Gly Leu Arg Ser Leu Gln
    210                 215                 220

Gly Lys Ala Glu Leu Arg Arg Leu Leu Thr Lys Val Leu Gln Glu Arg
225                 230                 235                 240

Asp Gly Leu Arg Arg Val His Arg Pro Ala Val Leu Val Lys Ile Ala
                245                 250                 255

Pro Asp Leu Thr Ser Gln Asp Lys Glu Asp Ile Ala Ser Val Val Lys
                260                 265                 270

Glu Leu Gly Ile Asp Gly Leu Ile Val Thr Asn Thr Val Ser Arg
            275                 280                 285

Pro Ala Gly Leu Gln Gly Ala Leu Arg Ser Glu Thr Gly Gly Leu Ser
    290                 295                 300

Gly Lys Pro Leu Arg Asp Leu Ser Thr Gln Thr Ile Arg Glu Met Tyr
305                 310                 315                 320

Ala Leu Thr Gln Gly Arg Val Pro Ile Ile Gly Val Gly Gly Val Ser
                325                 330                 335

Ser Gly Gln Asp Ala Leu Glu Lys Ile Arg Ala Gly Ala Ser Leu Val
                340                 345                 350

Gln Leu Tyr Thr Ala Leu Thr Phe Trp Gly Pro Pro Val Val Gly Lys
            355                 360                 365

Val Lys Arg Glu Leu Glu Ala Leu Leu Lys Glu Gln Gly Phe Gly Gly
        370                 375                 380

Val Thr Asp Ala Ile Gly Ala Asp His Arg Arg
385                 390                 395

<210> SEQ ID NO 5
<211> LENGTH: 314
<212> TYPE: PRT
<213> ORGANISM: Saccharomyces cerevisiae

<400> SEQUENCE: 5

Met Thr Ala Ser Leu Thr Thr Lys Phe Leu Asn Asn Thr Tyr Glu Asn
1               5                   10                  15

Pro Phe Met Asn Ala Ser Gly Val His Cys Met Thr Thr Gln Glu Leu
                20                  25                  30

Asp Glu Leu Ala Asn Ser Lys Ala Gly Ala Phe Ile Thr Lys Ser Ala
            35                  40                  45

Thr Thr Leu Glu Arg Glu Gly Asn Pro Glu Pro Arg Tyr Ile Ser Val
        50                  55                  60

Pro Leu Gly Ser Ile Asn Ser Met Gly Leu Pro Asn Glu Gly Ile Asp
65                  70                  75                  80

Tyr Tyr Leu Ser Tyr Val Leu Asn Arg Gln Lys Asn Tyr Pro Asp Ala
                85                  90                  95

Pro Ala Ile Phe Phe Ser Val Ala Gly Met Ser Ile Asp Glu Asn Leu
            100                 105                 110

Asn Leu Leu Arg Lys Ile Gln Asp Ser Glu Phe Asn Gly Ile Thr Glu
        115                 120                 125

Leu Asn Leu Ser Cys Pro Asn Val Pro Gly Lys Pro Gln Val Ala Tyr
    130                 135                 140

Asp Phe Asp Leu Thr Lys Glu Thr Leu Glu Lys Val Phe Ala Phe Phe
145                 150                 155                 160

Lys Lys Pro Leu Gly Val Lys Leu Pro Pro Tyr Phe Asp Phe Ala His
                165                 170                 175
```

```
Phe Asp Ile Met Ala Lys Ile Leu Asn Glu Phe Pro Leu Ala Tyr Val
            180                 185                 190

Asn Ser Ile Asn Ser Ile Gly Asn Gly Leu Phe Ile Asp Val Glu Lys
        195                 200                 205

Glu Ser Val Val Val Lys Pro Arg Asn Gly Phe Gly Gly Ile Gly Gly
    210                 215                 220

Glu Tyr Val Lys Pro Thr Ala Leu Ala Asn Val Arg Ala Phe Tyr Thr
225                 230                 235                 240

Arg Leu Arg Pro Glu Ile Lys Val Ile Gly Thr Gly Gly Ile Lys Ser
                245                 250                 255

Gly Lys Asp Ala Phe Glu His Leu Leu Cys Gly Ala Ser Met Leu Gln
            260                 265                 270

Ile Gly Thr Glu Leu Gln Lys Glu Gly Val Lys Ile Phe Glu Arg Ile
        275                 280                 285

Glu Lys Glu Leu Lys Asp Ile Met Glu Ala Lys Gly Tyr Thr Ser Ile
    290                 295                 300

Asp Gln Phe Arg Gly Lys Leu Asn Ser Ile
305                 310
```